US011401527B2

(12) United States Patent
Tretiakova et al.

(10) Patent No.: US 11,401,527 B2
(45) Date of Patent: Aug. 2, 2022

(54) COMPOSITIONS AND METHODS USEFUL FOR PROPHYLAXIS OF ORGANOPHOSPHATES

(71) Applicant: The Trustees of the University of Pennsylvania, Philadelphia, PA (US)

(72) Inventors: Anna P. Tretiakova, Woburn, MA (US); James M. Wilson, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 537 days.

(21) Appl. No.: 16/093,411

(22) PCT Filed: Apr. 15, 2017

(86) PCT No.: PCT/US2017/027824

§ 371 (c)(1),
(2) Date: Oct. 12, 2018

(87) PCT Pub. No.: WO2017/184463

PCT Pub. Date: Oct. 26, 2017

(65) Prior Publication Data

US 2019/0144884 A1 May 16, 2019

Related U.S. Application Data

(60) Provisional application No. 62/323,781, filed on Apr. 17, 2016, provisional application No. 62/331,262, filed on May 3, 2016.

(51) Int. Cl.

| | |
|---|---|
| ***C12N 15/86*** | (2006.01) |
| ***A61K 35/761*** | (2015.01) |
| ***A61K 9/00*** | (2006.01) |
| ***C12N 9/18*** | (2006.01) |

(52) U.S. Cl.

CPC .............. *C12N 15/86* (2013.01); *A61K 9/007* (2013.01); *A61K 9/0019* (2013.01); *A61K 35/761* (2013.01); *C12N 9/18* (2013.01); *C07K 2319/70* (2013.01); *C12N 2750/14143* (2013.01); *C12N 2800/22* (2013.01)

(58) Field of Classification Search

None

See application file for complete search history.

(56) References Cited

U.S. PATENT DOCUMENTS

| | | | |
|---|---|---|---|
| 5,658,785 | A | 8/1997 | Johnson |
| 6,566,118 | B1 | 5/2003 | Atkinson et al. |
| 6,596,535 | B1 | 7/2003 | Carter |
| 6,723,551 | B2 | 4/2004 | Kotin et al. |
| 7,125,717 | B2 | 10/2006 | Carter |
| 7,282,199 | B2 | 10/2007 | Gao et al. |
| 7,456,683 | B2 | 11/2008 | Takano et al. |
| 7,588,772 | B2 | 9/2009 | Kay et al. |
| 7,790,449 | B2 | 9/2010 | Gao et al. |
| 7,906,111 | B2 | 3/2011 | Wilson et al. |
| 8,319,480 | B2 | 11/2012 | Ko et al. |
| 8,962,330 | B2 | 2/2015 | Gao et al. |
| 8,962,332 | B2 | 2/2015 | Gao et al. |
| 9,062,321 | B2 | 6/2015 | Mor et al. |
| 2002/0151068 | A1 | 10/2002 | Haley et al. |
| 2007/0036760 | A1 | 2/2007 | Wilson et al. |
| 2007/0134205 | A1 | 6/2007 | Rosenberg |
| 2009/0197338 | A1 | 8/2009 | Vandenberghe et al. |
| 2010/0047174 | A1 | 2/2010 | Kay et al. |
| 2012/0282695 | A1 | 11/2012 | Blain et al. |
| 2013/0045186 | A1 | 2/2013 | Gao et al. |
| 2013/0059732 | A1 | 3/2013 | Lisowski et al. |
| 2014/0065666 | A1 | 3/2014 | Simpson et al. |
| 2014/0094392 | A1 | 4/2014 | Bowers et al. |
| 2014/0127749 | A1 | 5/2014 | Mason et al. |
| 2015/0374803 | A1 | 12/2015 | Wolfe |

FOREIGN PATENT DOCUMENTS

| | | |
|---|---|---|
| EP | 1310571 | 2/2006 |
| EP | 2692868 | 2/2014 |
| WO | WO-1999/015685 | 4/1999 |
| WO | WO-2003/042397 | 5/2003 |
| WO | WO-2005/033321 | 4/2005 |
| WO | WO-2006/110689 | 10/2006 |
| WO | WO-2014/124282 | 8/2014 |
| WO | WO-2014/070949 | 5/2015 |
| WO | WO-2015/175639 | 11/2015 |

OTHER PUBLICATIONS

Alexander et al., IInsulin stimulates glyceraldehyde-3-phosphate dehydrogenase gene expression through cis-acting DNA sequences, PNAS, vol. 85: 5092-5096, Jul. 1988.

Clement et al., Large-scale adeno-associated viral vector production using a herpesvirus-based system enables manufacturing for clinical studies, Hum Gene Therapy, vol. 20: 796-806, Aug. 2009.

Dwyer et al, Novel human butyrylcholinesterase variants: toward organophosphonate detoxication, Biochemistry, vol. 453(27): 4476-4487, Jul. 2014.

Ercolani et al., Isolation and Complete Sequence of a Functional Human Glyceraldehyde-3-phosphate Dehydrogenase Gene, J. Biol. Chem, vol. 263: 15335-15341, Oct. 1988.

Gao et al., Adeno-associated viruses undergo substantial evolution in primates during natural infections, PNAS, vol. 100 (10): 6081-6086, May 2003.

(Continued)

*Primary Examiner* — Robert M Kelly

(74) *Attorney, Agent, or Firm* — Howson and Howson; Cathy A. Kodroff

(57) ABSTRACT rAAV compositions useful for preventing the toxicity associated with organophosphate exposure are provided herein. The rAAV co-express a human butyrylcholinesterase and a proline-rich peptide. Each the esterase and the peptide may have an exogenous signal sequence. Also provided are compositions, e.g., aqueous liquid suspensions containing the rAAV.

13 Claims, 21 Drawing Sheets

Specification includes a Sequence Listing.

(56) References Cited

OTHER PUBLICATIONS

Gao et al., Biology of AAV serotype vectors in liver-directed gene transfer to nonhuman primates, Mol Ther, vol. 13: 77-87, Jan. 2006 (ePub Oct. 2005).
GenBank Accession No. AAA35934.1, glutathione S-transferase [*Homo sapiens*], Jun. 1993.
GenBank Accession No. AAA70226.1, glutathione S-transferase [*Homo sapiens*], Jul. 1995.
GenBank Accession No. BAA13327.1, rhodanese [*Homo sapiens*], Feb. 1999.
GenBank Accession No. YP_077180, apsid protein [Adeno-associated virus—8], Aug. 2018.
Gossen, Tight control of gene expression in mammalian cells by tetracycline-responsive promoters, PNAS, vol. 89: 5547-5551, Jun. 1992.
Grimm et al., Titration of AAV-2 particles via a novel capsid ELISA: packaging of genomes can limit production of recombinant AAV-2, Gene Therapy, vol. 6:1322-1330, Mar. 1999.
Kotin, Large-scale recombinant adeno-associated virus production, Hu Mol Genet, vol. 20(R1): R2-R6, May 2011.
Levitt et al., Definition of an efficient synthetic poly(A) site, Genes Dev., vol. 3(7): 1019-25, Jul. 1989.
Lock et al., Absolute Determination of Single-Stranded and Self-Complementary Adeno-Associated Viral Vector Genome titers by Droplet Digital PCR, Hu Gene Therapy Methods, vol. 25(2):115-25, Apr. 2014 (ePub Feb. 2014).
Masson et al., Catalytic bioscavengers against toxic esters, an alternative approach for prophylaxis and treatments of poisonings, Acta Nature, vol. 1(1): 68-79, Apr. 2009.
McCarty et al, Self-complementary recombinant adeno-associated virus (scAAV) vectors promote efficient transduction independently of DNA synthesis, Gene Therapy, vol. 8(16): 1248-1254, Aug. 2001.
Mietzsch et al., OneBac: platform for scalable and high-titer production of adeno-associated virus serotype 1-12 vectors for gene therapy, Hum Gene Therapy, vol. 25: 212-222, Mar. 2014.
Ng, Nuc. Regulation of Human β-actin promoter by upstream and intron domains, Acid Res, vol. 17(2):601-615, Jan. 1989.
Quitsche et al., The β Actin Promoter, J. Biol. Chem, vol. 264:9539-9545, Jun. 1989.
Radcliffe et al., Multiple gene products from a single vector: 'self-cleaving' 2A peptides, Gene Therapy, vol. 11: 1673-1674, Jan. 2004.
Sommer et al., Quantification of Adeno-Associated Virus Particles and Empty Capsids by Optical Density Measurement, Molec. Ther, vol. 7:122-128, Jan. 2003.
Thomson et al., A comprehensive comparison of multiple sequence alignments, Nucl. Acids. Res., vol. 27(13): 2682-2690, May 1999.
Virag et al., Producing Recombinant Adeno-Associated Virus in Foster Cells: Overcoming Production Limitations Using a Baculovirus-Insect Cell Expression Strategy, Hu Gene Therapy, vol. 20: 807-817, Aug. 2009.
Wobus et al., Monoclonal Antibodies against the Adeno-Associated Virus Type 2 (AAV-2) Capsid: Epitope Mapping and Identification of Capsid Domains Involved in AAV-2-Cell Interaction and Neutralization of AAV-2 Infection, J. Virol, vol. 74:9281-9293, Oct. 2000.
Xia et al., siRNA-mediated gene silencing in vitro and in vivo, Nat Biotechnol, vol. 20(10): 1006-10, Oct. 2002 (ePub Sep. 2002).
Thomas et al, Scalable recombinant adeno-associated virus production using recombinant herpes simplex virus type 1 coinfection of suspension-adapted mammalian cells, Hum Gene Ther, 20: 861-870, Aug. 2009.
International Search Report and Written Opinion, dated Aug. 7, 2017, issued in International Patent Application No. PCT/US2017/027824.
U.S. Appl. No. 62/323,781, filed Apr. 17, 2016.
U.S. Appl. No. 62/331,262, filed May 3, 2016.
U.S. Appl. No. 62/266,341, filed Dec. 11, 2015.

COMPOSITIONS AND METHODS USEFUL FOR PROPHYLAXIS OF ORGANOPHOSPHATES

STATEMENT OF FEDERALLY SPONSORED RESEARCH

This invention was made with government support awarded by Defense Threat Reduction Agency of the Department of Defense (DTRA) Contract #HDTRA1-15-C-0023. The government has certain rights in the invention.

This invention was made with government support under grant number HDTRA1-15-1-0023 awarded by the Department of Defense. The government has certain rights in the invention.

INCORPORATION-BY-REFERENCE OF MATERIAL SUBMITTED IN ELECTRONIC FORM

Applicant hereby incorporates by reference the Sequence Listing material filed in electronic form herewith. This file is labeled "UPN-16-7803PCT ST25.txt".

BACKGROUND OF THE INVENTION

Human butyrylcholinesterase (hBChE) is a widely-distributed enzyme that may play a role in nerve conduction, can hydrolyze various toxic esters (e.g., cocaine), and acts as a potent scavenger.

Organophosphates (OP) are toxic chemical compounds which are present in pesticides and chemical warfare agents. OPs produce their toxic effects by irreversibly inhibiting acetylcholinesterase, the enzyme that breaks down the neurotransmitter acetylcholine (Taylor P (1990) Anticholinesterase agents, in The Pharmacological Basis of Therapeutics (Gilman AG, Rall T W, Nies A S, and Taylor P eds) pp 131-149, Macmillan, New York. 1990). The accumulation of acetylcholine in response to OP exposure causes an overstimulation of cholinergic receptors at the neuromuscular junctions and nerve synapses (Marrs, T C, et al., (1996) Riot-control Agents, in Chemical Warfare Agents: Toxicology and Treatment, pp 221-230, John Wiley, Chichester 1996), which can lead to muscle weakness, increased secretions, respiratory depression, seizures, coma, and ultimately death resulting from respiratory and/or cardiovascular failure or convulsions. One approach to treating OP poisoning is the use of enzymes to sequester these compounds in the circulation before they reach their physiological target, acetylcholinesterase in the nervous system. Among these enzymes is plasma-derived human butyrylcholinesterase (Hu BChE; EC 3.8.1.1; accession no. M16541). BChE is mostly a tetrameric glycoprotein consisting of four identical subunits with a combined molecular mass of 340 kDa. The molecular mass of each subunit is 85 kDa, of which 65 kDa is protein and 20 kDa (24-26%) is carbohydrate.

Major limitations prohibiting the development of purified hBChE as a mainstream biologic drug include: limited availability of human plasma, limited scalability of manufacturing, high cost of purified human-derived product, and the need for intravenous administration. In addition, the preventive uses of hBChE are limited by its relatively short half-life. See, e.g., M. Wandhammer et al, Chem Biol Interact. 2013 Mar. 25; 203(1):19-23. doi: 10.1016/j.cbi.2012.08.005. Epub 2012 Aug. 16.

In an attempt to address some of these limitations, several methods for the production of recombinant hBChE in vitro (cell lines) and in vivo (transgenic animals, plants) were developed. However, the resulting recombinant proteins presented with unfavorable pharmacokinetic profiles making them unsuitable for preventive uses. Alternatively, adenovirus-mediated delivery of hBChE delivers suitable levels of the enzyme. See, e.g., Chilukuri N., et al., Chem Biol Interact. 2008 Sep. 25; 175(1-3):327-31. doi: 10.1016/j.cbi.2008.04.009. Epub 2008 May 21; and Chilukuri N., et al., Mol Pharmacol. 2009 September; 76(3):612-7. doi: 10.1124/mol.109.055665. Epub 2009 Jun. 19. However, adenovirus is not a candidate for development due to the inherent immunogenicity of the vector. Expression of hBChE peaks at around 4 days post IV administration of the adenoviral vector, and the peak is followed by a rapid decline, with minimal expression being detectable 10 days post-administration. See, Chilukuri (2008), (2009) cited above.

What are needed are safe and effective means for delivering therapeutically and/or prophylactically effective levels of hBChE.

SUMMARY OF THE INVENTION

In one aspect, a replication-defective, recombinant AAV (rAAV) which comprises an AAV capsid having a vector genome packaged therein. The vector genome comprises: AAV inverted terminal repeats (ITRs); a promoter; a 5' UTR; a leader sequence operably linked to a codon optimized human butyrylcholinesterase (hBChE); a linker; a nucleic acid sequence encoding a proline rich peptide, optionally having an exogenous leader sequence; and a polyA.

In a further aspect, an aqueous liquid suspension comprising an rAAV as described herein and an aqueous suspension base is provided herein.

In another aspect, an rAAV or a liquid suspension containing same, as described herein is provided which is administrable to a patient for protection against poisoning with organophosphate chemical agents, reducing the effects of organophosphates in a patient, and/or treating cocaine and/or heroin toxicity or addiction.

In yet another aspect, use of an rAAV in preparing a medicament is provided.

The medicament may be administrable to a patient for protection against poisoning with organophosphate chemical agents, reducing the effects of organophosphates in a patient, and/or treating cocaine or heroin toxicity and/or addiction.

In still a further aspect, the invention provides a method for protecting against poisoning with organophosphate chemical agents. The method involves administering an rAAV.hBChE as provided herein.

In yet another aspect, a method for reducing the effects of organophosphates in a patient is provided. The method comprises administering an rAAV.hBChE as provided herein to the patient.

These and other aspects of the invention will be apparent from the following Description of the Invention.

BRIEF DESCRIPTION OF THE FIGURES

FIGS. 8C and 8D, UbC-cmyc-IL2-BChE C1-IRES-IL2-LPDN-SV40; FIGS. 8E and 8F, CB7-cmyc-IL2-BChE C1-IRES-IL2-PRIMA1-rBG; and FIGS. 8G and 8H, CB7-cmyc-IL2-BChE C1-IRES-IL2-LPDN-rBG). Mice were injected IM with one 30 μl injections into the left gastrocnemius muscles. Orbital bleeds were collected on different days as shown. Mice were administered with a dose of $1\times10^{11}$ GC titered by QPCR. Expression was measured in serum by ELISA and activity was measured by modified Ellman's method, values are expressed as mean±SD (n=5/group).

FIGS. 9C and 9D, CB7-cmyc-IL2-BChE C1-IRES-IL2-LPDN-rBG). Mice were injected IM with one 30 μl injections into the left gastrocnemius muscles. Orbital bleeds were collected on different days a shown. Mice were administered with a dose of $1\times10^{11}$ GC titered by QPCR. Expression was measured in serum by ELISA and activity was measured by modified Ellman's method, values are expressed as mean±SD (n=3/group).

FIGS. 9C and 9D, CB7-cmyc-IL2-BChE C1-IRES-IL2-LPDN-rBG). Mice were injected IM with one 30 μl injections into the left gastrocnemius muscles. Orbital bleeds were collected on different days a shown. Mice were administered with a dose of $1\times10^{11}$ GC titered by QPCR. Expression was measured in serum by ELISA and activity was measured by modified Ellman's method, values are expressed as mean±SD (n=3-5/group).

FIG. 10B, CB7-cmyc-IL2-BChE C1-IRES-IL2-LPDN-rBG). Mice were injected IM with one 30 μl injections into the left gastrocnemius muscles. Orbital bleeds were collected on different days a shown. Mice were administered with a dose of $1\times10^{11}$ GC titered by QPCR. Expression was measured in serum by ELISA. Values are expressed as mean±SD (n=3/group).

DETAILED DESCRIPTION OF THE INVENTION

Figure 1A:
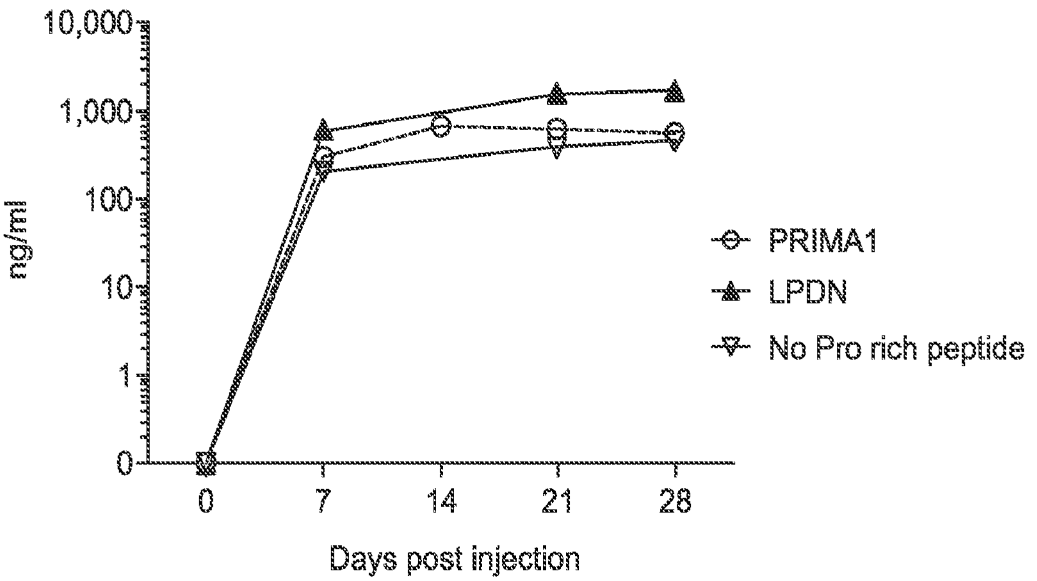
FIGS. 1A and 1B provide the effect of variable proline rich peptide (PRIMA1 PRP vs LPDN PRP) on BChE expression (FIG. 1A) and activity (FIG. 1B) post vector administration in RAG KO mice. Expression and activity of BChE C0 post-vector administration (in context of CMV promoter, PI intron, innate leader and SV40 polyA) in the presence (PRIMA1 PRP, circles vs LPDN PRP, triangles) or absence (inverted triangles) of proline rich peptide as shown. Mice were injected IM with one 30 μl injections into the left gastrocnemius muscles. Orbital bleeds were collected on different days as shown. Mice were administered with a dose of $1\times10^{11}$ GC tittered by QPCR. Expression was measured in serum by ELISA and activity was measured by modified Ellman's method, values are expressed as mean±SD (n=5/group).

Recombinant, replication-defective AAV vectors which express hBChE are provided herein. These vectors have several advantages over prior art approaches. More particularly, rAAV are substantially non-immunogenic, thus no rapid decline in hBChE levels is expected. For example, hBChE expression from the illustrative rAAV vectors provided herein has been observed for at least two months with no decline and is expected to last for several months to several years. Further, this approach is not reliant on hBChE protein purification and has the flexibility to deliver the product into liver, lung and muscle.

As used herein, organophosphates (OP) are esters of phosphoric acid and its derivatives, having the general structure shows below, with a central phosphorus atom (P) and a characteristic (P═O) or thiophosphoric (P═S) bond. The symbol X represents the leaving group which is replaced (by nucleophilic substitution) by the oxygen of serine in an acetylcholinesterase (AcHE) active site. The rate of AcHe inhibition depends on the leaving group; higher tendency of leaving results in higher affinity of the inhibitor to the enzyme.

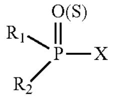

OP having toxicity include, e.g., chemical compounds used, e.g., as insecticides (malathion, parathion, diazinon, fenthion, dichlorvos, chlorpyrifos, ethion sulfoton, phorate, dimethoate, ciodrin, dichlorvos, dioxathion, ruelene, carbophenothion, supona, TEPP, EPN, HETP, parathion, malathion, ronnel, coumaphos, diazinon, trichlorfon, paraoxon, potasan, dimefox, mipafox, schradan, sevin, and dimetonor), nerve gases (soman, sarin, tabun, VX), ophthalmic agents (echothiophate, isoflurophate), and antihelmintics (trichlorfon). Herbicides (tribufos [DEF], merphos) are tricresyl phosphate-containing industrial chemicals.

The vectors provided herein are designed to carry a nucleic acid sequence which expresses at a minimum, leader sequences and the mature human butyrylcholinesterase enzyme. The wild-type human enzyme sequence (Human BChE, hBChE, hBuChE; UniProtKB-P06276) is reproduced in SEQ ID NO: 1, including the native leader (signal) peptide (amino acids residues 1 to 26) and the mature protein (amino acid residues 27 to 602). See, e.g., www.uniprot.org/uniprot/P06276. The nucleic acid sequence of the native human sequence (GenBank accession no. M16541.1) is reproduced in SEQ ID NO: 2. As discussed herein, while certain embodiments preferentially express the wild-type enzyme, there are indications wherein expression of hBChE mutants may be desired. In such embodiments, the vectors may be designed to express these hBChE mutants for a single therapy, or for use in a co-therapy with in combination with the vectors expressing the wild-type human enzyme, or in combination with another therapeutic. Similarly, vectors expressing the hBChE wild-type mutant [SEQ ID NO:2] may be used alone, or in a co-therapy with another therapeutic.

Native BChE is primarily a tetrameric glycoprotein consisting of four identical subunits (typically about 98% is tetrameric form, which tetramer consists of four identical subunits corresponding to the mature enzyme). As provided herein, the vector (e.g., rAAV) expressed synthetic hBChE may be present in any form which confer a desired biological activity including, e.g., as a monomer, dimer, tetramer or a combination of two or more thereof. A variety of suitable methods are available to determine BChE activity. For example, BChE activity may be determined with a modified Ellman method (Ellman, G L., et al, Biochem Pharmacol, 1961, 7:88-95 41) in 96-well plates as described in the examples herein. Units of activity are μmol of butyrylthiocholine hydrolyzed per minute.

The activity of the BChE enzyme expressed from the rAAV vector has a specific activity similar to wild-type. Normal circulating levels of BChE enzyme are in the range of about 1 μg/mL or less. In certain embodiments, expression levels of about 10% to about 120% higher than normal wild-type BChE enzyme levels, or about 25% to about 100%, or about 50% to 100%, or about 75% to about 100%, or about 80% to about 100%, or about 90% to 95% of wild-type levels (delivered in protein form). In such embodiments, a patient may have a disorder or disease state associated with defective or null expression of the normal wild-type BChE enzyme. For example, the K variant of BChE enzyme (point mutation nt1615 GCA→ACA resulting in the amino acid change Ala539→Thr) has been associated with Alzheimer's disease and risk of cerebral amyloid angiopathy. In another example, patients homozygous for the A variant (point mutation at nt 209 GAT→GGT) resulting in an amino acid change Asp70→Gly), have been associated with sensitivity to mivacurium (used, e.g., as a muscle relaxant). In another example, mutant alleles at the BChE locus are associated with suxamethonium sensitivity (which is used, e.g., in surgical anesthesia) and increased risk for cocaine dependence and for crack cocaine use.

In certain embodiments, delivery of "normal" hBCheE activity levels about 5% to about 120% of the activity levels of human subjects may be therapeutically useful. Such embodiments may include, e.g., treatment of Alzheimer's disease and/or anesthesia sensitivity.

In certain other embodiments, e.g, to achieve protection against a chemical warfare agent containing an organophosphate or treatment of drug dependence, expression of human BChE at least 100 fold higher levels than normal levels are desirable, e.g., about 100 μg/mL to about 700 μg/mL (i.e., 100,000 ng/mL to 700,000 ng/mL), or higher. For example, expression may be at least 250 μg/mL, at least about 400 μg/mL, or at least about 600 μg/mL. Suitably, expression may be observed to be sustained above a threshold amount of at least 100 μg/mL within about 24 hours and may increase to reach a steady state over a period of several days to about three weeks. In a particularly desirable embodiment, these expression levels can be provided by the vector via intramuscular dosing of vector, which is a route which typically provides lower expression levels than intravenous dosing. However, other routes of administration are permitted, including inhalation, intravenous, among others discussed herein.

In certain embodiments, BChE mutants which provide enhanced cocaine hydrolysis activity as compared to the native human BChE may be selected. Native human BChE has been reported to slowly hydrolyze cocaine with a biomolecular constant rate (kcat/Km) of about 0.28 $mM^{-1}/min^{-1}$. See, e.g., P Masson and D Rochu, Acta Nature, 2009 April; 1(1): 68-79. Such mutants may include, A328Y (reported to have 4-fold higher catalytic efficiency), A328W/Y332A (reported to have a higher kcat/Dm activity), a 4-amino acid mutant A199S/S287G/A328W/Y332G (reported to provide an enzyme with a catalytic efficiency 456-fold greater than that of wild-type BChE) and a 5-amino acid mutant A199S/F227A/S287G/A328W/Y332G. In another embodiment, a mutant G117H and a double mutant G117H, E197Q are provided, which are capable of hydrolyzing toxic compounds including, e.g., paraoxon, sarin, echotiophate and VX. See, also, M. Dwyer et al, Biochemistry, 2014, Jul. 15: 453(27): 4476-4487, describing variants having Y332S, D340H, and Y332/S/D340H. These mutations are suited for use in the rAAV vectors described herein, e.g., when the function of human BChE for hydrolyzing ester-containing therapeutic and/or addictive drugs such as succinylcholine and its long-chain derivatives aspirin, irinotecan, heroin is desired and/or the function of BChE in plasma for hydrolyzing prodrugs such as isosorbide diaspirinate, bambuterol, ISDA, and/or cocaine is desired. When treating a subject having addiction or overdose (poisoning) of drugs such as cocaine, having the properties described above, the AAV.hBChE desirably is delivered in an amount which expresses about 100 fold to 1000 fold higher levels, or 500 to about 750 fold higher levels of human BChE than the "normal" about 1 μg/mL levels found in humans. For example, a suitable dose of vector may provide expression of about 1 mg/mL to about 10 mg/mL of hBCheE. However, higher or lower amounts may also provide a therapeutic effect alone, or when delivered as in a combination therapy, or as a co-therapy.

In certain embodiments, the hBChE coding sequence is modified to have a heterologous leader sequence, e.g., a leader sequence derived a source different from the native (innate) hBCheE leader sequence. In one embodiment, the leader sequence is a human IL2 leader sequence, which is reproduced in SEQ ID NO: 20. In a further embodiment, the leader sequence is a mutated human IL2 leader sequence, which is reproduced in SEQ ID NO: 21.

In one aspect, an engineered nucleic acid sequence encoding hBChE is provided. In one embodiment, the hBChE is the sequence of hBChEC2, which is provided in SEQ ID NO: 6, shown with an IL2 leader sequence. In one embodiment, the hBChE coding sequence is hBChE CO with innate leader sequence, SEQ ID NO: 3. In one embodiment, the hBChE coding sequence is hBChE CO with an IL2 leader sequence, SEQ ID NO: 4. In one embodiment, the hBChE coding sequence is hBChE C1 with an IL2 leader sequence, SEQ ID NO: 5. In one embodiment, the hBChE coding sequence is hBChE C3 with an IL2 leader sequence, SEQ ID NO: 7. In one embodiment, the hBChE coding sequence is hBChE C4 with an IL2 leader sequence, SEQ ID NO: 8.

In certain embodiments, a vector is provided which contains a nucleic acid sequence encoding a 57 nt IL2 signal peptide and the mature hBChE enzyme. In one embodiment, the hBChE coding sequence is hBChE CO with IL2 leader sequence, which is reproduced in SEQ ID NO: 4. In one embodiment, the codon optimized hBChE coding sequence is hBChE C1 with IL2 leader sequence, which is reproduced in SEQ ID NO: 5. In one embodiment, the hBChE coding sequence is hBChE C2 with IL2 leader sequence, which is reproduced in SEQ ID NO: 6. In one embodiment, the codon optimized hBChE coding sequence is hBChE C3 with IL2 leader sequence, which is reproduced in SEQ ID NO: 7. In one embodiment, the codon optimized hBChE coding sequence is hBChE C4 with IL2 leader sequence, which is reproduced in SEQ ID NO: 8. In one embodiment, the codon optimized hBChE coding sequence is hBChE C5 with IL2 leader sequence, which is reproduced in SEQ ID NO: 9. In one embodiment, the codon optimized hBChE coding sequence is hBChE C6 with IL2 leader sequence, which is reproduced in SEQ ID NO: 10. In one embodiment, the codon optimized hBChE coding sequence is hBChE C7 with IL2 leader sequence, which is reproduced in SEQ ID NO: 11. In one embodiment, the codon optimized hBChE coding sequence is hBChE C8 with IL2 leader sequence, which is reproduced in SEQ ID NO: 12. In one embodiment, the codon optimized hBChE coding sequence is hBChE with mutation G117H E197Q with IL2 leader sequence, which is reproduced in SEQ ID NO: 13.

The following nomenclature for the hBChE coding sequences provided herein are used interchangeably.

| hBChE Coding Sequences | Alternative hBChE Coding Sequence Nomenclature |
|---|---|
| hBChE C0 | hBChE3 |
| hBChE C1 | hBChE2 |
| hBChE C2 | BuChE Ia |
| hBChE C3 | hBChE4 |
| hBChE C4 | hBChEeb |
| hBChE C5 | BuChE ec |
| hBChE C6 | hBChE1 |
| hBChE C7 | BChEst |
| hBChE C8 | hBChE5 |

In certain embodiments, the hBChE is co-expressed from the viral vector with a proline-rich peptide (PRP). Such PRP are derived from a sequence having the proline-rich core sequence: PSPPLPPPPPPPPPPPPPPPPPPPPPLP (SEQ ID NO: 41) by vary in length at their N- and C-terminals. PRP do not contain native leader sequences. However, for use in the vector genomes herein, the PRP are provided with a leader sequence in order to direct it to the same intracellular location as the hBChE in order to enhance tetramerization. In another embodiment, the proline-rich peptide is derived from human Proline-rich membrane anchor 1 (PRIMA1, UniProtKB-Q86XR5). In a further embodiment, the proline-rich peptide is derived from human lamellipodin (LPDN, UniProtKB-Q70E73). In one embodiment, the amino acid sequence of hPRIMA1 PRP is that of SEQ ID NO: 48. In a further embodiment, the coding sequence encoding hPRIMA1 PRP with an IL2 leader is reproduced in SEQ ID NO: 23. In another embodiment, the amino acid sequence of hLPDN PRP is that of SEQ ID NO: 49. In a further embodiment, the coding sequence encoding hLPDN PRP with an IL2 leader is reproduced in SEQ ID NO: 24. As used illustrated in the examples, a synthetic PRIMA1 construct is provided which includes the N-terminal IL2 signal peptide, followed by a proline-rich extracellular domain. In the examples herein, a transmembrane segment, and a cytoplasmic domain which are in the native protein are not present. The examples herein further demonstrate use of LPDN PRP or PRIMA1 PRP with an N-terminal IL-2 signal peptide. In certain embodiments, the vectors provided herein contain a heterologous signal peptide, e.g., an IL2 signal peptide. However, other signal peptides may be selected. In still other embodiments, variants on the lamellipodin, variants of the PRIMA1, or other proline-rich peptides may be selected.

Suitably, the hBChE and proline-rich peptide are co-expressed from a bicistronic expression cassette in which a linker sequence separates the two coding sequences in a manner which allow their expression to be driven by a single promoter. Suitable linkers, e.g., an IRES or F2A are discussed herein. In one embodiment, the linker is IRES with a sequence reproduced in SEQ ID NO: 22. In other embodiments, other multiple expression cassettes may be included in a vector.

Suitably, the expression cassette is designed so that a larger amount of BChE is expressed than PRP in accordance with the requirements for preferential BChE tetramer formation. In one embodiment, the ratio of BChE to PRP is at least 4 to 1; however, other ratios may be useful. For example, a greater excess of expressed BChE to PRP, e.g., ratios of 5-10 parts BChE: 1 PRP may be used. Still other ratios may be selected, e.g., 1:1.

While the present invention describes expression from an rAAV, these constructs may be engineered into other genetic elements (e.g., a plasmid useful in production or for direct delivery), or another viral vector.

These coding sequences and suitable viral vector elements are described in more detail below.

AAV Capsid

In the examples below, the vector is a recombinant, replication-defective adeno-associated virus.

In certain embodiments, the rAAV capsid is selected from amongst those having tropism for the liver. Any of a number of rAAV vectors with liver tropism can be used. Examples of AAV which may be selected as sources for capsids of rAAV include, e.g., rh10, AAVrh64R1, AAVrh64R2, rh8 [See, e.g., US Published Patent Application No. 2007-0036760-A1; US Published Patent Application No. 2009-0197338-A1; EP 1310571]. See also, WO 2003/042397 (AAV7 and other simian AAV), U.S. Pat. Nos. 7,790,449 and 7,282,199 (AAV8), WO 2005/033321 and U.S. Pat. No. 7,906,111 (AAV9), and WO 2006/110689], and rh10 [WO 2003/042397], AAV3B; AAVdj [US 2010/0047174]. As illustrated in the examples, an AAV8 capsid may be selected.

As used herein, "AAV8 capsid" refers to an assembled AAV8 capsid, which contains AAV vp1, vp2 and vp3 protein, having the encoded amino acid sequence of GenBank accession: YP_077180 (SEQ ID NO: 47), which is incorporated by reference herein. Some variation from this encoded sequence is encompassed herein, which may include sequences having about 99% identity to the referenced amino acid sequence in GenBank accession: YP_077180; U.S. Pat. Nos. 7,282,199, 7,790,449; 8,319,480; 8,962,330; U.S. Pat. No. 8,962,332, (i.e., less than about 1% variation from the referenced sequence). In another embodiment, the AAV8 capsid may have the VP1 sequence of the AAV8 variant described in WO2014/124282 or the dj sequence described in US 2013/0059732 A1 or U.S. Pat. No. 7588772 B2, which is incorporated by reference herein. Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003), US 2013/0045186A1, and WO 2014/124282.

In certain embodiments, an AAV capsid having tropism for muscle, and particularly, skeletal muscle may be selected. Such AAV may include, e.g., AAV8, AAV1, AAV6, amongst others. In certain embodiments, an AAV capsid having tropism for epithelial cells may be selected. Such AAV may include, e.g., AAV9, amongst others. In other embodiments, muscular tropism may not be as important a factor. In certain embodiments, intravenous delivery may be desired, e.g., for anesthesia sensitivity or drug addiction, as described herein. In still other embodiments, central nervous system tropism may be desired, e.g., for treatment of Alzheimer's Disease. Still other tropisms or routes of delivery may be selected.

Vector Genome Elements

A vector genome is designed which contains the expression cassette for the hBChE and protein-rich peptide. Suitably, such a genome includes AAV ITRs flanking a transgene expression cassette.

The AAV vector may contain a full-length AAV 5' inverted terminal repeat (ITR) and a full-length 3' ITR. A shortened version of the 5' ITR, termed ΔITR, has been described in which the D-sequence and terminal resolution site (trs) are deleted. The abbreviation "sc" refers to self-complementary. "Self-complementary AAV" refers a construct in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

Where a pseudotyped AAV is to be produced, the ITRs are selected from a source which differs from the AAV source of the capsid. For example, AAV2 ITRs may be selected for use with an AAV capsid having a particular efficiency for a selected cellular receptor, target tissue or viral target. In one embodiment, the ITR sequences from AAV2, or the deleted version thereof (ΔITR), are used for convenience and to accelerate regulatory approval. However, ITRs from other AAV sources may be selected. Where the source of the ITRs is from AAV2 and the AAV capsid is from another AAV source, the resulting vector may be termed pseudotyped. However, other sources of AAV ITRs may be utilized. In certain embodiment, the 5'ITR is that of SEQ ID NO: 28. In certain embodiment, the 3'ITR is that of SEQ ID NO: 29.

As used herein, an "expression cassette" refers to a nucleic acid sequence which comprises at least a first open reading frame (ORF) and optionally a second ORF. An expression cassette may be designed to be bicistronic, i.e., to contain regulatory sequences which direct expression of the ORFs thereon from shared regulatory sequences. In this instance, the two ORFs (e.g., hBChE and PRP) are typically separated by a linker. Suitable linkers, such as an internal ribozyme binding site (IRES) and/or a furin-2a self-cleaving peptide linker (F2a), [see, e.g., Radcliffe and Mitrophanous, Gene Therapy (2004), 11, 1673-1674] are known in the art. Suitably, the ORF are operably linked to regulatory control sequences which direct expression in a target cell. Such regulatory control sequences may include a polyA, a promoter, and an enhancer. In order to facilitate co-expression from an AAV vector, at least one of the enhancer and/or polyA sequence may be shared by the first and second expression cassettes.

As discussed above, the vector contains an expression cassette in which hBChE and PRP operably linked to regulatory sequences which direct expression thereof In certain embodiments, the PRP coding sequences include an artificial heterologous leader sequences to facilitate transport of the peptide to the same cellular compartment to which BChE is directed for more effective tetramer (dimer) assembly. In certain embodiments, the hBChE is also provided with a heterologous leader sequences.

These leader sequences may be selected from human leader sequences, e.g., interleukin 2 for the tissue to which the vector is to be targeted, e.g., liver (e.g., IL2), muscle, epithelium. These may be signal sequences from a cytokine (e.g., IL2, IL12, IL18, or the like), insulin, albumin, β-glucuronidase, alkaline protease or the fibronectin secretory signal peptides, mucin, amongst others. In certain embodiments, the PRP may be provided with a native hBChE leader sequence. See, e.g., www.signalpeptide.de [Signal Peptide Website: An information platform for Signal Sequences and Signal Peptides].

Suitable regulatory control sequences may be selected and obtained from a variety of sources. In one embodiment, a minimal promoter and/or a minimal polyA may be utilized to conserve size. The examples herein utilize CMV, or more preferably, UbC or CB7.

As used herein, the term "minimal promoter" means a short DNA sequence comprised of a TATA-box and other sequences that serve to specify the site of transcription initiation, to which regulatory elements are added for control of expression. In one embodiment, a promoter refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. In one embodiment, the minimal promoter is a Cytomegalovirus (CMV) minimal promoter. In another embodiment, the minimal promoter is derived from human CMV (hCMV) such as the hCMV immediate early promoter derived minimal promoter (see, US 20140127749, and Gossen and Bujard (Proc. Natl. Acad. Sci. USA, 1992, 89: 5547-5551), which are incorporated herein by reference). In another embodiment, the minimal promoter is derived from a viral source such as, for example: SV40 early or late promoters, cytomegalovirus (CMV) immediate early promoters, or Rous Sarcoma Virus (RSV) early promoters; or from eukaryotic cell promoters, for example, beta actin promoter (Ng, Nuc. Acid Res. 17:601-615, 1989; Quitsche et al., J. Biol. Chem. 264:9539-9545, 1989), GADPH promoter (Alexander, M. C. et al., Proc. Nat. Acad. Sci. USA 85:5092-5096, 1988, Ercolani, L. et al., J. Biol. Chem. 263:15335-15341, 1988), TK-1 (thymidine kinase) promoter, HSP (heat shock protein) promoters, UbB or UbC promoter, PGK, Ef1-alpha promoter or any eukaryotic promoter containing a TATA box (US Published Application No. 2014/0094392). In another embodiment, the minimal promoter includes a mini-promoter, such as the CLDNS mini-promoter described in US Published Application No. 2014/0065666. In another embodiment, the minimal promoter is the Thymidine Kinase (TK) promoter. In one embodiment, the minimal promoter is tissue specific, such as one of the muscle-cell specific promoters minimal TnISlow promoter, a minimal TnIFast promoter or a muscle creatine kinase promoter (US Published Application No. 2012/0282695). Each of these documents is incorporated herein by reference. In one embodiment, the promoter is a CMV promoter, which is reproduced in SEQ ID NO: 14. In one embodiment, the promoter is a CMV IE promoter, which is reproduced in SEQ ID NO: 15. In one embodiment, the promoter is a chicken beta actin (CB) promoter, which is reproduced in SEQ ID NO: 16. In one embodiment, the promoter is a UbC promoter, which is reproduced in SEQ ID NO: 18. In a further embodiment, a C4 enhancer which is reproduced in SEQ ID NO: 17, is further included in the expression cassette. In one embodiment, the promoter is a C4/UbC promoter, which is a CMV C4 enhancer in the upstream Pf-UbC promoter. In one embodiment, the promoter is a CB7 promoter, which is a hybrid between a cytomegalovirus (CMV) immediate early enhancer (C4) and the chicken beta actin promoter and intron. In a further embodiment, the promoter is a CB7 promoter, which is reproduced in SEQ ID NO: 50.

In one embodiment, the polyadenylation (poly(A)) signal is a minimal poly(A) signal, i.e., the minimum sequence required for efficient polyadenylation. In one embodiment, the minimal poly(A) is a synthetic poly(A), such as that described in Levitt et al, Genes Dev., 1989 July, 3(7):1019-25; and Xia et al, Nat Biotechnol. 2002 October; 20(10): 1006-10. Epub 2002 Sep. 16. Each of these documents is incorporated herein by reference. In another embodiment, the poly(A) is derived from the rabbit beta-globin poly(A). In a further embodiment, the poly(A) comprises the sequence reproduced in SEQ ID NO: 26. In one embodiment, the poly(A) is derived from the SV40 early poly A signal sequence. In a further embodiment, the poly(A) comprises the sequence reproduced in SEQ ID NO: 27.

In certain embodiments, the vector genome includes one or more of a 5' untranslated region (UTR), an intron, a Kozak sequence, and/or a 3' UTR. As used herein, a “5' UTR” is also known as a leader sequence or leader RNA. In the examples herein, the 5' UTR is derived from c-myc. In a further embodiment, the 5'UTR comprises the sequence reproduced in SEQ ID NO: 19. However, other suitable sources are known to those of skill in the art. See, e.g., www.utrdb.ba.itb.cnr.it [Institute for Biomedical Technologies, UTR database]. Optionally, a 3' UTR may also be derived from, e.g., c-myc, a woodchuck post-transcription regulatory element.

In certain embodiments, the expression cassette comprises: UbC-cmyc-IL2-BChE C1-IRES-IL2-PRIMA1 [nt 14 to nt 4162 of SEQ ID NO: 30]. In other embodiments, the expression cassette comprises: UbC-cmyc-IL2-BChE C1-IRES-IL2-LPDN [nt 14 to nt 4874 of SEQ ID NO: 31]. In other embodiments, the expression cassette is CB7-cmyc-IL2-BChE C1-IRES-IL2-PRIMA1 [SEQ ID NO: 32]. In still other embodiments, the expression cassette is: CB7-cmyc-IL2-BChE C1-IRES-IL2-LPDN [SEQ ID NO: 33]. In another embodiment, the expression cassette comprises C4/UbC-hIL2-BchE C1-IRES-LPDN [SEQ ID NO: 34]. In another embodiment, the expression cassette comprises C4/UbC-hIL2-BChE C1-IRES-PRIMA1 [SEQ ID NO: 35]. In yet another embodiment, the expression cassette comprises C4/UbC.hIL2.BChE C1.IRES.PRIMA.RBG [SEQ ID NO: 51]. Such expression cassettes may be particularly well suited for targeting liver and/or muscle.

The expression cassette is typically engineered into a suitable genetic element, e.g., a plasmid. For a vector genomes, the expression cassette is flanked by AAV ITRs.

Suitably, the plasmid may be used in production of rAAV vectors. Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003), US 2013/0045186A1, and WO 2014/124282. However, the hBChE coding sequences and the vector genomes may optionally be engineered into another suitable viral vector. See, e.g., WO 2014/168953, providing chimeric AAV/bocavirus parvovirus vectors. Still other viral systems may be selected.

Vector Manufacture

Numerous methods are known in the art for production of rAAV vectors, including transfection, stable cell line production, and infectious hybrid virus production systems which include Adenovirus-AAV hybrids, herpesvirus-AAV hybrids and baculovirus-AAV hybrids. See, e.g., G Ye, et al, Hu Gene Ther Clin Dev, 25: 212-217 (December 2014); R M Kotin, Hu Mol Genet, 2011, Vol. 20, Rev Issue 1, R2-R6; M. Mietzsch, et al, Hum Gene Therapy, 25: 212-222 (March 2014); T Virag et al, Hu Gene Therapy, 20: 807-817 (August 2009); N. Clement et al, Hum Gene Therapy, 20: 796-806 (August 2009); D L Thomas et al, Hum Gene Ther, 20: 861-870 (August 2009). rAAV production cultures for the production of rAAV virus particles may require; 1) suitable host cells, including, for example, human-derived cell lines such as HeLa, A549, or 293 cells, or insect-derived cell lines such as SF-9, in the case of baculovirus production systems; 2) suitable helper virus function, provided by wild type or mutant adenovirus (such as temperature sensitive adenovirus), herpes virus, baculovirus, or a nucleic acid construct providing helper functions in trans or in cis; 3) functional AAV rep genes, functional cap genes and gene products; 4) a transgene (such as a therapeutic transgene) flanked by AAV ITR sequences; and 5) suitable media and media components to support rAAV production.

A variety of suitable cells and cell lines have been described for use in production of AAV. The cell itself may be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, BHK, MDCK, COS 1, COS 7, BSC 1, BSC 40, BMT 10, VERO, WI38, HeLa, a HEK 293 cell (which express functional adenoviral E1), Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc.

AAV sequences may be obtained from a variety of sources. For example, a suitable AAV sequence may be obtained as described in WO 2005/033321 or from known sources, e.g., the American Type Culture Collection, or a variety of academic vector core facilities. Alternatively, suitable sequences are synthetically generated using known techniques with reference to published sequences. Examples of suitable AAV sequences are provided herein.

In addition to the expression cassette, the cell contains the sequences which drive expression of an AAV capsid in the cell (cap sequences) and rep sequences of the same source as the source of the AAV ITRs found in the expression cassette, or a cross-complementing source. The AAV cap and rep sequences may be independently selected from different AAV parental sequences and be introduced into the host cell in a suitable manner known to one in the art. While the full-length rep gene may be utilized, it has been found that smaller fragments thereof, i.e., the rep78/68 and the rep52/40 are sufficient to permit replication and packaging of the AAV.

In one embodiment, the host cell contains at least the minimum adenovirus DNA sequences necessary to express an Ela gene product, an E1b gene product, an E2a gene product, and/or an E4 ORF6 gene product. In embodiments in which the host cell carries only E1, the E2a gene product and/or E4 ORF6 gene product may be introduced via helper plasmid or by adenovirus co-infection. In another embodiment, the E2a gene product and/or E4 ORF6 may be substituted by herpesvirus helper functions. The host cell may contain other adenoviral genes such as VAI RNA, but these genes are not required. In one embodiment, the cell used does not carry any adenovirus gene other than E1, E2a and/or E4 ORF6; does not contain any other virus gene which could result in homologous recombination of a contaminating virus during the production of rAAV; and it is capable of infection or transfection by DNA and expresses the transfected gene (s).

One cell type useful in the methods and systems described herein is a host cell stably transformed with the sequences encoding rep and cap, and which is transfected with the adenovirus E1, E2a, and E4ORF6 DNA and a construct carrying the expression cassette as described above. Stable rep and/or cap expressing cell lines, such as B-50 (International Patent Application Publication No. WO 99/15685), or those described in U.S. Pat. No. 5,658,785, may also be similarly employed. Another desirable host cell contains the minimum adenoviral DNA which is sufficient to express E4 ORF6. Yet other cell lines can be constructed using the novel modified cap sequences.

The preparation of a host cell involves techniques such as assembly of selected DNA sequences. This assembly may be accomplished utilizing conventional techniques. Such techniques include cDNA and genomic cloning, which are well known and are described in Sambrook et al., Molecular Cloning: A Laboratory Manual, Cold Spring Harbor Press, Cold Spring Harbor, N.Y., including polymerase chain reaction, synthetic methods, and any other suitable methods which provide the desired nucleotide sequence.

The required components for AAV production (e.g., adenovirus E1a, E1b, E2a, and/or E4ORF6 gene products, rep or a fragment(s) thereof, cap, the expression cassette, as well as any other desired helper functions), may be delivered to the packaging host cell separately, or in combination, in the form of any genetic element which transfer the sequences carried thereon.

Alternatively, one or more of the components required to be cultured in the host cell to package an expression cassette in an AAV capsid may be provided to the host cell in trans using a suitable genetic element.

Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), custom formulations such as those described in U.S. Pat. No. 6,566,118, and Sf-900 II SFM media as described in U.S. Pat. No. 6,723,551, each of which is incorporated herein by reference in its entirety, particularly with respect to custom media formulations for use in production of recombinant AAV vectors.

rAAV production culture media may be supplemented with serum or serum-derived recombinant proteins at a level of 0.5%-20% (v/v or w/v). Alternatively, as is known in the art, rAAV vectors may be produced in serum-free conditions which may also be referred to as media with no animal-derived products. One of ordinary skill in the art may appreciate that commercial or custom media designed to support production of rAAV vectors may also be supplemented with one or more cell culture components know in the art, including without limitation glucose, vitamins, amino acids, and or growth factors, in order to increase the titer of rAAV in production cultures.

rAAV production cultures can be grown under a variety of conditions (over a wide temperature range, for varying lengths of time, and the like) suitable to the particular host cell being utilized. As is known in the art, rAAV production cultures include attachment-dependent cultures which can be cultured in suitable attachment-dependent vessels such as, for example, roller bottles, hollow fiber filters, microcarriers, and packed-bed or fluidized-bed bioreactors. rAAV vector production cultures may also include suspension-adapted host cells such as HeLa, 293, and SF-9 cells which can be cultured in a variety of ways including, for example, spinner flasks, stirred tank bioreactors, and disposable systems such as the Wave bag system.

rAAV vector particles may be harvested from rAAV production cultures by lysis of the host cells of the production culture or by harvest of the spent media from the production culture, provided the cells are cultured under conditions known in the art to cause release of rAAV particles into the media from intact cells, as described more fully in U.S. Pat. No. 6,566,118). Suitable methods of lysing cells are also known in the art and include for example multiple freeze/thaw cycles, sonication, microfluidization, and treatment with chemicals, such as detergents and/or proteases.

In order to ensure that empty capsids are removed from the dose of AAV.hBChE that is administered to patients, empty capsids are separated from vector particles during the vector purification process, e.g., using cesium chloride gradient ultracentrifugation. In one embodiment, the vector particles containing packaged genomes are purified from empty capsids using the process described in U.S. Patent Appln No. 62/266,341, filed on Dec. 11, 2015, and entitled "Scalable Purification Method for AAV8"; and PCT Application No. PCT/US16/65976, filed Dec. 9, 2016, which are incorporated by reference herein. Briefly, a two-step purification scheme is described which selectively captures and isolates the genome-containing rAAV vector particles from the clarified, concentrated supernatant of a rAAV production cell culture. The process utilizes an affinity capture method performed at a high salt concentration followed by an anion exchange resin method performed at high pH to provide rAAV vector particles which are substantially free of rAAV intermediates.

In one embodiment, the pH used is from 10 to 10.4 (about 10.2) and the rAAV particles are at least about 50% to about 90% purified from AAV8 intermediates, or a pH of 10.2 and about 90% to about 99% purified from AAV8 intermediates. In one embodiment, this is determined by genome copies. A stock or preparation of rAAV8 particles (packaged genomes) is "substantially free" of AAV empty capsids (and other intermediates) when the rAAV8 particles in the stock are at least about 75% to about 100%, at least about 80%, at least about 85%, at least about 90%, at least about 95%, or at least 99% of the rAAV8 in the stock and "empty capsids" are less than about 1%, less than about 5%, less than about 10%, less than about 15% of the rAAV8 in the stock or preparation.

In one embodiment, the formulation is be characterized by an rAAV stock having a ratio of "empty" to "full" of 1 or less, preferably less than 0.75, more preferably, 0.5, preferably less than 0.3.

In a further embodiment, the average yield of rAAV particles is at least about 70%. This may be calculated by determining titer (genome copies) in the mixture loaded onto the column and the amount presence in the final elutions. Further, these may be determined based on q-PCR analysis and/or SDS-PAGE techniques such as those described herein or those which have been described in the art.

For example, to calculate empty and full particle content, VP3 band volumes for a selected sample (e.g., an iodixanol gradient-purified preparation where numbers of GC equals numbers of particles) are plotted against GC particles loaded. The resulting linear equation (y=mx+c) is used to calculate the number of particles in the band volumes of the test article peaks. The number of particles (pt) per 20 μL loaded is then multiplied by 50 to give particles (pt) /mL. Pt/mL divided by GC/mL gives the ratio of particles to genome copies (pt/GC). Pt/mL-GC/mL gives empty pt/mL. Empty pt/mL divided by pt/mL and ×100 gives the percentage of empty particles.

Generally, methods for assaying for empty capsids and AAV vector particles with packaged genomes have been known in the art. See, e.g., Grimm et al., Gene Therapy (1999) 6:1322-1330; and Sommer et al., Molec. Ther. (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., J. Virol. (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacrylamide gels (e.g., Novex). Silver staining may be performed using SilverXpress (Invitrogen, CA) according to the manufacturer's instructions. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is provided herein which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April; 25(2):115-25. doi: 10.1089/hgtb.2013.131. Epub 2014 Feb. 14.

Formulations

The rAAV and other constructs described herein may be used in preparing a medicament for delivering an hBChE to a subject. Typically, such a medicament is a suspension containing the viral vector carrying, the hBChE enzyme coding sequences (e.g., an rAAV.hBChE). Such a replication-defective rAAV includes the vector having an AAV capsid as described herein and a vector genome packaged therein. The vector genome preferably contains an AAV 5' ITR, a promoter, a 5' UTR, a leader sequence operably linked to a hBChE coding sequence, a linker, a leader sequence operably linked to a codon optimized nucleic acid sequence encoding a proline rich peptide, an optional 3'UTR, a polyA, and an AAV3' ITR. Examples of suitable hBChE coding sequences include those of SEQ ID NOs: 3, 4, 5, 6, 7, 8, 9, 10, 11, 12 or 13. Examples of suitable vector genomes include those of C4/UhC-hIL2-BchE C1-IRES-LPDN [SEQ ID NO: 34], UbC-cmyc-IL2-BChE C1-IRES-IL2-PRIMA1 [nt 14 to nt 4162 of SEQ ID NO: 30]: UbC-cmyc-IL2-BChE C1-IRES-IL2-LPDN [nt 14 to nt 4874 of SEQ ID NO: 31]; CB7-cmyc-IL2-BChE C1-IRES-IL2-PRIMA1 [SEQ ID NO: 32]; CB7-cmyc-IL2-BChE C1-IRES-IL2-LPDN [SEQ ID NO: 33]; or C4/UbC-hIL2-BChE C1-IRES-PRIMA1 [SEQ ID NO: 35].

The rAAV.hBChE compositions can be formulated in dosage units to contain an amount of replication-defective virus that is in the range of about $1.0\times10^9$ GC to about $1.0\times10^{15}$ GC. In certain embodiments, this amount of viral genome may be delivered in multiple injections. Doses will vary based on the indication being treated and may also vary based on the route of delivery. For example, intravenous delivery may provide higher expression levels than intramuscular delivery routes; thus, a formulation for intravenous delivery may require a lower amount of rAAV.hBChE. In one embodiment, the dosage is about $1\times10^{11}$ GC to about $5\times10^{13}$ GC. In one embodiment, the dosage is about $1\times10^{12}$ GC to about $1\times10^{14}$ GC for an average In one embodiment, the dosage is about $1\times10^{11}$ GC to $1\times10^{14}$ GC for a subject. In another embodiment, the dose about $1\times10^{13}$ GC. For example, the dose of AAV virus may be about $1\times10^{12}$ GC, about $5\times10^{12}$ GC, about $1\times10^{13}$ GC, about $5\times10^{13}$ GC, or about $1\times10^{14}$ GC. In another example, the rAAV.hBChE may be delivered in an amount of about 0.001 mg to about 10 mg per mL. As used herein, the term "dosage" can refer to the total dosage delivered to the subject in the course of treatment, or the amount delivered in a single (or multiple) administration.

The above-described recombinant vectors may be delivered to host cells according to published methods. The rAAV, preferably suspended in a physiologically compatible carrier, may be administered to a desired subject including without limitation, a cat, dog, or other non-human mammalian subject. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and/or variants and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAV, preferably suspended in a physiologically compatible carrier, may be administered to a human or non-human mammalian patient. Suitable carriers may be readily selected by one of skill in the art in view of the indication for which the transfer virus is directed. For example, one suitable carrier includes an aqueous suspension base, e.g., saline, which may be formulated with a variety of buffering solutions (e.g., phosphate buffered saline). Other exemplary carriers include sterile saline, lactose, sucrose, maltose, and water. The selection of the carrier is not a limitation of the present invention. Optionally, the compositions of the invention may contain, in addition to the rAAV and carrier(s), other conventional pharmaceutical ingredients, such as preservatives, or chemical stabilizers.

Any suitable method or route can be used to administer AAV-containing compositions as described herein, and optionally, to co-administer other active drugs or therapies in conjunction with the AAV-mediated antibodies described herein. Routes of administration include, for example, systemic, oral, intravenous, intraperitoneal, subcutaneous, or intramuscular administration.

For administration by inhalation, the vectors are delivered in the form of an aerosol spray from a pressurized container or dispenser that contains a suitable propellant, e.g., a gas such as carbon dioxide or a nebulizer.

The compounds also can be prepared in the form of suppositories (e.g., with conventional suppository bases such as cocoa butter and other glycerides) or retention enemas for rectal delivery.

Uses

The rAAV provided herein will express a therapeutically effective amount of BChE polypeptide. The phrase “therapeutically effective amount” is used herein to mean an amount sufficient to reduce by at least about 15 percent, preferably by at least 50 percent, more preferably by at least 90 percent, and still more preferably prevent, a clinically significant deficit in the activity, function and response of the host. Alternatively, a therapeutically effective amount is sufficient to cause an improvement in a clinically significant condition in the host.

In certain embodiments, AAV-hBChE expresses at 100 units/ml of serum at 24 hours post vector administration into muscle, with steady-state expression levels of up to 30,000 units/ml of serum at 1 month. In other embodiments, steady-state expression levels are about 1000 units/mL to about 20,000 units/mL of serum at 1 month, or about 5000 units/mL to about 15,000 units/mL of serum at 1 month, or about 10,000 units/mL at 1 month.

In the context of detoxifying agents, often the level of effectiveness is defined in terms of protecting/scavenging/detoxifying a certain amount of toxic agent. A useful metric is LD50, which is the amount of chemical that is lethal to one half of the animals exposed to the chemical. Thus, a therapeutically effective amount also is one which is sufficient to protect at least 2× LD50 of toxic agent. In certain embodiments, the vector delivers amounts of detoxifying agent that protect against 5× and up to 50× or more during repeat exposures of LD50 of toxic agent.

In one aspect, a method for protecting against poisoning with organophosphate chemical agents is provided which involves administering an rAAV to the patient. In one embodiment, the rAAV is administered prior to exposure to the organophosphate. In certain embodiments, the rAAV is administered about 24 hours to 6 months, or about 3 days to 1 month, prior to exposure.

In certain embodiments, the compositions are administered intramuscularly. In other embodiments, the compositions are administered by inhalation. In still other embodiments, the compositions are administered for delivery to the liver. In yet further embodiments, the compositions are administered intravenously. Other suitable routes of delivery may be readily selected.

In one aspect, a method for protecting against poisoning with organophosphate chemical agents is provided which involves administering an rAAV to the patient.

In certain embodiments, the compositions are useful in a method for reducing the effects of organophosphates in a patient.

In still other embodiments, the compositions are useful in treating a patient with one or more of dementia, Alzheimer’s disease, pseudocholinesterase deficiency, cocaine addiction, chronic exposures to pesticides or insecticides, increased sensitivity to muscle relaxant drugs, complications during medical procedures requiring emergency treatments, prolonged recovery time due to paralyses and inability to breath, increased sensitivity to anesthetics, and/or increased sensitivity to environmental exposures.

In certain embodiments, the BChE enzyme expressed from the rAAV vector has an activity level within about 10% to about 500% of the activity of the wild-type BChE bioscavenger and/or enzyme activity, or about 25% to about 400%, or about 50% to 100%, or about 75% to about 100%, or about 80% to about 100%, or about 90% to 95% of wild-type levels (delivered in protein form).

In certain embodiments, the rAAV express BChE mutants which provide enhanced hydrolysis activity as compared to the native human BChE for certain toxic compounds, including e.g., heroin and/or cocaine. In another embodiment, a mutant is is used which has enhanced hydrolysis activity for certain toxic compounds including, e.g., paraoxon, sarin, echotiophate and VX. Thus, the rAAV.hBChE provided herein may be used to counteract addiction with certain toxic drugs, such heroin and/or cocaine.

The rAAV may be combined with other therapies which are the current state of the art treatment, but offer the advantage of reducing the amount of such treatment which is required and/or improving the patients’ condition beyond which can be achieved with such current therapies.

Optionally, an rAAV vector as described herein may be used in combination with pharmacologic agents. This may be particularly useful where the rAAV is administered post-OP exposure. Such agents may include e.g., atropine or pralidoxime, or combinations thereof. For atropine, one may start with a 1-2 mg IV bolus, repeat q3-5min pm for desire effects (drying of pulmonary secretions and adequate oxygenation). Each subsequent dose may be doubled for rapid control of patients in severe respiratory distress. An atropine drip titrated to the above endpoints can be initiated until the patient’s condition is stabilized.

Kits for Administering Vectors

Therapeutic kits are provided herein. Such kits will generally contain, in suitable container means, a pharmaceutically acceptable formulation of an rAAV vector as described herein in a form suitable for administration to a subject. The kits may also contain other pharmaceutically acceptable formulations, such as buffers for reconstitution, suspension or dilution, surfactants, or agents that adjust pH, improve suspension, or the like.

The kits may have a single container means that contains the expression construct in a form suitable for administration. Other kits of the present invention include the expression construct in a storage stable form, along with buffers or diluents in separate and distinct containers. For example, when the components of the kit are provided in one or more liquid solutions, the liquid solution is an aqueous solution, with a sterile aqueous solution being particularly preferred. However, the components of the kit may be provided as dried powder(s). When reagents or components are provided as a dry powder, the powder can be reconstituted by the addition of a suitable aqueous suspending agent. It is envisioned that the suspension agent may also be provided in another container means.

The container means of the kit may also include at least device for administration of the expression construct. For example, a syringe or inhaler may be included. In some embodiments, the expression construct may be pre-mixed and aliquoted into a unit dosage form and loaded into such a device. The kits may contain multiple devices for repeat administration or administration to more than one subject.

The kits may include a means for containing the vials, devices or such in close confinement for shipment, storage or commercial sale, such as, e.g., injection or blow-molded plastic containers into which the desired vials and other apparatus are placed and retained. The kits also may contain instructions for administration, including self-administration.

The terms "percent (%) identity", "sequence identity", "percent sequence identity", or "percent identical" in the context of amino acid sequences refers to the residues in the two sequences which are the same when aligned for correspondence. Percent identity may be readily determined for amino acid sequences over the full-length of a protein, polypeptide, about 32 amino acids, about 330 amino acids, or a peptide fragment thereof or the corresponding nucleic acid sequence coding sequencers. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the "Clustal Omega", "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

As used herein, the term "operably linked" refers to both expression control sequences that are contiguous with the gene of interest and expression control sequences that act in trans or at a distance to control the gene of interest.

A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As described above, the term "about" when used to modify a numerical value means a variation of ±10%, unless otherwise specified.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, 91%, 92%, 93%, 94%, 95%, 96%, 97%, 98%, 99%, or higher identity over a specified region (e.g., any one of the modified ORFs provided herein when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Generally, these programs are used at default settings, although one skilled in the art can alter these settings as needed. Alternatively, one of skill in the art can utilize another algorithm or computer program that provides at least the level of identity or alignment as that provided by the referenced algorithms and programs. This definition also refers to, or can be applied to, the compliment of a sequence. The definition also includes sequences that have deletions and/or additions, as well as those that have substitutions. As described below, the preferred algorithms can account for gaps and the like. Preferably, identity exists over a region that is at least about 25, 50, 75, 100, 150, 200 amino acids or nucleotides in length, and oftentimes over a region that is 225, 250, 300, 350, 400, 450, 500 amino acids or nucleotides in length or over the full-length of an amino acid or nucleic acid sequences.

Typically, when an alignment is prepared based upon an amino acid sequence, the alignment contains insertions and deletions which are so identified with respect to a reference AAV sequence and the numbering of the amino acid residues is based upon a reference scale provided for the alignment. However, any given AAV sequence may have fewer amino acid residues than the reference scale. In the present invention, when discussing the parental sequence, the term "the same position" or the "corresponding position" refers to the amino acid located at the same residue number in each of the sequences, with respect to the reference scale for the aligned sequences. However, when taken out of the alignment, each of the proteins may have these amino acids located at different residue numbers. Alignments are performed using any of a variety of publicly or commercially available Multiple Sequence Alignment Programs. Sequence alignment programs are available for amino acid sequences, e.g., the "Clustal Omega", "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, *Nucl. Acids. Res.*, "A comprehensive comparison of multiple sequence alignments", 27(13): 2682-2690 (1999).

Unless defined otherwise in this specification, technical and scientific terms used herein have the same meaning as commonly understood by one of ordinary skill in the art and by reference to published texts, which provide one skilled in the art with a general guide to many of the terms used in the present application.

The following examples are illustrative only and are not intended to limit the present invention.

EXAMPLES

As illustrated in the following studies, the approach provided herein achieved not only rapid onset of hBuChE expression in mice, but also sustainable, long-term expression for at least 2 months with no decline. AAV-hBChE expressed at over 100 ng/mL of serum at 24 hours post vector administration into mouse muscle, with steady-state expression levels of up to 300 ng/mL of serum at 1 month. Based on previous findings regarding required hBuChE levels, the levels of hBuChE expressed by the rAAV provided herein are expected to be protective in OP challenges. These compositions can be expanded to include populations that are occupationally exposed to pesticides. These compositions and methods may also be used for the delivery of other protective human enzymes, such as the use of rhodanase to protect against cyanides or glutathione against 2-chloro-acetophenone, which is present in tear gas and chemical mace.

BChE is one example of a human carbonic anhydrase (hCA) isoenzyme; others include hCA I, II, IX, and XII, AChE, LPO, and glutathione S-transferases (GST). GST (GST, EC 2.5.1.18) belong to the superfamily of phase II detoxification enzymes. They are multifunctional enzymes for the cellular defense against xeno-biotics and provide protection for organism. The subfamily of GSTs is further distinguished into at least 14 classes (a-,b-,d-,e-,z-,y-,k-,-, m-,-, s-,-,u-, and -GST). This classification is based on the substrate specificity, sensitivity to inhibitors, N-terminal amino acid sequence and antibody cross-reactivity. Each GST contains a G-site, which is the glutathione substrate binding site and an H-site, which is hydrophobic substrate binding site. The G-site is conserved in the N-terminal region among the different enzyme classes.

In one embodiment, the GST enzyme has the sequence shows in [GenBank AAA35934.1], reproduced in SEQ ID NO: 42. In another embodiment, the GST enzyme has the sequence [GenBank AAA70226.1], reproduced in SEQ ID NO: 43:

Rhodanese (also rhodanase, also thiosulfate sulfurtransferase) is a mitochondrial enzyme which detoxifies cyanide. See, R. Pallini et al, Biochem Biophys Res Commun, 180(2): 887-893 (1991 October) for the human sequence. In one embodiment, the enzyme has the sequence: [EC 2.8.1.1.1/GenBank BAA13327.1], which is reproduced in SEQ ID NO: 44. In another embodiment, the rhodanese enzyme has the sequence CAA42060.1, which is reproduced in SEQ ID NO: 45. In still another embodiment, the rhodanese enzyme has the sequence: UniProtKB/Swiss-Prot: P25325, which is reproduced in SEQ ID NO: 46.

Example 1

Mouse Models, Methods and Materials

A. Materials Used

BALB/c Male Rag and BChE knockout mice, 6-8 weeks old, were sourced from Jackson laboratories. For BChE activity assay DTNB and substrate S-Butyrylthiocholine iodide and other chemicals were procured from Sigma Aldrich. For BChE expression in serum, ELISA kit was procured from R&D systems. 4-12% precast native gel was purchased from Novex Wedge well. Rabbit poly clonal anti-BChE antibody was bought from Abcam (ab82307).

B. Vector Construction Strategy & Viral Production

All AAV8 vectors were sourced by the Penn Vector Core at the University of Pennsylvania as described previously (Gao G, et al. (2006) Biology of AAV serotype vectors in liver-directed gene transfer to nonhuman primates. Mol Ther 13: 77-87). Different open reading frames (ORFs) were designed. These were assessed with codon optimized BChE sequences. Also assessed were promoters (CMV, UbC, CB7 or C4/UbC), leader sequences from hIL2 and the innate BChE leader sequence, presence and absence of Proline rich peptide (PRIMAL LPDN, or no peptide), presence and absence of 5'UTR (c-myc), 3'UTR (WPRE, SEQ ID NO: 25) and polyA (RBG polyA or SV40 polyA). Different constructs were further packaged in the AAV8 viral capsid and titered later by Vector Core facility at University of Pennsylvania.

C. Animal Studies (Mice)

All mice were housed under controlled conditions in the animal facility of the Translational Research Laboratories at the University of Pennsylvania. Experimental protocols were approved by and performed in agreement with the guidelines of the IACUC (Institutional Animal Care and Use Committee) of the University of Pennsylvania. Each vector was diluted in sterile PBS into two doses, $1\times10^{10}$ and $1\times10^{11}$ (representing genome copies), each was injected into the left gastrocnemius muscle of five mice/experiment. Orbital bleeds were collected every 24 hours for the first three days and every week thereafter. Terminal cardiac bleeds were obtained upon termination of study on day 56. For challenge study, animals were challenged by providing a single dose of butyrylcholine (500 mg/kg i.p) to BChE WT, heterozygous (+/−), or KO mice (n=5/group), or BChE KO mice pre-treated with AAV.BChE vector via intramuscular injection. Mice were monitored for signs of toxicity (such as tonic-clonic convulsions, muscle fasciculation, body tremor, myoclonic jerks, piloerection, heaving respiration, lacrimation, and salivation) for 30 minutes following the challenge.

D. Sample Collection and Storage

Blood samples were obtained from animals via orbital bleeds and serum was separated by allowing sample to clot for 15 minutes before centrifuging in gel lock tubes for 5 minutes at 5000 rpm. Samples were then aliquoted into Eppendorf tube and stored at −20° C. Serum was also obtained from terminal cardiac bleeds upon termination of study.

E. Protein Expression

Butrylcholinestrase expression was quantified via commercially available Human BChE Quantikine ELISA kit. 100 μL Assay Diluent per well was added to plate 96 well polystyrene plate percolated with monoclonal antibody specific for human BChE. Samples and standard were diluted in Calibrator Diluent RDSP and 50 μL was transferred to the plate according to plate layout and incubated at room temp for two hours. Plates were then washed with wash Buffer 4 times, and 200 μL of human BChE conjugated HRP was added and incubated for two hours at room temperature. Plates were washed 4 times with wash buffer and 200 μL of substrate solution consisting of a 1:1 solution of stabilized hydrogen peroxide and stabilized tetramethylbenzidine was added. Plates were incubated at room temperature in the dark for 30 minutes and stop solution, 2 N sulfuric acid, was added. Absorbance was measured immediately within 30 minutes at 450 and 540 nm using Sepectramax M3 from Molecular Devices. Concentration of BChE in serum was determined by a linear regression curve from the standards via excel.

F. Enzymatic Activity Assay

Enzymatic activity of BChE was measured using a modified Ellman procedure [Ellman G. L, et al (1961) A new and rapid colorimetric determination of acetylcholinesterase activity. Biochem Pharmacol 7: 88-95]. Serum samples were diluted in 0.1 M pH 7.6 $NaPO_4$ buffer and 50 μL transferred to 96 well high binding polystyrene plates from Costar. Substrate was prepared by dissolving 5-Butyrylthiocholine Iodide in 0.1 M $NaPO_4$ buffer to concentration of 0.1 M and pH 7.5 and 101.3 μL was added to each well and incubated for 30 minutes at room temperature. Stop solution was prepared by dissolving DTNB in 0.1 M pH 7.6 $NaPO_4$ buffer and ethanol for 0.006 M concentration. 50 μL stop solution added per well and absorbance was measured immediately at 412 nm and 540 nm using Spectramax M3 plate reader. Optical imperfections of the plate were corrected for by subtracting the reading at 540 nm from the 412 nm read. Background was corrected for by using PBS as negative control in four duplicates on each plate; absorbance of this blank was averaged and subtracted from all samples.

Enzyme activity was calculated as the appearance of product (μM/min) using the Beer-Lambert equation. Absorbance reading from pre-injection serum was used as initial absorbance when calculating change in absorbance and reading from wells with sample was used as final absorbance. The coefficient of extinction used was 14500 $M^{-1}cm^{-1}$ and the length of path of light was 0.596 cm.

Figure 15:
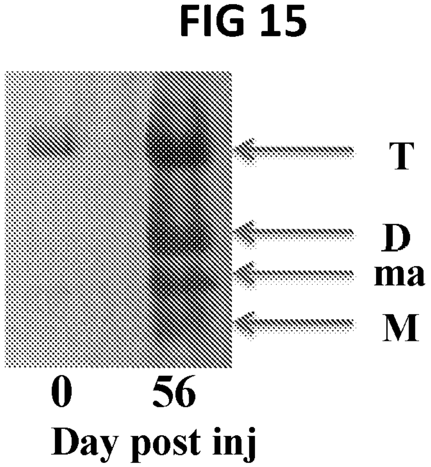
FIG. 15 provides a representative result of in-gel butyrylcholinesterase activity assay using serum collected on Day 0 and Day 56 from RAG KO mouse injected with $1\times10^{11}$ GC of AAV8.UbC.hIL2.BChE C1.IRES.PRIMA1.SV40 vector. Top band marked by letter T, tetramer; the band indicated by letter D, dimer; the band indicated by letter ma, one subunit of BChE and one of albumin; the band indicated by letter M, monomer.

G. Western Blot and in Gel Activity Assay:

1.5 μl of serum sample was diluted to 15 μl in native gel loading buffer and was passed through Novex WedgeWell 4-20% Tris-Glycine gel for 1.5 hours at 150 Volts at 4° C. Gel was rinsed with 0.1M Phosphate buffer pH 7.6. For butyrylcholinesterase activity assay, gel was stained with 2 mM butyrylthiocholine using Roots Karnovsky staining method. Butyrylthiocholine iodide was added to 0.1 M phosphate buffer pH 6.0 for final concentration of 2 mM Butyrylthiocholine iodide. The following were added to 32.5 mL of this solution in order with stirring in between: 0.5 mL 0.1 M sodium citrate, 1 mL 30 mM $CuSO_4$, 1 mL water, and 1 mL 5 mM potassium ferricyanide. Gel was incubated in this 50 mL solution at room temperature for 30 minutes (until brown precipitate formed in the gel). On the appearance of bands as shown, gel was washed with water and image was taken on ChemiDoc apparatus. A representative result is shown in FIG. 15.

For western blot, the native gel was blotted to PVDF membrane at 25 Volts 2.5 A for 16 minutes using Tras-blot Turbo from Biorad. The blot was blocked for 1 hour at room temperature in blocking buffer (TBS+0.3% Tween-20+5% (w/v) non-fat dry milk). The blot was incubated overnight with rabbit poly clonal anti-BChE antibody (1:100) at 4° C. in blocking buffer. Blot was further washed with TBS+0.3% Tween-20, 3 times 10 minutes each, and incubated with HRP conjugated goat anti-rabbit antibody in blocking buffer at RT for 1 hour (1:5000 dilution). Blot was further washed using same scheme and developed using the Pierce Chemilunilol Super Signal System as recommended. Image captured with ChemiDoc apparatus.

Example 2

Vector Optimization

A. Proline-Rich Peptide

To evaluate the effects of proline-rich peptide/domain on the expression of BChE using the viral vector deliver system in vivo, AAV.hBChE vectors in the absence or presence of IRES (SEQ ID NO: 22) followed by a proline-rich peptide of PRIMA1 (SEQ ID NO: 23) or LPDN (SEQ ID NO: 24) were constructed. The hBChE expression cassette described herein is a transgene flanked by inverted terminal repeats (ITRs). The transgene includes cytomegalovirus (CMV) promoter, a commercially available Promega® intron (PI), hBChE C0 with innate leader peptide (SEQ ID NO: 3) and an SV40 polyadenylation (polyA) signal. The IRES followed by PRP was inserted immediately after the hBChE coding sequence 0 (C0) if present. Different AAV.hBChE vector sequences were then packaged in the AAV8 viral capsid and further diluted in sterile PBS.

Figure 1B:
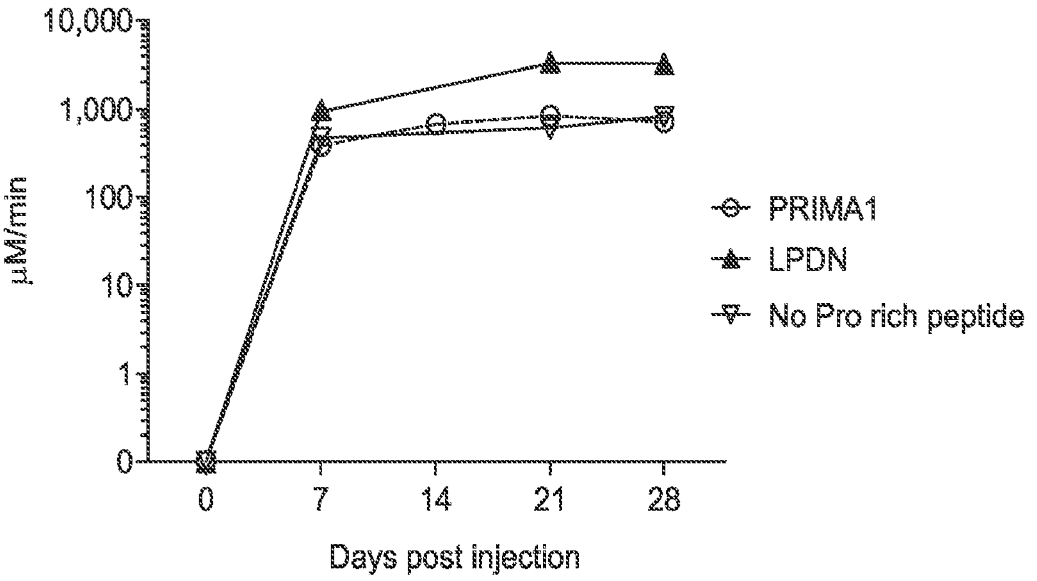

Studies were performed as described in Example 1. hBChE expressions and enzyme activity using the vectors described herein were assessed and the results were plotted in FIG. 1A and FIG. 1B respectively. The hBChE vector co-expressed with the PRIMA1 PRP demonstrated an increase in hBChE expression from Day 7 to Day 28 post injection during the observation period (FIG. 1A) as well as an increase in enzyme activity starting Day 7 (FIG. 1B) compared to the hBChE only vector. The hBChE vector co-expressed with the LPDN PRP also showed an increase in hBChE expression on Day 14 post injection compared to the hBChE only vector (FIG. 1A), however, no obvious change in enzyme activity was observed. These result indicates that co-expression with PRP, especially PRIMA1 PRP, benefit expression and enzyme activity in vivo.

B. 5'UTR

To evaluate the effects of 5'UTR on the expression of BChE using the viral vector deliver system in vivo, AAV.hBChE vectors in the presence or absence of c-myc (SEQ ID NO: 19) were constructed. The hBChE expression cassette described herein is a transgene flanked by inverted terminal repeats (ITRs). The transgene includes cytomegalovirus (CMV) promoter, a commercially available Promega® intron (PI), hBChE C0 with IL2 leader peptide (SEQ ID NO: 4), IRES, PRIMA1 PRP and an SV40 polyadenylation (polyA) signal. c-myc was inserted between PRIMA1 PRP and SV40 polyA if present. Different AAV.hBChE vector sequences were then packaged in the AAV8 viral capsid and further diluted in sterile PBS.

Figure 2A:
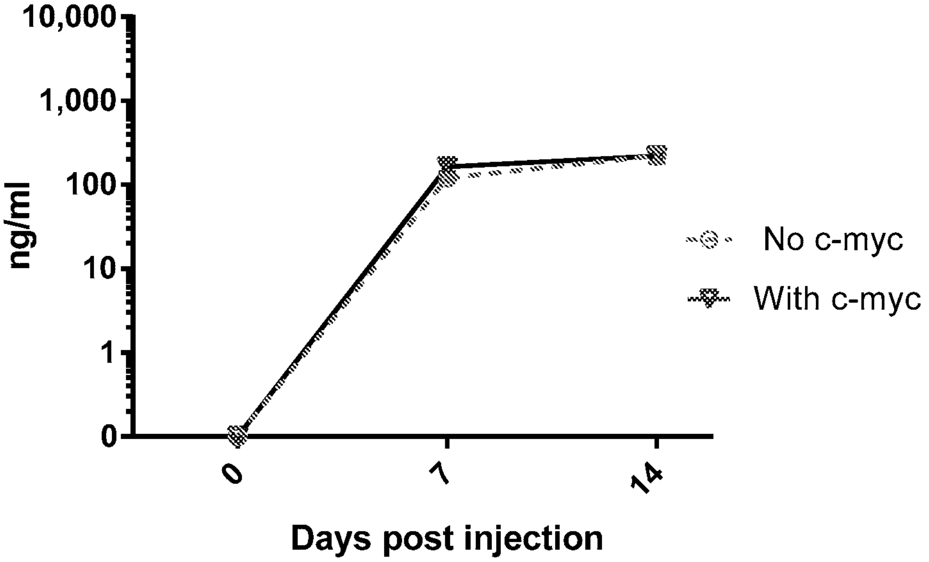
FIGS. 2A and 2B provide the effect of 5' UTR on BChE expression (FIG. 2A) and activity (FIG. 2B) post vector administration in RAG KO mice. Expression and activity of BChE CO post-vector administration (in context of CMV promoter, IL2 leader sequence, and PRIMA1 PRP) in the presence (inverted triangles connected via solid line) and absence (circles connected via dashed line) of c-myc 5'UTR. Mice were injected IM with one 30 μl injection into the left gastrocnemius muscles. Orbital bleeds were collected on different days as shown. Mice were administered with a dose of $1\times10^{11}$ GC tittered by QPCR. Expression was measured in serum by ELISA and activity was measured by modified Ellman's method, values are expressed as mean±SD (n=5/group).
Figure 2B:
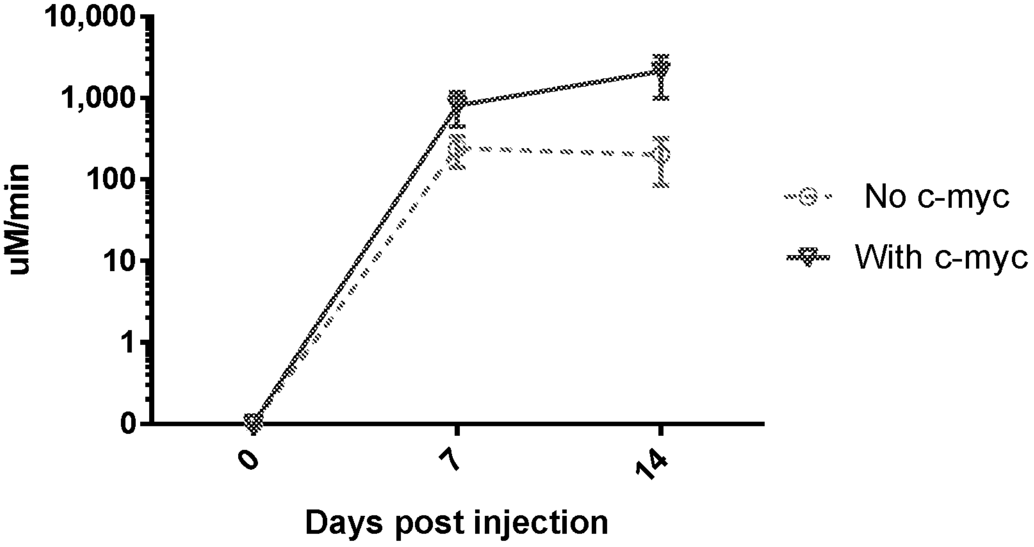

Studies were performed as described in Example 1. hBChE expressions and enzyme activity using the vectors described herein were assessed and the results were plotted in FIG. 2A and FIG. 2B respectively. Although no difference in expression of hBChE was detected between the two tested vectors, the vector with c-myc demonstrated a higher enzyme activity starting on Day 7 and further increasing on Day 14 post injection. This result indicates that c-myc benefits the enzyme activity of hBChE expressed in vivo.

C. Mutated hBChE (G117H E197Q)

Wildtype hBChE was mutated at aa 117 from G to H and aa 197 from E to Q. Innate hBChE sequence was then replaced with IL2 leader sequence. The expression and enzyme activity of hBChE (G117H E197Q) was evaluated in vivo. The hBChE expression cassette described herein is a transgene flanked by inverted terminal repeats (ITRs). The transgene includes cytomegalovirus (CMV) promoter, a commercially available Promega® intron (PI), hBChE C0 with IL2 leader peptide (SEQ ID NO: 4) or hBChE (G117H E197Q) with IL2 leader peptide (SEQ ID NO: 13), IRES, PRIMA1 PRP and an SV40 polyadenylation (polyA) signal. Different AAV.hBChE vector sequences were then packaged in the AAV8 viral capsid and further diluted in sterile PBS.

Figure 3A:
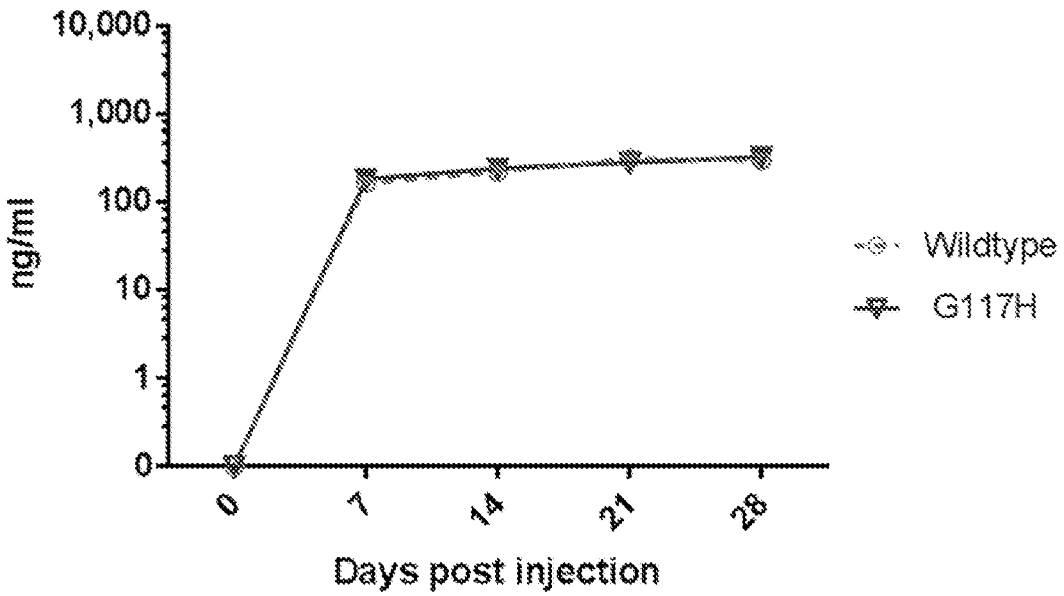
FIGS. 3A and 3B provide the effect of G117H, E197Q mutation on BChE expression (FIG. 3A) and activity (FIG. 3B) post vector administration in RAG KO mice. Expression and activity of BChE CO (circles connected via dashed line, marked as Wild-type) and G117H, E197Q (mutant, inverted triangle connected via solid line, marked as G117H) post-vector administration (in context of CMV promoter, IL2 leader, and PRIMA' PRP) as shown. Mice were injected IM with one 30 μl injections into the left gastrocnemius muscles. Orbital bleeds were collected on different days as shown. Mice were administered with a dose of $1\times10^{11}$ GC tittered by QPCR. Expression was measured in serum by ELISA and activity was measured by modified Ellman's method, values are expressed as mean±SD (n=5/group).
Figure 3B:
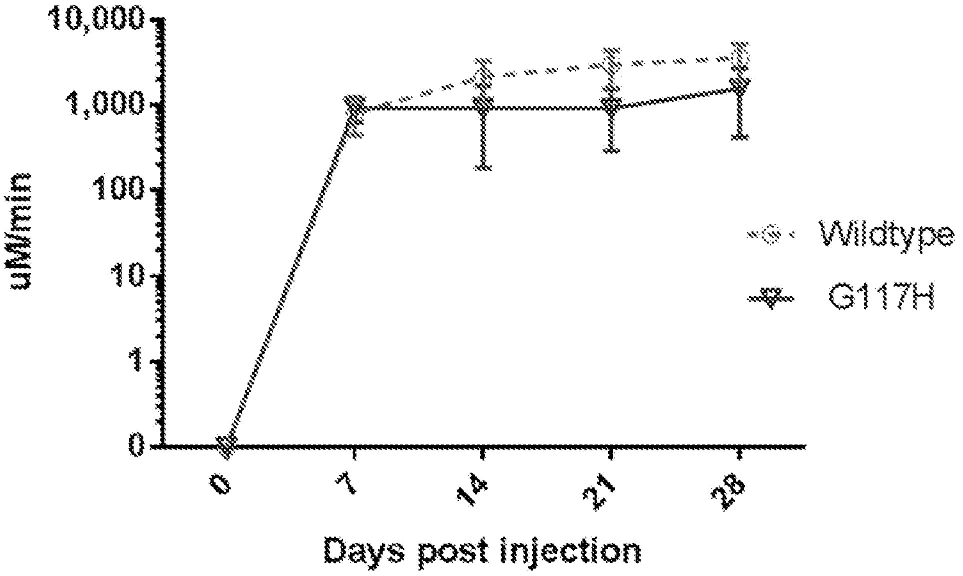

Studies were performed as described in Example 1. hBChE expressions and enzyme activity using the vectors described herein were assessed and the results were plotted in FIG. 3A and FIG. 3B respectively. No statistical significance in hBChE expression as well as enzyme activity was observed between the two tested vectors, indicating no advantages of the double mutations (G117H E197Q).

D. Leader Sequence

To evaluate the effects of different leader sequences on the expression of BChE using the viral vector deliver system in vivo, AAV.hBChE vectors with innate leader or IL2 leader peptide were constructed. The hBChE expression cassette described herein is a transgene flanked by inverted terminal repeats (ITRs). The transgene includes cytomegalovirus (CMV) promoter, a commercially available Promega® intron (PI), hBChE C0 with innate leader peptide (SEQ ID NO: 3) or hBChE CO with IL2 leader peptide (SEQ ID NO: 4), IRES, PRIMA1 PRP and an SV40 polyadenylation (polyA) signal. Different AAV.hBChE vector sequences were then packaged in the AAV8 viral capsid and further diluted in sterile PBS.

Figure 4A:
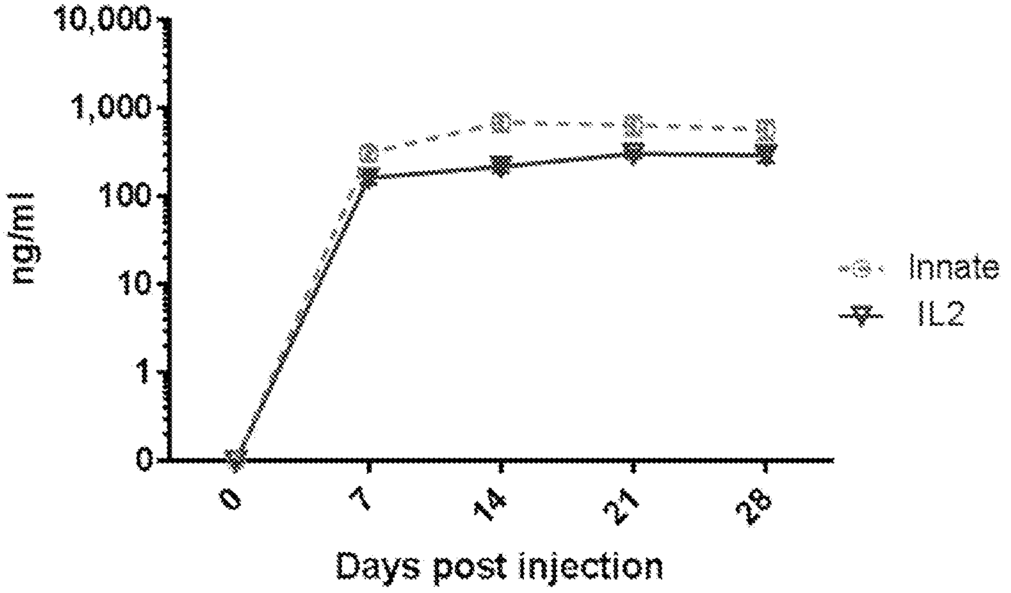
FIGS. 4A and 4B provide the effect of different secretion signals on BChE expression (FIG. 4A) and activity (FIG. 4B) post vector administration in RAG KO mice. Expression and activity of BChE C0 post-vector administration (in context of CMV promoter and PRIMA' PRP) in the presence of either innate (circles connected via dashed line) or hIL2 (inverted triangles connected via solid line) leader peptide. Mice were injected IM with one 30 μl injections into the left gastrocnemius muscles. Orbital bleeds were collected on different days as shown. Mice were administered with a dose of $1\times10^{11}$ GC tittered by QPCR. Expression was measured in serum by ELISA and activity was measured by modified Ellman's method, values are expressed as mean±SD (n=5/group).
Figure 4B:
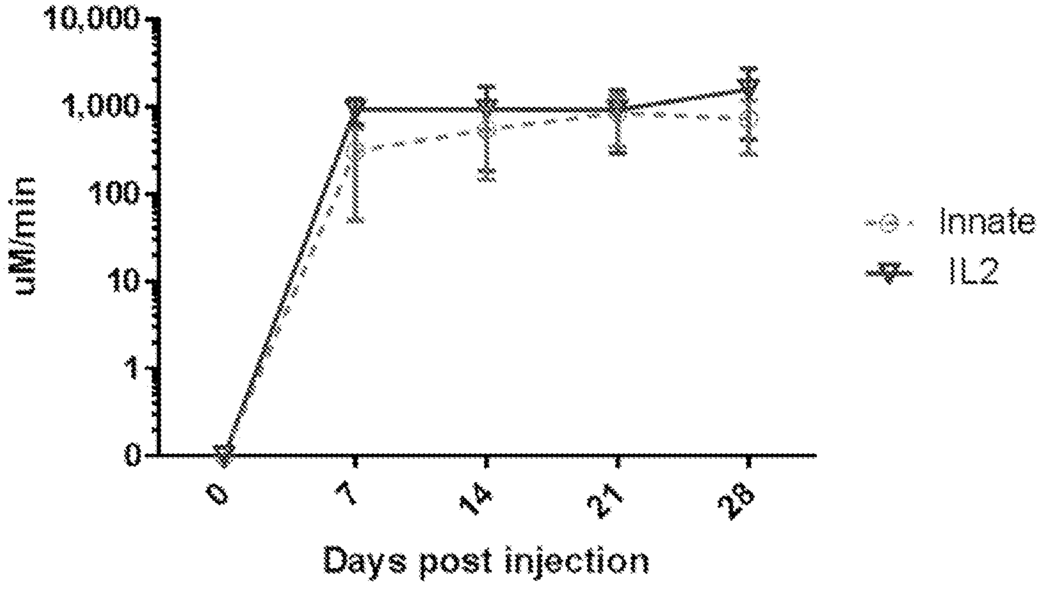

Studies were performed as described in Example 1. hBChE expressions and enzyme activity using the vectors described herein were assessed and the results were plotted in FIG. 4A and FIG. 4B respectively. The result demonstrated that the vector with innate leader sequence exhibited a higher expression level but a lower enzyme activity compared to the one with IL2 leader sequence in vivo.

E. 3'UTR

To evaluate the effects of 3'UTR on the expression of BChE using the viral vector deliver system in vivo, AAV.hBChE vectors in the presence or absence of WPRE (Woodchuck Hepatitis Virus (WHP) Posttranscriptional Regulatory Element, SEQ ID NO: 25) were constructed. The hBChE expression cassette described herein is a transgene flanked by inverted terminal repeats (ITRs). The transgene includes cytomegalovirus (CMV) promoter, a commercially available Promega® intron (PI), hBChE C0 with IL2 leader peptide (SEQ ID NO: 4), IRES, PRIMA1 PRP, and an SV40 polyadenylation (polyA) signal. WPRE was inserted immediately after PRIMA1 PRP if present. Different AAV.hBChE vector sequences were then packaged in the AAV8 viral capsid and further diluted in sterile PBS.

Figure 5A:
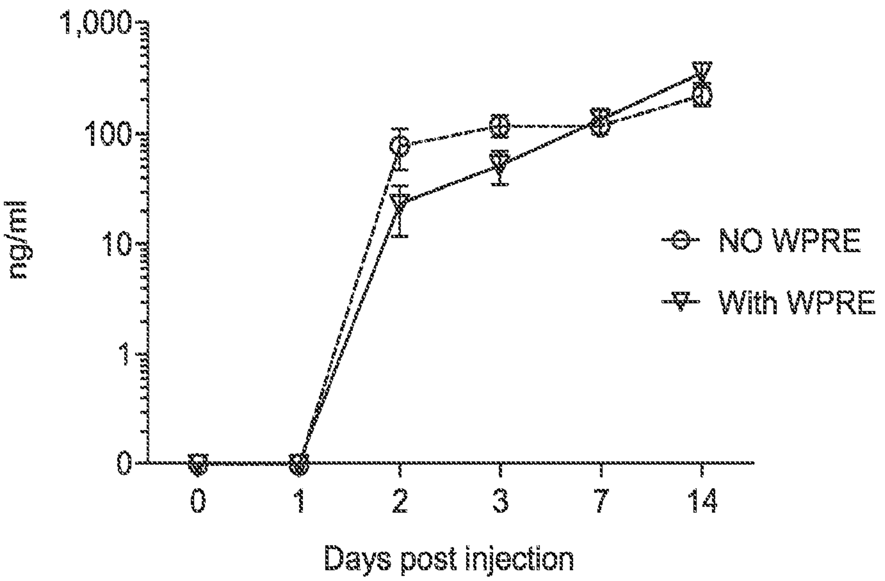
FIGS. 5A and 5B provide the effect of 3'UTR on BChE expression (FIG. 5A) and activity (FIG. 5B) post vector administration in RAG KO mice. Expression and activity of BChE CO post-vector administration (in context of CMV promoter, IL2 leader, and PRIMA1 PRP) in the presence (inverted triangles connected via solid line) or absence (circles connected via dashed line) of WPRE 3'UTR as shown. Mice were injected IM with one 30 μl injections into the left gastrocnemius muscles. Orbital bleeds were collected on different days as shown. Mice were administered with a dose of $1\times10^{11}$ GC tittered by QPCR. Expression was measured in serum by ELISA and activity was measured by modified Ellman's method, values are expressed as mean±SD (n=5/group).
Figure 5B:
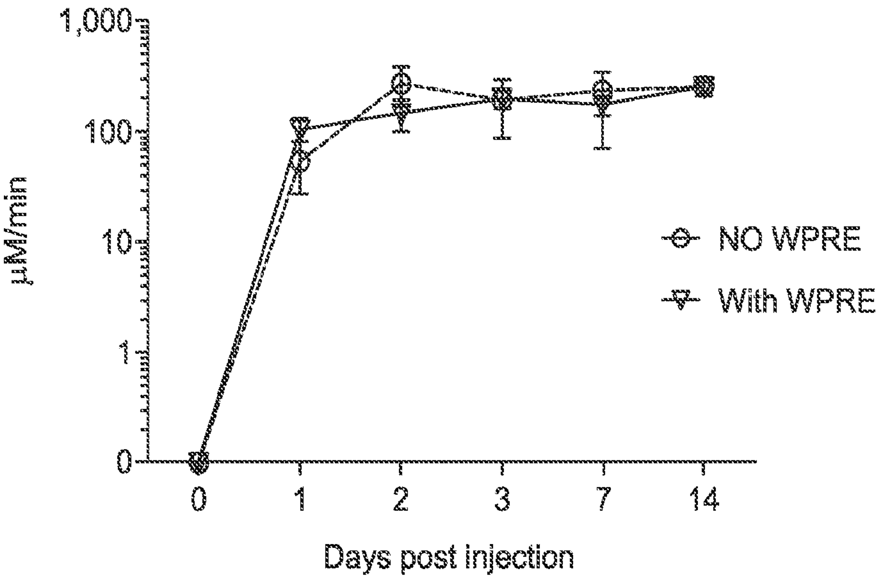

Studies were performed as described in Example 1. hBChE expressions and enzyme activity using the vectors described herein were assessed and the results were plotted in FIG. 5A and FIG. 5B respectively. No difference in the activity of hBChE was detected between the two tested vectors while the vector without WPRE revealed a higher hBChE expression on Day 2 and Day 3 post injection indicating that WPRE does not benefit the AAV.hBChE expression in vivo.

F. Promoter

To evaluate the effects of various promotors on the expression of BChE using the viral vector deliver system in vivo, AAV.hBChE vectors with CMV, UBC, C4/UbC (CMV C4 enhancer in the upstream Pf-UbC promoter), and CB7 (a hybrid between a cytomegalovirus (CMV) immediate early enhancer (C4) and the chicken beta actin promoter) were constructed. The hBChE expression cassette described herein is a transgene flanked by inverted terminal repeats (ITRs). The transgene includes the indicated promoter, an intron (PI or chicken beta-actin intron), hBChE CO with innate leader peptide (SEQ ID NO: 3), IRES, PRIMA1 PRP, and a polyadenylation (polyA, SV40 polyA or rBG polyA) signal. Different AAV.hBChE vector sequences were then packaged in the AAV8 viral capsid and further diluted in sterile PBS.

Figure 6A:
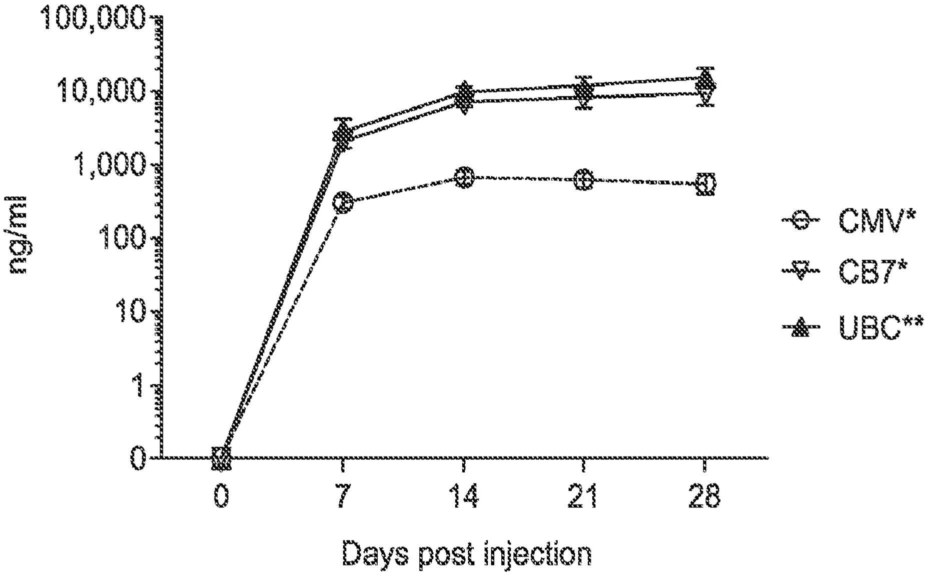
FIGS. 6A and 6B provide the effect of different promoters on BChE expression (FIG. 6A) and activity (FIG. 6B) post vector administration in RAG KO mice. Expression and activity of BChE C0 post-vector administration (in context of CMV promoter, innate leader, and PRIMA1 PRP) in the presence of different promoters CMV (circles connected via dashed line), CB7 (inverted triangles connected via solid line) and UBC (grey triangles connected via solid grey line) as shown. Mice were injected IM with one 30 μl injections into the left gastrocnemius muscles. Orbital bleeds were collected on different days as shown. Mice were administered with a dose of $1\times10^{11}$ GC. Expression was measured in serum by ELISA and activity was measured by modified Ellman's method, values are expressed as mean±SD (n=5/group).* indicates that the vector titer was quantified by QPCR (vectors with CMV or CB7 promoter) while ** indicates that the vector titer was quantified by ddPCR (vector with UBC promoter).
Figure 6B:
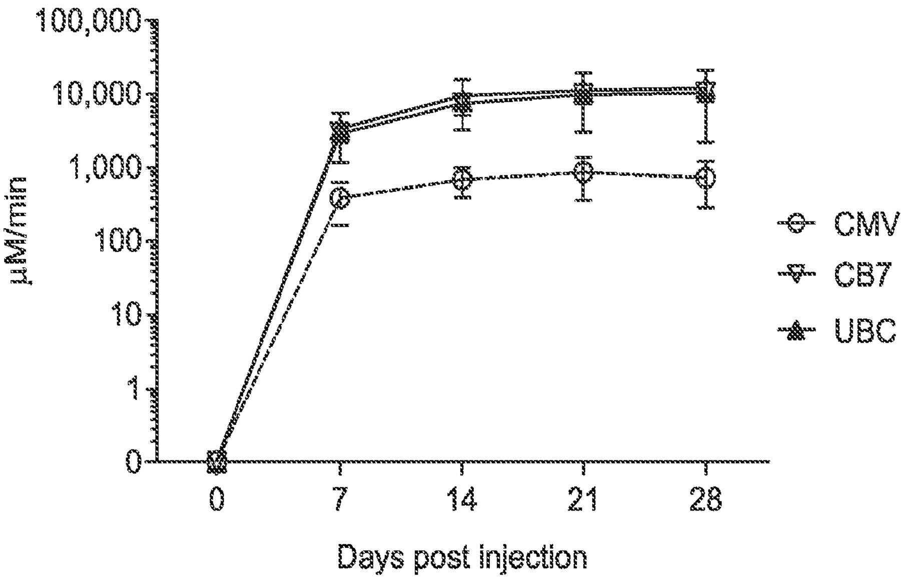
Figure 6C:
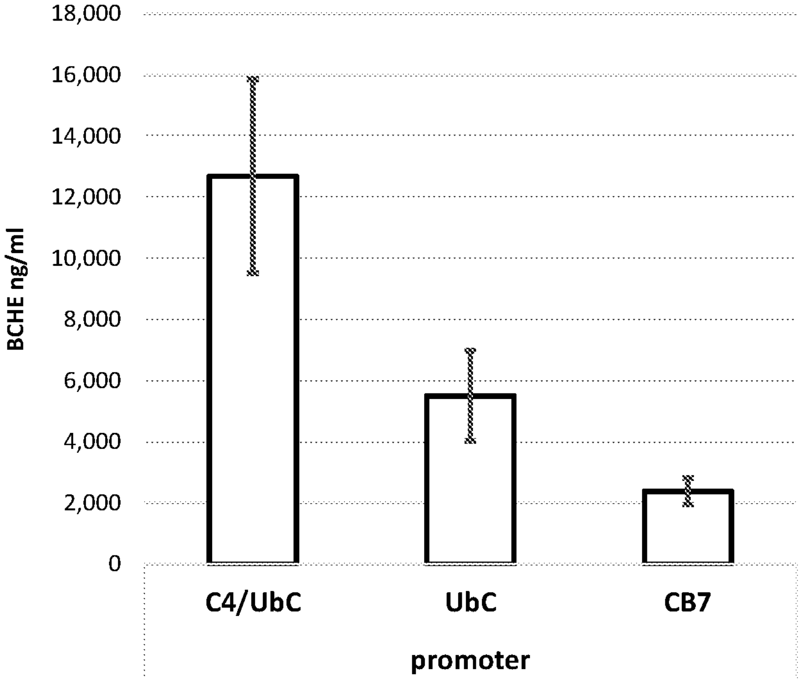
FIG. 6C provides the effect of different promoters on BChE expression post vector administration in RAG KO mice. Mice were injected IM with one 30 μl injections into the left gastrocnemius muscles. Orbital bleeds were collected on Day 3. Mice were administered with a dose of $1\times10^{11}$ GC. Expression was measured in serum by ELISA. Values are expressed as mean±SD.

Studies were performed as described in Example 1. hBChE expressions and enzyme activity using the vectors described herein were assessed and the results were plotted in FIG. 6A and FIG. 5B respectively. The vectors with CB7 and UBC promoter displayed a higher expression level as well as an increased activity compared to the one with CMV promoter. A further promoter, C4/UbC was constructed and compared to UbC and CB7. RAG KO mice injected i.m. with $1\times10^{11}$ GC of the tested vectors. Samples were collected on Day 3 post injection and processed as described in Example 1. The hBChE expression acquired was plotted in FIG. 6C. The result demonstrated a better expression utilizing C4/UbC promoter than UbC and CB7.

G. Codon Optimized Coding Sequences of BChE

Figure 7A:
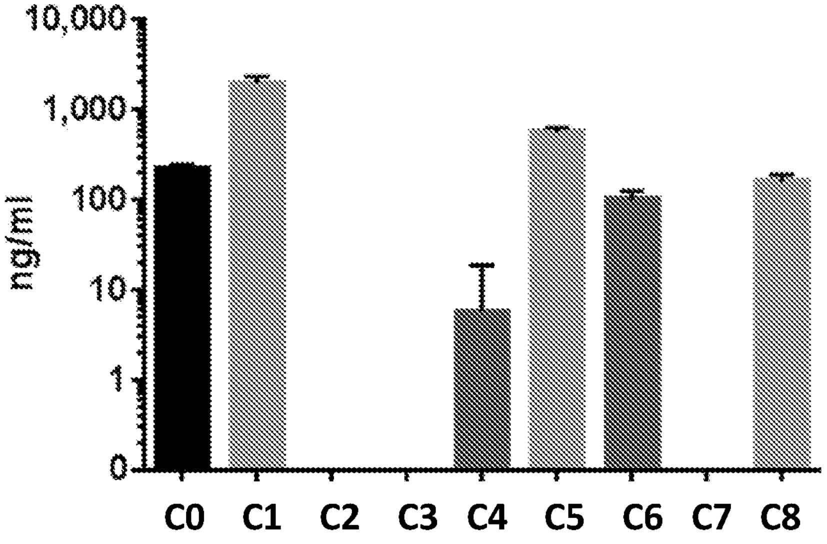
FIGS. 7A and 7B provide the effect of codon variation (C0, C1, C2 through C8) on BChE expression (FIG. 7A) and activity (FIG. 7B) post vector administration in RAG KO mice. Expression and activity of BChE with different codon variations (in context of CMV promoter, IL2 leader, and PRIMA1 PRP) as shown. Mice were injected IM with one 30 μl injections into the left gastrocnemius muscles. Orbital bleeds were collected on different days a shown. Mice were administered with a dose of $1\times10^{11}$ GC tittered by QPCR. Expression was measured in serum by ELISA and activity was measured by modified Ellman's method, values are expressed as mean±SD (n=5/group).
Figure 7B:
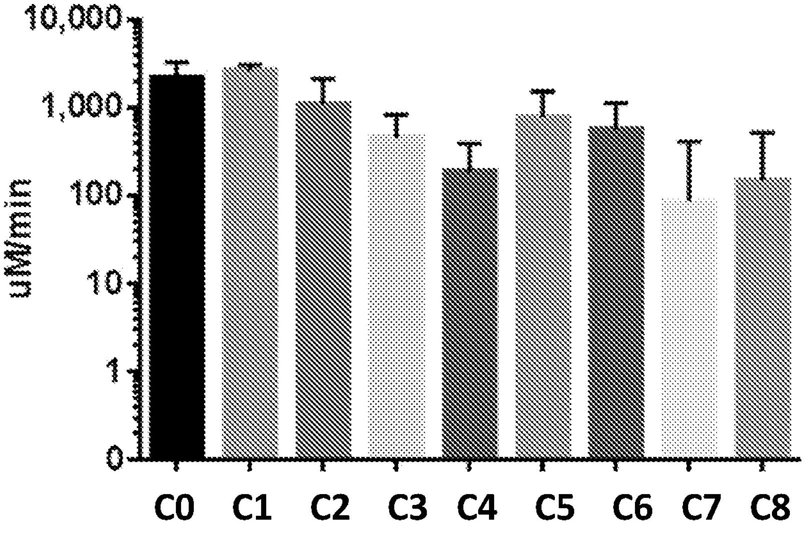

Nine codon-optimized coding sequences of hBChE (hBChE C0, hBChE C1, hBChE C2, hBChE C3, hBChE C4, hBChE C5, hBChE C6, hBChE C7, and hBChE C8) were designed and generated. The effects thereof were tested as described in Example 1 and above. hBChE expressions and enzyme activity were assessed and the results were plotted in FIG. 7A and FIG. 7B respectively. All tested vectors displayed a comparably similar activity of the hBChE expressed (FIG. 7B). However, the hBChE expression level varied. An about 2000 ng/ml of hBChE was detected in the samples from mice injected with AAV.hBChE C1. An about 500 ng/ml of hBChE was detected in the samples from mice injected with AAV.hBChE C5 while an about 200 ng/ml of hBChE was found from mice injected with AAV.hBChE C0, AAV.hBChE C6 and AAV.hBChE C8. AAV.hBChE C4 showed about 6 ng/ml of hBChE in the tested sample. In contrast, AAV vectors with hBChE C2, C3 and C7 showed an undetectable expression of hBChE.

H. Constructed with Preferred Elements in Mice

Based on the results described in Example 2, Sections A through G, four AAV.hBChE vectors listed below as promoter-5'UTR-leader-BChE-IRES-leader-PRP-polyA were constructed and further tested in mice as described in Example 1. The results were plotted in FIGS. 8A-8H.

(i) UbC-cmyc-IL2-BChE C1-IRES-IL2-PRIMA1-SV40 [nt 14 to nt 4162 of SEQ ID NO: 30]

Figure 8A:
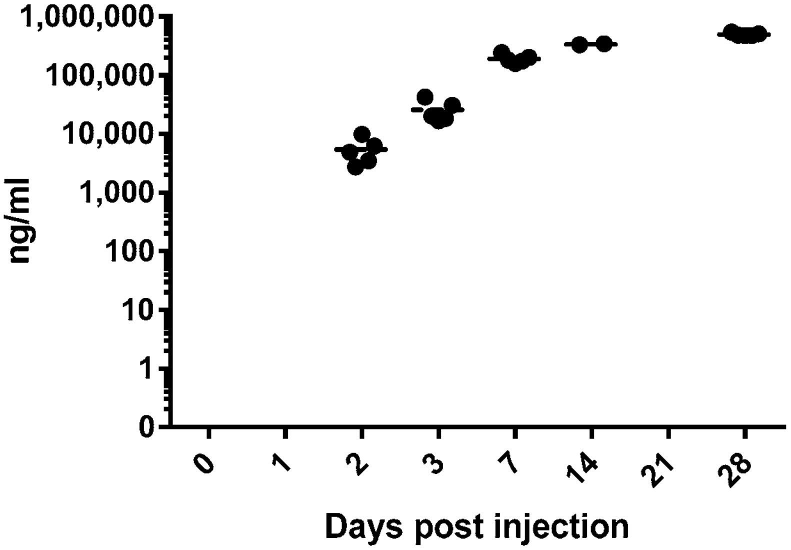
FIGS. 8A-8H illustrate test constructs in RAG KO mice. Expression (FIGS. 8A, 8C, 8E and 8G) and activity (FIGS. 8B, 8D, 8F and 8H) of BChE C1 in the 4 constructs with most preferred elements as shown (FIGS. 8A and 8B, UbC-cmyc-IL2-BChE C1-IRES-IL2-PRIMA1-SV40.
Figure 8B:
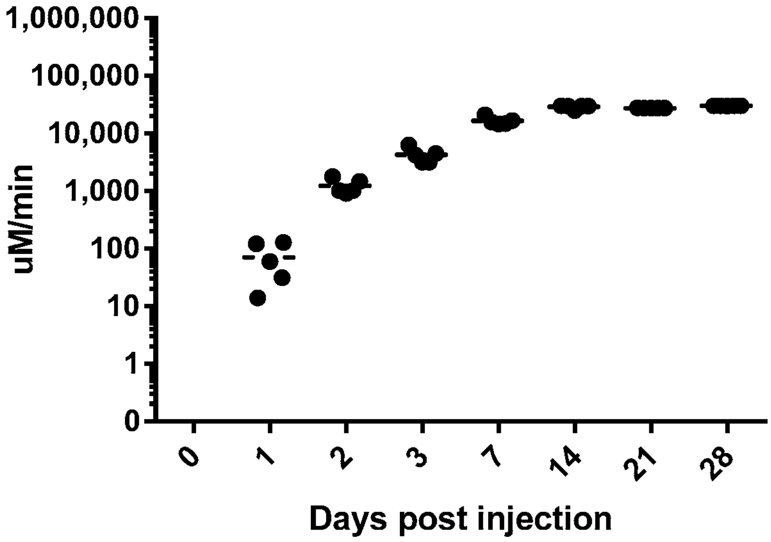

On Day 2 post injection, about 6000 ng/ml of hBChE was detected in RAG KO mice. The hBChE expression kept increasing and reached 700,000 ng/ml on Day 28 (FIG. 8A). In the activity assay, an about 70 μM/min was detected on Day 1 post injection. A sustained increase of activity was observed during Day 1 to Day 14. On Day 14 till the end of the observation period (Day 28), the enzyme activity reached plateau at ~30,000 μM/min (FIG. 8B).

Figure 9A:
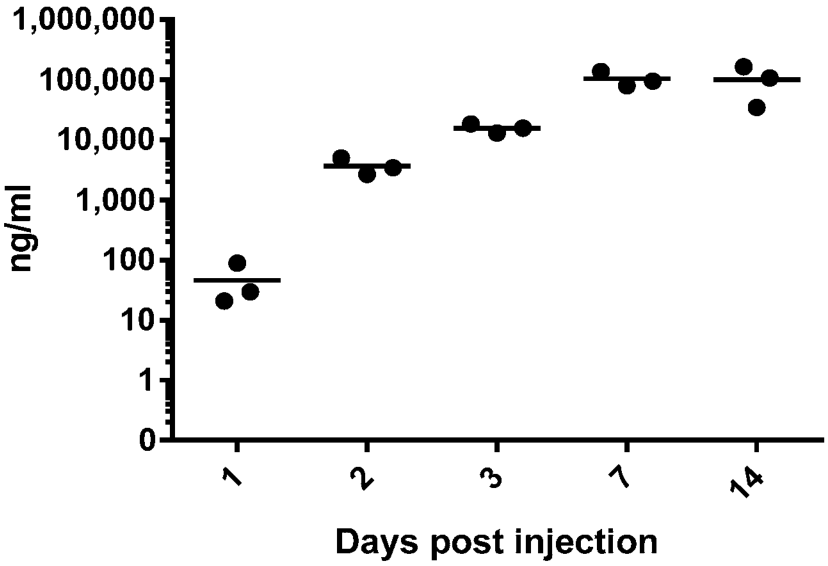
FIGS. 9A-9D show expression (FIGS. 9A and 9C) and activity (FIGS. 9B and 9D) of BChE C1 in the 2 test constructs in BChE KO mice as shown (FIGS. 9A and 9B, UbC-cmyc-IL2-BChE C1-IRES-IL2-PRIMA1-SV40.
Figure 9B:
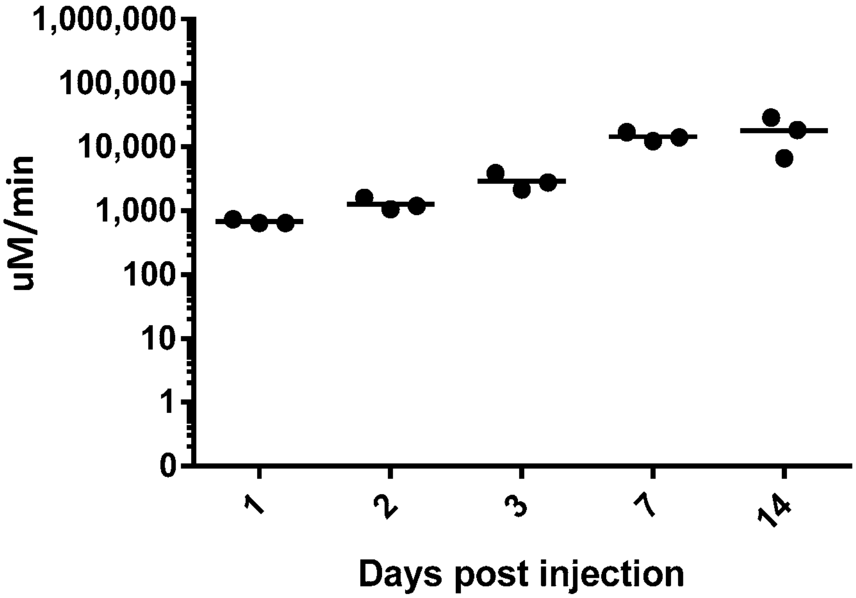
Figure 10A:
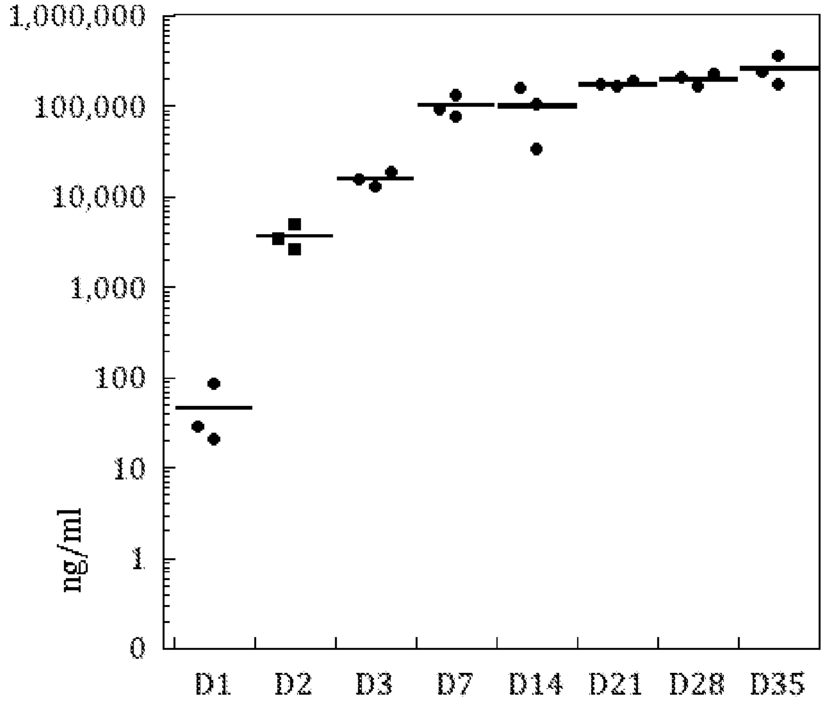
FIGS. 10A and 10B show expression of BChE C1 in the 2 test constructs in BChE KO mice as shown (FIG. 10A, UbC-cmyc-IL2-BChE C1-IRES-IL2-PRIMA1-SV40.

The vector described herein is further tested in BChE KO mice as described in Example 1. The results are shown in FIGS. 9A, 10A and 9B. On Day 1 post injection, about 50 ng/ml of hBChE was detected. Expression onset is early and becomes steady state after day 21.

Figure 9C:
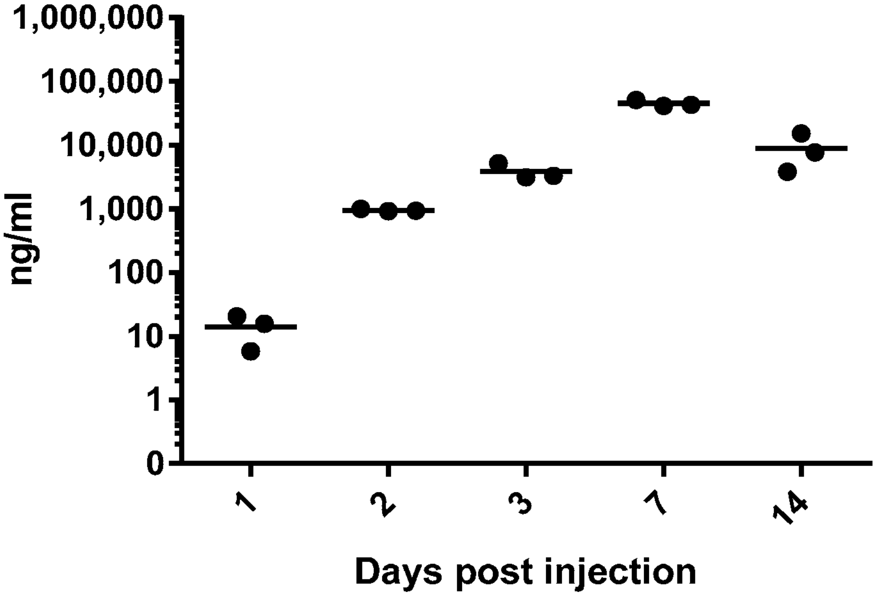
Figure 9D:
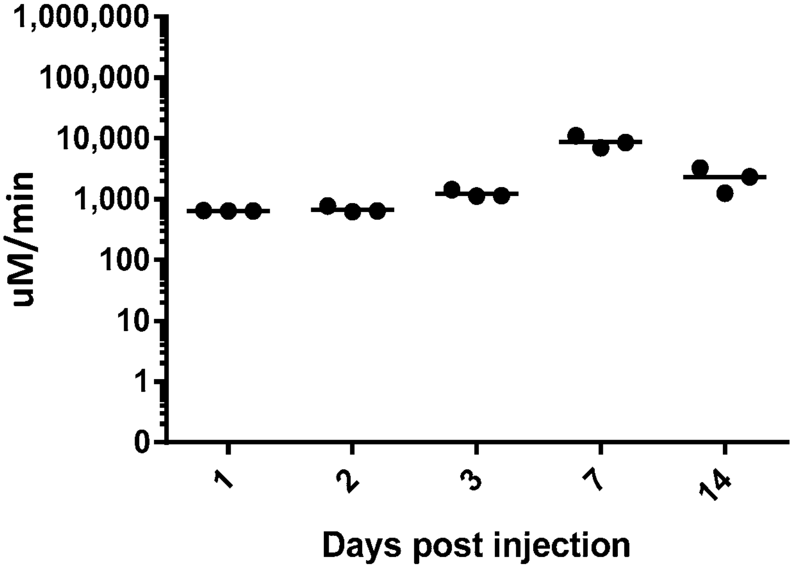
Figure 9E:
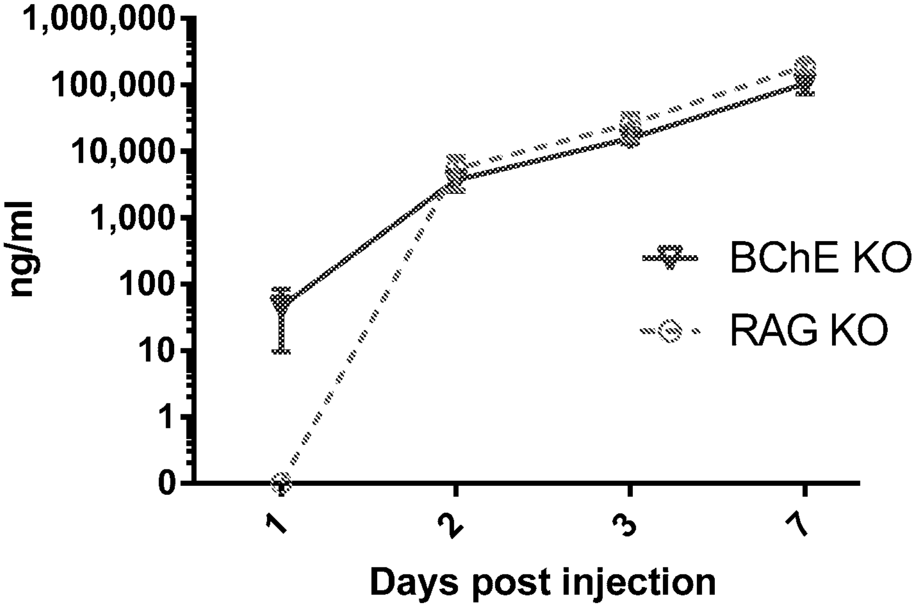
FIGS. 9E-9H show comparison of BChE expression (FIGS. 9E and 9G) and activity (FIGS. 9F and 9H) of BChE C1 in RAG KO mice (circles connected via dashed line) and BChE KO mice (inverted triangles connected via solid line) utilizing the 2 test constructs (FIGS. 9A and 9B, UbC-cmyc- IL2-BChE C1-IRES-IL2-PRIMA1-SV40.
Figure 9F:
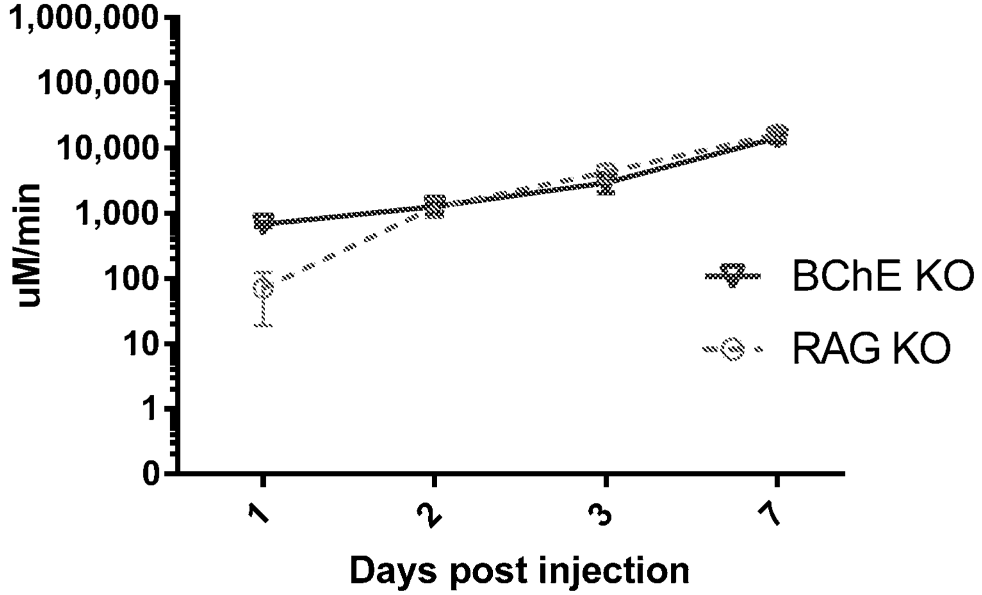

Overlays of the data acquired in RAG KO (triangle) and BChE KO (circle) mice were generated and plotted in FIG. 9E (expression) and FIG. 9F (enzyme activity).

Furthermore, in-gel butyrylcholinesterase activity assay was performed as described in Example 1. A representative result is shown in FIG. 15. Serum collected on Day 0 and Day 56 from RAG KO mouse injected with $1\times10^{11}$ GC of AAV8.UbC.hIL2.BChE C1.IRES.PRIMA1.SV40 vector was assessed. A low level of BChE tetramer was observed on Day 0 while an increased tetramer as well as monomer, dimer and BChE with albumin were observed on Day 36, indicating a successful expression of functional BChE.

(ii) UbC-cmyc-IL2-BChE C1-IRES-IL2-LPDN-SV40 [nt 14 to nt 4874 of SEQ ID NO: 31]

Figure 8C:
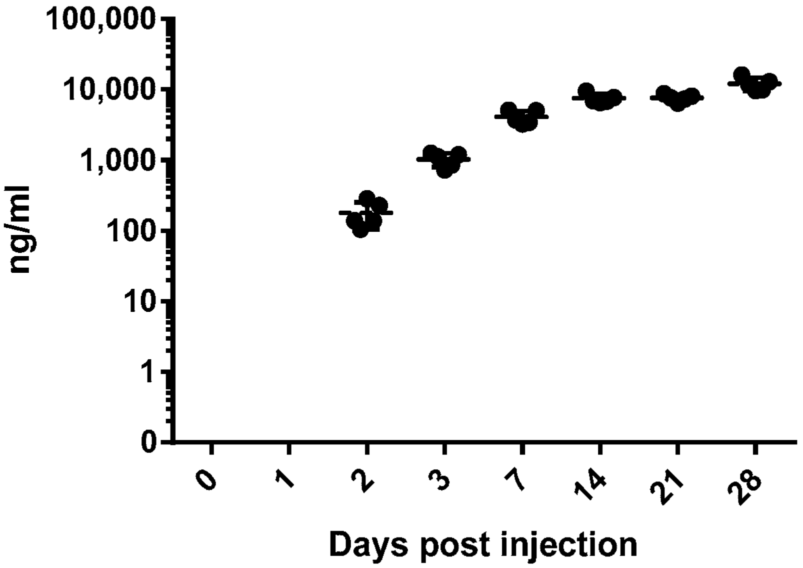
Figure 8D:
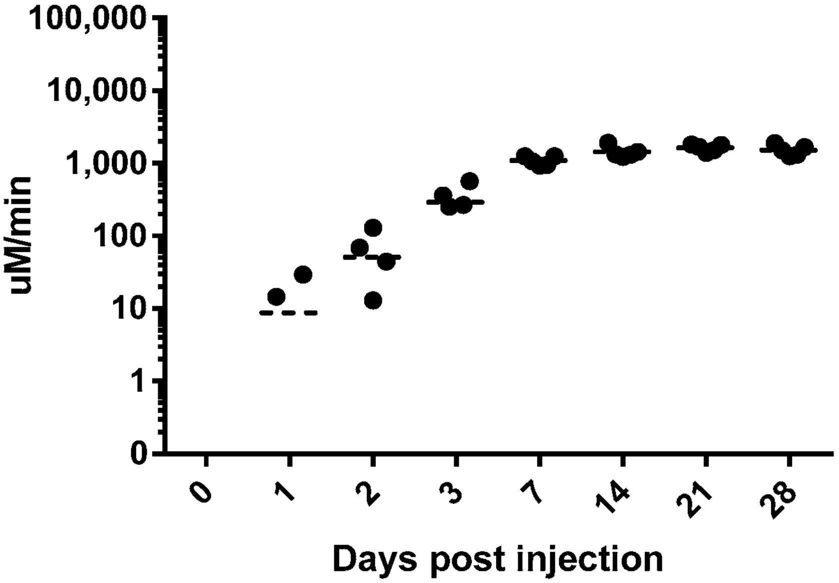

On Day 2 post injection, an about 200 ng/ml of hBChE was detected in RAG KO mice. The hBChE expression kept increasing and reached ~10,000 ng/ml on Day 28 (FIG. 8C). In the activity assay, an about 9 μM/min was detected on Day 1 post injection. A sustained increase of activity was observed during Day 1 to Day 14. On Day 14 till the end of the observation period (Day 28), the enzyme activity reached plateau at ~1,000 μM/min (FIG. 8D).

(iii) CB7-cmyc-IL2-BChE C1-IRES-IL2-PRIMA1-rBG [SEQ ID NO: 32]

Figure 8E:
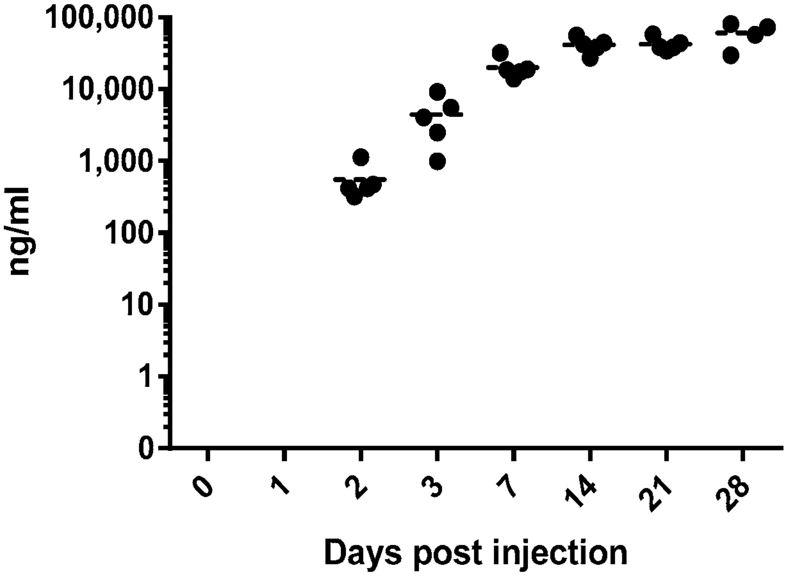
Figure 8F:
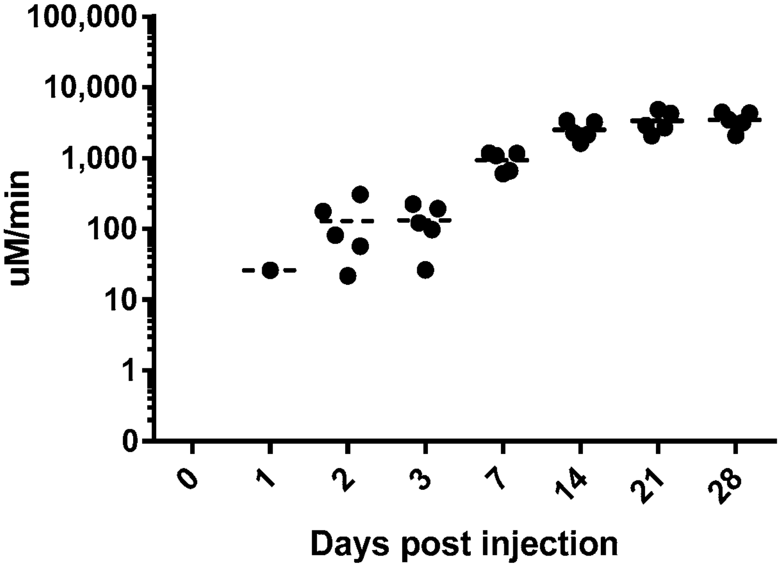

On Day 2 post injection, an about 600 ng/ml of hBChE was detected in RAG KO mice. The hBChE expression kept increasing and reached ~50,000 ng/ml on Day 28 (FIG. 8E). In the activity assay, an about 30 μM/min was detected on Day 1 post injection. A sustained increase of activity was observed during Day 1 to Day 21. On Day 21 till the end of the observation period (Day 28), the enzyme activity reached plateau at 3,000 μM/min (FIG. 8F).

(iv) CB7-cmyc-IL2-BChE C1-IRES-IL2-LPDN-rBG [SEQ ID NO: 33]

Figure 8G:
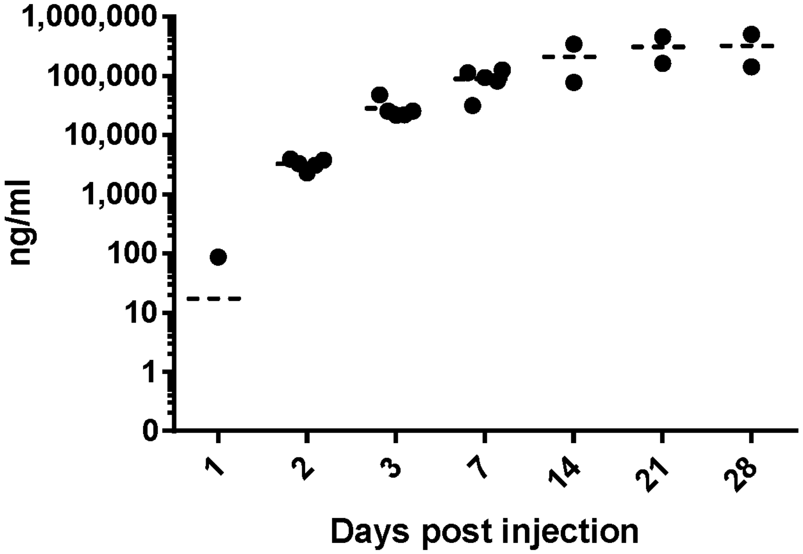
Figure 8H:
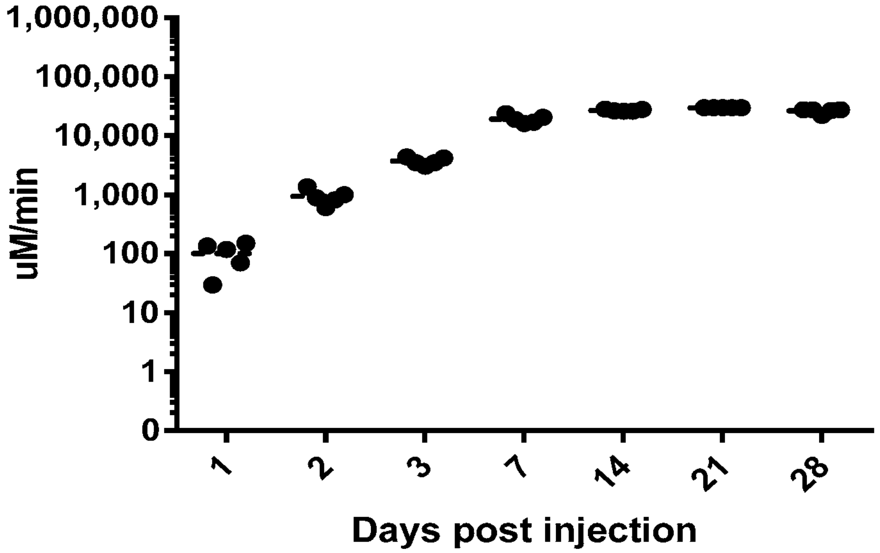

On Day 1 post injection, an about 20 ng/ml of hBChE was detected in RAG KO mice. The hBChE expression kept increasing and reached plateau at ~300,000 ng/ml on Day 14 (FIG. 8G). In the activity assay, an about 100 μM/min of activity was detected on Day 1 post injection. A sustained increase of activity was observed during Day 1 to Day 7. On Day 7 till the end of the observation period (Day 28), the enzyme activity reached plateau at ~20,000 μM/min (FIG. 8H).

Figure 10B:
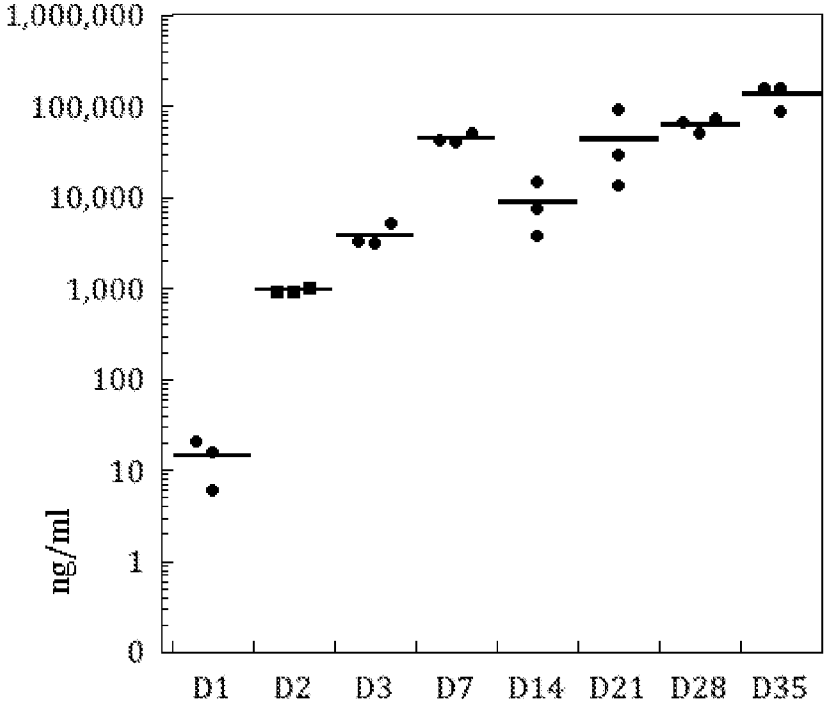

The vector described herein is further tested in BChE KO mice as described in Example 1. The results are shown in FIGS. 9C, 10B and 9D. On Day 1 post injection, an about 17 ng/ml of hBChE was detected. The hBChE expression kept increasing and reached ~40,000 ng/ml on Day 7. On Day 14, the hBChE expression was detected as ~10,000 ng/ml (FIGS. 9C and 10B). Another slow growth phase was observed starting Day 14 and the expression reached 160, 000 ng/ml on Day 35 post injection(FIG. 10B). In the activity assay, an about 700 μM/min was detected on Day 1 post injection. A sustained increase of activity was observed and reached 9,000 μM/min on Day 7. On Day 14, the activity was decreased to 2,000 μM/min (FIG. 9B).

Figure 9G:
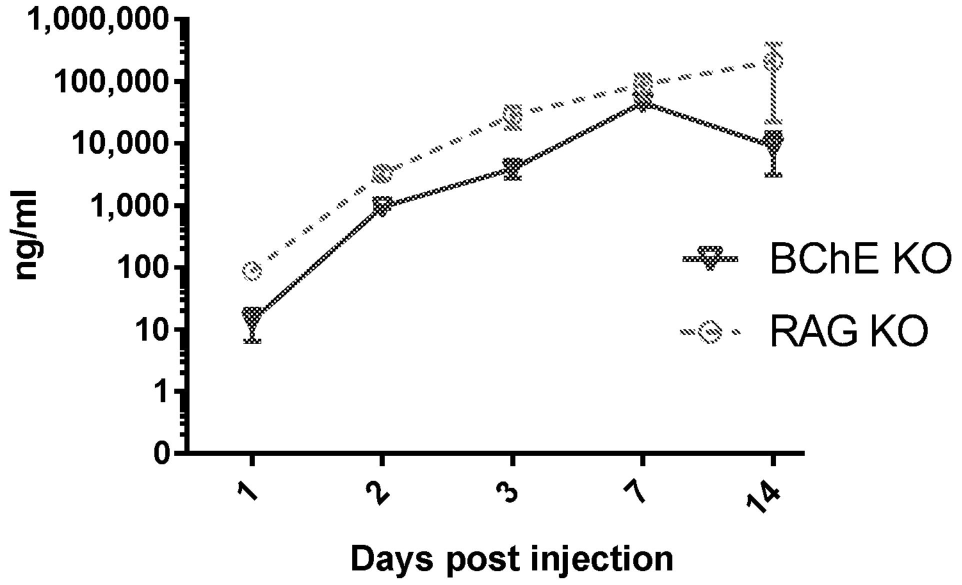
Figure 9H:
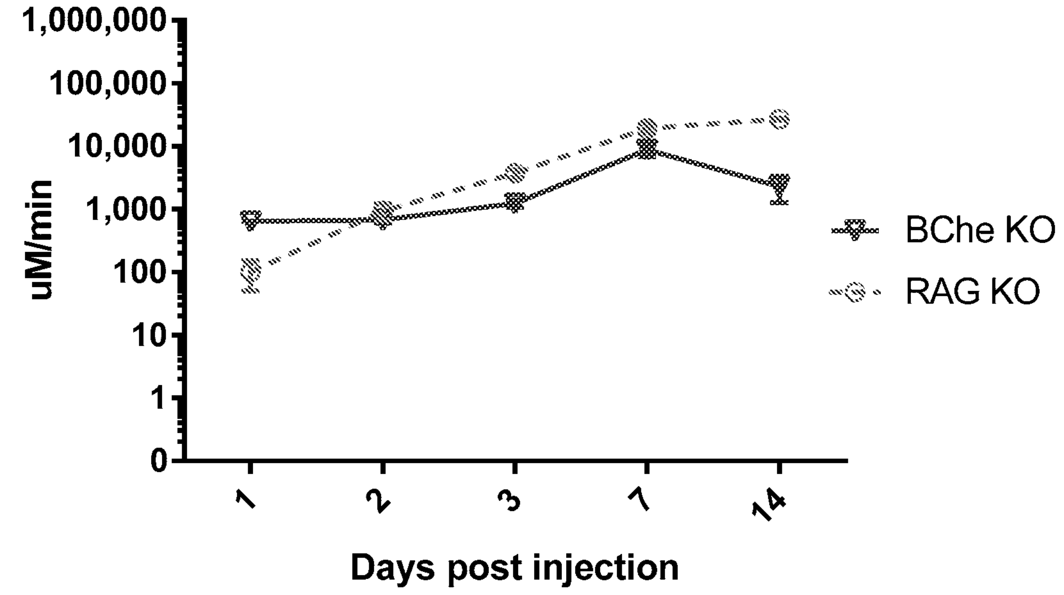

Overlays of the data acquired in RAG KO (triangle) and BChE KO (circle) mice were generated and plotted in FIG. 9G (expression) and FIG. 9H (enzyme activity).

Example 3

Dosage Comparison

To investigate the dosage-dependent effects of the four vectors described in Example 2, Section H, two doses of the vectors were utilized in vivo and evaluated as described below as well as in Example 1: $1\times10^{10}$ GC and $1\times10^{11}$ GC. The results were plotted in FIGS. 11A to 13B.

(i) UbC-cmyc-IL2-BChE C1-IRES-IL2-PRIMA1-SV40 [nt 14 to nt 4162 of SEQ ID NO: 30]

hBChE expression and activity is evaluated using samples collected from the RAG KO mice injected with $1\times10^{10}$ GC of the vector. The result is compared to the data described in Example 2, Section H (i).

Figure 11A:
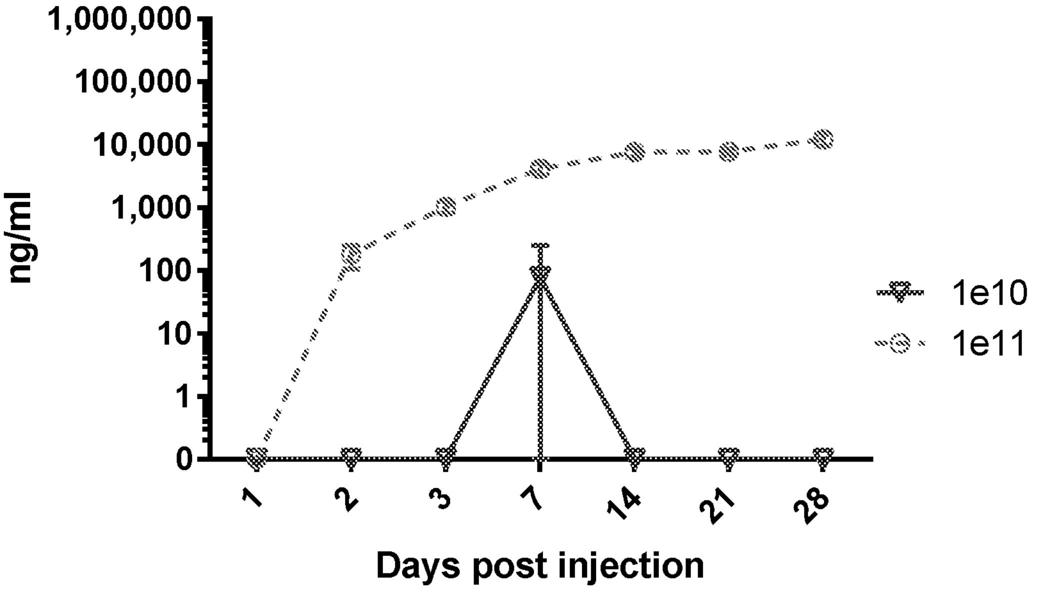
FIGS. 11A and 11B show expression (FIG. 11A) and activity (FIG. 11B) of BChE in RAG KO mice post injection with the UbC-cmyc-IL2-BChE C1-IRES-IL2-LPDN-SV40 vector. Mice were injected IM with one 30 μl injections into the left gastrocnemius muscles. Orbital bleeds were collected on different days as shown. Mice were administered with a dose of $1\times10^{11}$ GC (circles connected via dashed line) or $1\times10^{10}$ GC (inverted triangles connected via solid line) titered by QPCR. Expression was measured in serum by ELISA and activity was measured by modified Ellman's method.
Figure 11B:
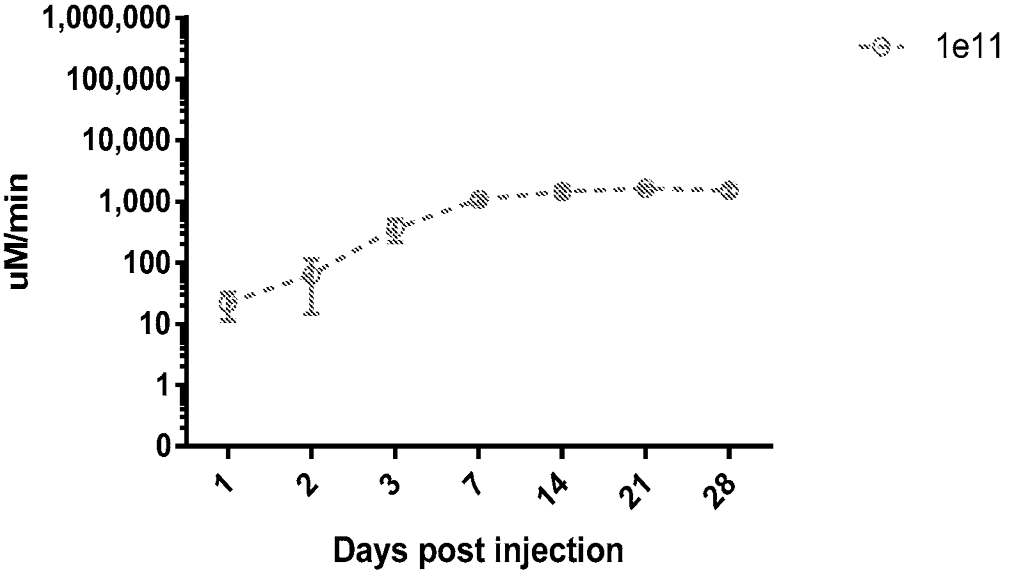

(ii) UbC-cmyc-IL2-BChE C1-IRES-IL2-LPDN-SV40 [nt 14 to nt 4874 of SEQ ID NO: 31]

hBChE expression was evaluated using samples collected from the RAG KO mice injected with $1\times10^{10}$ GC and $1\times10^{11}$ of the vector. The result was plotted in FIGS. 11A and 11B. A sudden peak in hBChE expression for low dosage group was observed on Day 7 (FIG. 11A). However, this data was not statistically significant thus did not represent the average data as only one out of five mice showed an expression while all of the rest do not. Activity of the samples acquired in the low dosage group is under investigation.

Figure 12A:
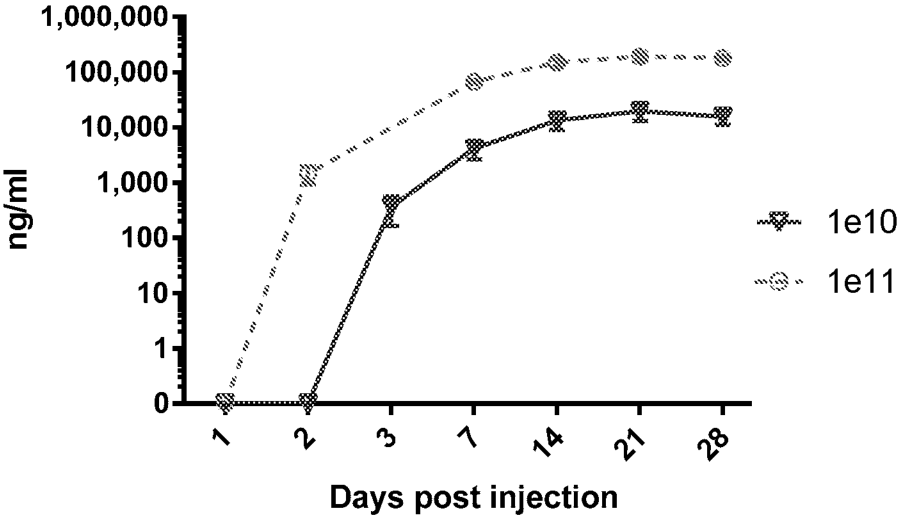
FIGS. 12A and 12B show expression (FIG. 12A) and activity (FIG. 12B) of BChE in RAG KO mice post injection with the CB7-cmyc-IL2-BChE C1-IRES-IL2-PRIMA1-rBG vector. Mice were injected IM with one 30 μl injections into the left gastrocnemius muscles. Orbital bleeds were collected on different days as shown. Mice were administered with a dose of $1\times10^{11}$ GC (circles connected via dashed line) or $1\times10^{10}$ GC (inverted triangles connected via solid line) titered by QPCR. Expression was measured in serum by ELISA and activity was measured by modified Ellman's method.
Figure 12B:
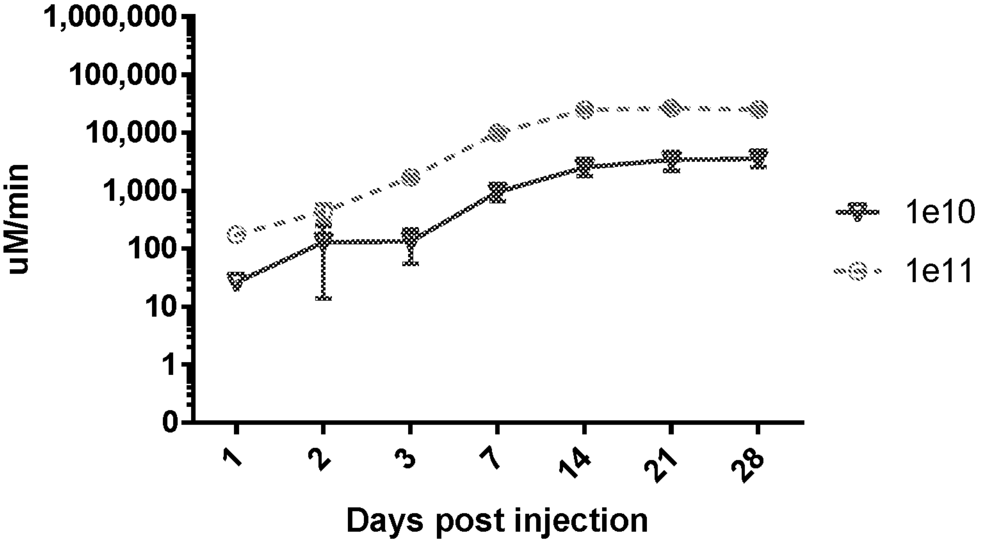

(iii) CB7-cmyc-IL2-BChE C1-IRES-IL2-PRIMA1-rBG [SEQ ID NO: 32]

hBChE expression and activity was evaluated using samples collected from the RAG KO mice injected with $1\times10^{10}$ GC and $1\times10^{11}$ of the vector. The result was plotted in FIGS. 12A and 12B.

hBChE expression was observed starting Day 3 post injection at about 300 ng/ml in the low dosage group while in the high dosage group, an about 1,000 ng/ml of hBChE was detected in RAG KO mice on Day 2. The hBChE expression of both groups kept increasing until Day 14. An about 10,000 ng/ml of expression was observed during Day 14 to Day 28 in the low dosage group while an about 100,000 ng/ml in the high dosage group (FIG. 12A). A steady increase in the enzyme activity was detected in both groups from Day 1 to Day 28 while the high dosage group demonstrated a higher activity during the observation period (FIG. 12B).

Figure 13A:
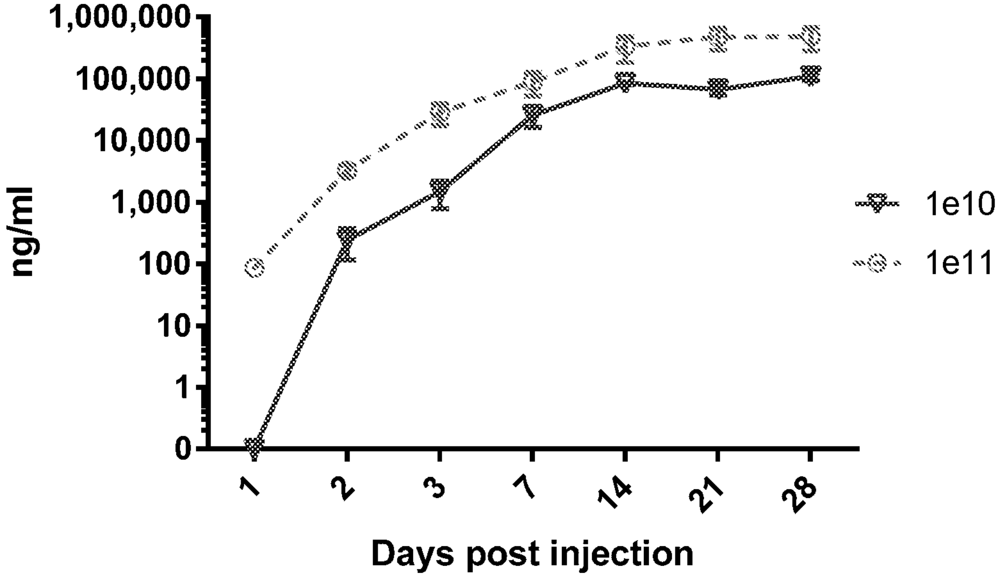
FIGS. 13A and 13B show expression (FIG. 13A) and activity (FIG. 13B) of BChE in RAG KO mice post injection with the CB7-cmyc-IL2-BChE C1-IRES-IL2-LPDN-rBG vector. Mice were injected IM with one 30 μl injections into the left gastrocnemius muscles. Orbital bleeds were collected on different days as shown. Mice were administered with a dose of (circles connected via dashed line) or $1\times10^{10}$ GC (inverted triangles connected via solid line) titered by QPCR. Expression was measured in serum by ELISA and activity was measured by modified Ellman's method.
Figure 13B:
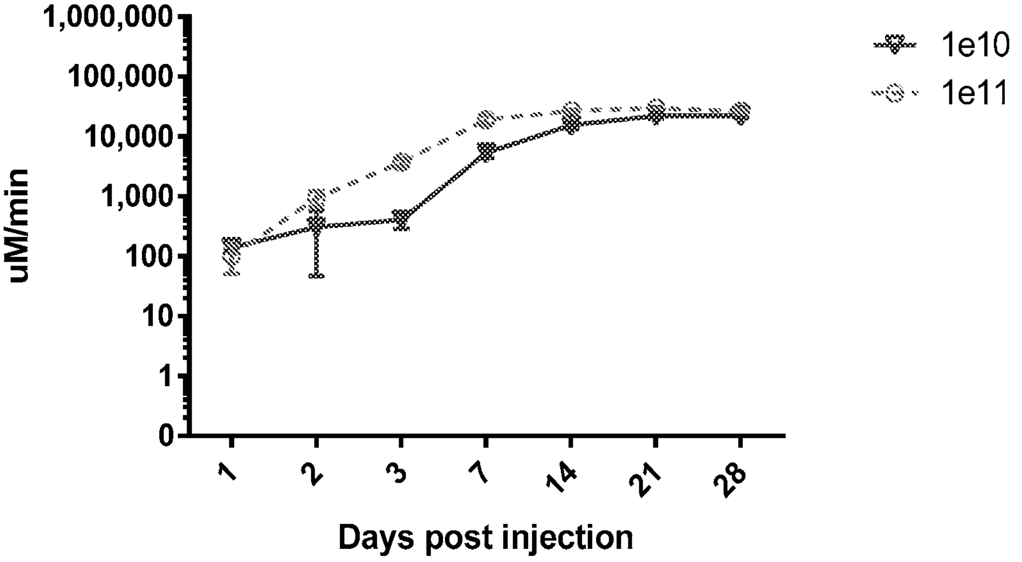

(iv) CB7-cmyc-IL2-BChE C1-IRES-IL2-LPDN-rBG [SEQ ID NO: 33]

hBChE expression and activity was evaluated using samples collected from the RAG KO mice injected with $1\times10^{10}$ GC and $1\times10^{11}$ of the vector. The result was plotted in FIGS. 13A and 13B.

hBChE expression was observed starting Day 2 post injection at about 200 ng/ml in the low dosage group while in the high dosage group, an about 100 ng/ml of hBChE was detected in RAG KO mice on Day 1. The hBChE expression of both groups kept increasing until Day 14. An about 50,000 ng/ml of expression was observed during Day 14 to Day 28 in the low dosage group while an about 300,000 ng/ml in the high dosage group (FIG. 13A). An increase of enzyme activity was observed in both groups while both groups demonstrated an about 100 μM/min of activity on Day 1 and an about 20,000 μM/min on Day 14 and Day 28. However, on Day 2, Day 3 and Day 7, an elevated activity was observed in the high dosage group compared to the low dosage group.

Example 4

Dose-dependent Protection Against Butyrylcholine (BCh) Challenge in BChE KO Mice $1\times10^{11}$ GC, $3\times10^{10}$ GC, $1\times10^{10}$ GC, $3\times10^{9}$ GC per mouse of CB7-cmyc-IL2-BChE C1-IRES-IL2-LPDN-rBG vectors injected to BChE KO mice on Day 1 as described in Example 1. On Day 8, butyrylcholine (BCh) challenge was performed as an intraperitoneal injection of BCh at 500 mg/kg body weight (>5× LD50, more than five times of the dose lethal to 50% of tested samples). Blood samples were collected, processed and evaluated as described in Example 1. BChE KO mice without vector injection and wild type mice were served as control. The Result is shown in the table below. A dose dependent protection effect was observed.

| Group | Vector Dose | % Survival |
|---|---|---|
| n = 5 | $1\times10^{11}$ GCs/mouse | 100% |
| n = 5 | $3\times10^{10}$ GCs/mouse | 100% |
| n = 4 | $1\times10^{10}$ GCs/mouse | 75% |
| n = 5 | $3\times10^{9}$ GCs/mouse | 20% |
| n = 5 | no vector | 0% |
| n = 5 | wild type | 0% |

Example 5

AAV.hBChE in Mice

Figure 14:
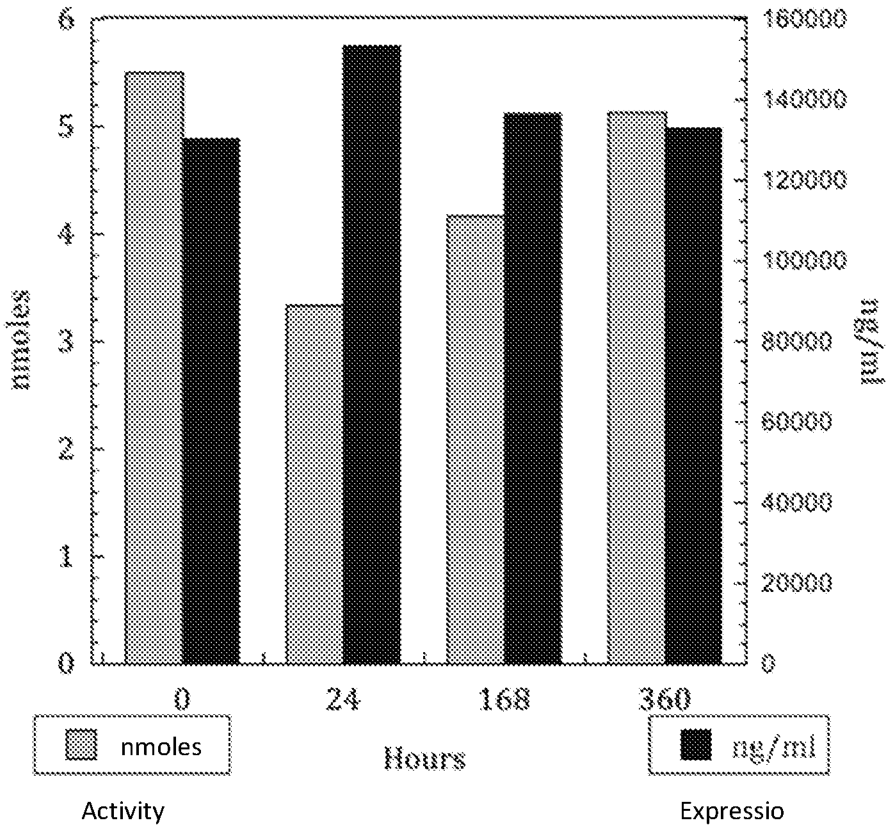
FIG. 14 provides expression (grey bars) and activity (black bars) of BChE in mice post injection with the rAAV.CMV.BChE C1 vector as described in Example 5.

The CB7-cmyc-IL2-BChE C1-IRES-IL2-LPDN-rBG vector were further evaluated in mice. i.m. injection of the vectors was performed and followed by an OP Challenge with two times of the MLD50 (minimal lethal dose that is lethal to 50% of animals tested). Blood samples were collected and evaluated to determine the expression and activity of hBChE. The result was plotted in FIG. 14. A reduction in the enzyme activity was observed 24 hours post challenge and a steady recovery was observed 168 hours and 360 hours post challenge (grey bars in FIG. 14). The BChE expression peaked at 24 hours post challenge and fell back to the baseline afterwards (black bars in FIG. 14). These data suggests a protection effect of AAV.hBChE vectors over the OP challenge in mice.

Sequence Listing Free Text

The following information is provided for sequences containing free text under numeric identifier <223>.

| SEQ ID NO: (containing free text) | Free text under <223> |
|---|---|
| 1 | <220><br><221> MISC_FEATURE<br><222> (1) . . . (26)<br><223> Innate leader/signal peptide/sequence<br><220><br><221> mat_peptide<br><222> (27) . . . (602) |
| 3 | <223> human BChE C0 with innate leader peptide. |
| 4 | <223> human BChE C0 with IL2 leader peptide. |
| 5 | <223> human BChE C1 with IL2 leader peptide.<br><220><br><221> sig_peptide<br><222> (11) . . . (67)<br><223> IL2 |
| 6 | <223> human BChE C2 with IL2 leader peptide. |
| 7 | <223> human BChE C3 with IL2 leader peptide. |
| 8 | <223> human BChE C4 with IL2 leader peptide. |
| 9 | <223> human BChE C5 with IL2 leader peptide. |
| 10 | <223> human BChE C6 with IL2 leader peptide. |
| 11 | <223> human BChE C7 with IL2 leader peptide. |
| 12 | <223> human BChE C8 with IL2 leader peptide. |
| 13 | <223> human BChE mutated at G117H and E197Q with IL2 |
| 14 | <223> CMV promoter |
| 15 | <223> CMV IE promoter |
| 16 | <223> CB promoter |
| 17 | <223> C4 enhancer |
| 18 | <223> UbC promoter |
| 19 | <223> c-myc |
| 20 | <223> IL2 leader sequence |
| 21 | <223> Mutated IL2 leader sequence |
| 22 | <223> IRES |
| 23 | <223> PRIMA1 PRP |
| 24 | <223> lamelledipodin (LDPN) PRP |
| 25 | <223> WPRE |
| 26 | <223> Rabbit beta-globin (rBG) polyA |
| 27 | <223> SV40 polyA |
| 28 | <223> AAV2 5'ITR |
| 29 | <223> AAV2 3'ITR |
| 30 | <223> UbC-cmyc-IL2-BChE C1-IRES-IL2-PRIMA1-SV40<br><220><br><221> repeat_region<br><222> (14) . . . (143)<br><223> 5'ITR<br><220><br><221> promoter<br><222> (204) . . . (1430)<br><223> UbC promoter<br><220><br><221> Intron<br><222> (1524) . . . (1656)<br><223> Promega chimeric intron (PI)<br><220><br><221> misc_feature<br><222> (1771) . . . (3572)<br><223> BChE coding sequence C1<br><220><br><221> misc_feature<br><222> (1782) . . . (1838)<br><223> human IL2 leader sequence<br><220><br><221> misc_feature<br><222> (3572) . . . (4162)<br><223> IRES<br><220><br><221> misc_feature<br><222> (4167) . . . (4407)<br><223> PRIMA1 PR |

-continued

| SEQ ID NO: (containing free text) | Free text under <223> |
|---|---|
| | <220> |
| | <221> polyA |
| | <222> (4410) . . . (4641) |
| | <223> SV40 late PolyA |
| | <220> |
| | <221> repeat_region |
| | <222> (4706) . . . (4835) |
| | <223> 3'ITR |
| 31 | <223> UbC-cmyc-IL2-BChE C1-IRES-IL2-LPDN-SV40 |
| | <220> |
| | <221> repeat_region |
| | <222> (14) . . . (143) |
| | <223> 5'ITR |
| | <220> |
| | <221> promoter |
| | <222> (204) . . . (1430) |
| | <223> UbC promoter |
| | <220> |
| | <221> Intron |
| | <222> (1524) . . . (1656) |
| | <223> Promega chimeric intron |
| | <220> |
| | <221> misc_feature |
| | <222> (1770) . . . (3574) |
| | <223> BChE coding sequence C1 |
| | <220> |
| | <221> misc_feature |
| | <222> (1782) . . . (1838) |
| | <223> human IL2 leader sequence |
| | <220> |
| | <221> misc_feature |
| | <222> (3572) . . . (4162) |
| | <223> IRES |
| | <220> |
| | <221> misc_feature |
| | <222> (4167) . . . (4446) |
| | <223> LPDN PRP |
| | <220> |
| | <221> polyA_signal |
| | <222> (4449) . . . (4680) |
| | <223> SV40 late polyadenylation signal |
| | <220> |
| | <221> repeat_region |
| | <222> (4745) . . . (4874) |
| | <223> 5'ITR |
| 32 | <223> CB7-cmyc-IL2-BChE C1-IRES-IL2-PRIMA1-rBG |
| | <220> |
| | <221> repeat_region |
| | <222> (1) . . . (130) |
| | <223> 5'ITR |
| | <220> |
| | <221> promoter |
| | <222> (198) . . . (579) |
| | <223> CMV IE promoter |
| | <220> |
| | <221> enhancer |
| | <222> (279) . . . (538) |
| | <223> C4 enhancer with 2 mismatches |
| | <220> |
| | <221> promoter |
| | <222> (582) . . . (862) |
| | <223> CB promoter |
| | <220> |
| | <221> TATA_signal |
| | <222> (836) . . . (839) |
| | <220> |
| | <221> Intron |
| | <222> (956) . . . (1928) |
| | <223> Chicken beta-actin intron |
| | <220> |
| | <221> misc_feature |
| | <222> (1941) . . . (3742) |
| | <223> BChE coding sequence C1 |
| | <220> |
| | <221> misc_feature |
| | <222> (1950) . . . (2006) |
| | <223> human IL2 leader sequence |
| | <220> |
| | <221> misc_feature |
| | <222> (3740) . . . (4330) |
| | <223> IRES |
| | <220> |
| | <221> misc_feature |
| | <222> (4335) . . . (4560) |
| | <223> PRIMA1 PRP |
| | <220> |
| | <221> polyA_signal |
| | <222> (4621) . . . (4747) |
| | <223> Rabbit beta globin polyA |
| | <220> |
| | <221> repeat_region |
| | <222> (4836) . . . (4965) |
| | <223> 3'ITR |
| 33 | <223> CB7-cmyc-IL2-BChE C1-IRES-IL2-LPDN-rBG |
| | <220> |
| | <221> repeat_region |
| | <222> (1) . . . (130) |
| | <223> 5'ITR |
| | <220> |
| | <221> enhancer |
| | <222> (279) . . . (538) |
| | <223> C4 enhancer with 2 mismatches |
| | <220> |
| | <221> promoter |
| | <222> (582) . . . (862) |
| | <223> CB promoter |
| | <220> |
| | <221> TATA_signal |
| | <222> (836) . . . (839) |
| | <220> |
| | <221> Intron |
| | <222> (956) . . . (1928) |
| | <223> Chicken beta-actin intron |
| | <220> |
| | <221> misc_feature |
| | <222> (1941) . . . (3739) |
| | <223> BChE conding sequence C1 |
| | <220> |
| | <221> misc_feature |
| | <222> (3740) . . . (4330) |
| | <223> IRES |
| | <220> |
| | <221> misc_feature |
| | <222> (4335) . . . (4614) |
| | <223> LPDN PRP |
| | <220> |
| | <221> polyA_signal |
| | <222> (4675) . . . (4801) |
| | <223> Rabbit beta globin polyA |
| | <220> |
| | <221> repeat_region |
| | <222> (4890) . . . (5019) |
| 34 | <223> C4/Ubc hIL2 BChE C1 IRES LPDN |
| | <220> |
| | <221> repeat_region |
| | <222> (1) . . . (130) |
| | <223> 5'ITR |
| | <220> |
| | <221> enhancer |
| | <222> (279) . . . (538) |
| | <223> C4 enhancer with 2 mismatches |
| | <220> |
| | <221> promoter |
| | <222> (565) . . . (1791) |
| | <223> UbC promoter |
| | <220> |
| | <221> misc_feature |
| | <222> (1826) . . . (3624) |
| | <223> BChE coding sequence C1 |

-continued

| SEQ ID NO: (containing free text) | Free text under <223> |
|---|---|
| | <220><br><221> misc_feature<br><222> (3625) . . . (4215)<br><223> IRES<br><220><br><221> misc_feature<br><222> (4220) . . . (4499)<br><223> LPDN PRP<br><220><br><221> polyA_signal<br><222> (4560) . . . (4686)<br><223> Rabbit beta globin polyA<br><220><br><221> repeat_region<br><222> (4775) . . . (4904)<br><223> 3'ITR |
| 35 | <223> C4/UbC hIL2 BuChE11 IRES PRIMA<br><220><br><221> repeat_region<br><222> (1) . . . (130)<br><223> 5'ITR<br><220><br><221> enhancer<br><222> (279) . . . (538)<br><223> C4 enhancer with 2 mismatches<br><220><br><221> promoter<br><222> (565) . . . (1791)<br><223> UbC promoter<br><220><br><221> misc_feature<br><222> (1826) . . . (3624)<br><223> hBChE coding sequence C1<br><220><br><221> misc_signal<br><222> (1835) . . . (1891)<br><223> human IL2 leader sequence<br><220><br><221> misc_feature<br><222> (3625) . . . (4215)<br><223> IRES<br><220><br><221> misc_feature<br><222> (4220) . . . (4460)<br><223> PRIMA1 PRP<br><220><br><221> polyA_signal<br><222> (4521) . . . (4647)<br><223> Rabbit beta globin polyA<br><220><br><221> repeat_region<br><222> (4736) . . . (4865)<br><223> 3'ITR |
| 36 | <223> hBChE C4<br><220><br><221> misc_feature<br><222> (1) . . . (25)<br><223> ITR<br><220><br><221> misc_feature<br><222> (87) . . . (828)<br><223> human CMV IE enhancer and promoter<br><220><br><221> TATA_signal<br><222> (793) . . . (797)<br><220><br><221> Intron<br><222> (943) . . . (1075)<br><223> Promega chimeric intron<br><220><br><221> misc_feature<br><222> (1189) . . . (2993)<br><223> hBChE C4 |

-continued

| SEQ ID NO: (containing free text) | Free text under <223> |
|---|---|
| | <220><br><221> misc_feature<br><222> (2991) . . . (3581)<br><223> IRES<br><220><br><221> misc_feature<br><222> (3586) . . . (3826)<br><223> PRIMA1 PRP<br><220><br><221> polyA<br><222> (3829) . . . (4060)<br><223> SV40 late polyA<br><220><br><221> misc_feature<br><222> (4125) . . . (4254)<br><223> ITR |
| 37 | <223> CMV.hBChE C5.IRES.PRIMA1.<br><220><br><221> misc_feature<br><222> (87) . . . (828)<br><223> human CMV IE enahncer promoter<br><220><br><221> TATA_signal<br><222> (793) . . . (797)<br><220><br><221> Intron<br><222> (943) . . . (1075)<br><223> promoga chimeric intron<br><220><br><221> misc_feature<br><222> (1189) . . . (2993)<br><223> hBChE C5<br><220><br><221> misc_feature<br><222> (2991) . . . (3581)<br><223> IRES<br><220><br><221> misc_feature<br><222> (3586) . . . (3826)<br><223> PRIMA1 PRP<br><220><br><221> polyA_signal<br><222> (3829) . . . (4060)<br><223> SV40 late polyA<br><220><br><221> misc_feature<br><222> (4125) . . . (4254)<br><223> ITR |
| 38 | <223> CMV.hBChE C7.IRES.PRIMA1<br><220><br><221> misc_feature<br><222> (87) . . . (828)<br><223> human CMV IE enhancer/promoter<br><220><br><221> TATA_signal<br><222> (793) . . . (797)<br><220><br><221> Intron<br><222> (943) . . . (1075)<br><223> Promega chimeric intron<br><220><br><221> misc_feature<br><222> (1189) . . . (2993)<br><223> hBChE C7<br><220><br><221> misc_feature<br><222> (2991) . . . (3581)<br><223> IRES<br><220><br><221> misc_feature<br><222> (3586) . . . (3826)<br><223> PRIMA1 PRP<br><220><br><221> polyA_signal<br><222> (3829) . . . (4060)<br><223> SV40 late polyA signal |

-continued

| SEQ ID NO: (containing free text) | Free text under <223> |
|---|---|
| | <220><br><221> misc_feature<br><222> (4125) . . . (4254)<br><223> ITR |
| 39 | <223> hBChE plasmid<br><220><br><221> misc_feature<br><222> (87) . . . (828)<br><223> human CMV IE enhancer/promoter<br><220><br><221> TATA_signal<br><222> (793) . . . (797)<br><220><br><221> Intron<br><222> (943) . . . (1075)<br><223> Promega chimeric intron<br><220><br><221> misc_feature<br><222> (1144) . . . (1189)<br><223> c-myc mini-IRES<br><220><br><221> misc_feature<br><222> (1190) . . . (2991)<br><223> hBChE C117H E197Q with human IL2 leader sequence<br><220><br><221> misc_feature<br><222> (2992) . . . (3581)<br><223> IRES<br><220><br><221> polyA_signal<br><222> (3829) . . . (4060)<br><223> SV40 late polyA<br><220><br><221> misc_feature<br><222> (4125) . . . (4254)<br><223> ITR |
| 40 | <223> CMV.hBChE C2.IRES.PRIMA1<br><220><br><221> misc_feature<br><222> (1) . . . (130)<br><223> 5'ITR<br><220><br><221> misc_feature<br><222> (191) . . . (932)<br><223> human CMV IE enhancer/promoer<br><220><br><221> TATA_signal<br><222> (897) . . . (901)<br><220><br><221> Intron<br><222> (1047) . . . (1179)<br><223> Promega chimeric intron (PI)<br><220><br><221> misc_feature<br><222> (1293) . . . (3097)<br><223> BuChE C2<br><220><br><221> misc_feature<br><222> (3095) . . . (3685)<br><223> IRES |

-continued

| SEQ ID NO: (containing free text) | Free text under <223> |
|---|---|
| | <220><br><221> misc_feature<br><222> (3690) . . . (3930)<br><223> PRIMA1 PRP<br><220><br><221> polyA_signal<br><222> (3933) . . . (4164)<br><223> SV40 polyA<br><220><br><221> misc_feature<br><222> (4229) . . . (4358)<br><223> 3'ITR |
| 41 | <223> Proline-rich peptide domain |
| 47 | <223> AAV8 capsid |
| 50 | <223> CB7 promoter |
| 51 | <223> C4/UbC.hIL2.BChE C1.IRES.PRIMA.RBG<br><220><br><221> repeat_region<br><222> (1) . . . (130)<br><223> 5'ITR<br><220><br><221> enhancer<br><222> (279) . . . (538)<br><223> C4 enhancer with 2 mismatches<br><220><br><221> promoter<br><222> (565) . . . (1793)<br><223> UbC promoter<br><220><br><221> misc_feature<br><222> (1828) . . . (3626)<br><223> BChE C1 with human IL2 leader<br><220><br><221> misc_feature<br><222> (1837) . . . (1893)<br><223> human IL2 leader<br><220><br><221> misc_feature<br><222> (3627) . . . (4217)<br><223> IRES<br><220><br><221> misc_feature<br><222> (4222) . . . (4447)<br><223> PRIMAl<br><220><br><221> polyA_signal<br><222> (4508) . . . (4634)<br><223> Rabbit beta globin polyA<br><220><br><221> repeat_region<br><222> (4723) . . . (4852) |

All publications cited in this specification and the appended Sequence Listing are incorporated herein by reference. Also incorporated by reference are U.S. Provisional Patent Application No. 62/323,781, filed Apr. 17, 2016 and U.S. Provisional Patent Application No. 62/331,262, filed May 3, 2016. While the invention has been described with reference to particular embodiments, it will be appreciated that modifications can be made without departing from the spirit of the invention. Such modifications are intended to fall within the scope of the appended claims.

The invention claimed is:

1. A replication-defective, recombinant AAV (rAAV) which comprises an AAV capsid having a vector genome packaged therein, said vector genome comprising:
(a) an AAV 5' ITR;
(b) a promoter;
(c) a 5' UTR;
(d) a first leader sequence operably linked to a codon optimized human butyrlcholinesterase (hBChE) coding sequence, wherein the codon optimized hBChE coding sequence is selected from SEQ ID NOs: 6, 7, 8, 9, 3, 4, 5, 10, 11, 12 or 13;
(e) a linker;
(f) a second leader sequence operably linked to a codon optimized nucleic acid sequence encoding a proline rich peptide;
(g) an optional 3'UTR;
(h) a polyA; and
(i) an AAV3' ITR.

2. The rAAV according to claim 1, wherein the leader sequences for expression of hBChE and PRP are selected from a human interleukin-2 leader or a native hBChE leader sequence.

3. The rAAV according to claim 1, wherein the origin of the proline rich peptide is from Proline-rich membrane anchor 1 (Primal) and lamellipodin (LPDN).

4. The rAAV according to claim 1, wherein the second leader sequence is the same as the leader sequence which is operably linked to the BChE coding sequence.

5. The rAAV according to claim 1, wherein the linker is an F2A.

6. The rAAV according to claim 1, wherein the linker is an IRES.

7. The rAAV according to claim 1, wherein the vector genome further comprises a 3' UTR sequence.

8. The rAAV according to claim 7, wherein the 3' UTR is a woodchuck post-transcription regulatory element.

9. The rAAV according to claim 1, wherein the polyA is SV40 or rabbit beta globin.

10. The rAAV according to claim 1, wherein the vector genome comprises an expression cassette comprising one of:
(a) SEQ ID NO: 34 (C4/UbC-hIL2-BchE C1-IRES-LPDN);
(b) nt 14 to nt 4162 of SEQ ID NO: 30 (UbC-cmyc-IL2-BChE C1-IRES-IL2-PRIMA1);
(c) nt 14 to nt 4874 of SEQ ID NO: 31 (UbC-cmyc-IL2-BChE C1-IRES-IL2-LPDN);
(d) SEQ ID NO: 32 (CB7-cmyc-IL2-BChE C1-IRES-IL2-PRIMA1);
(e) SEQ ID NO: 33 (CB7-cmyc-IL2-BChE C1-IRES-IL2-LPDN); or
(f) SEQ ID NO: 35 (C4/UbC-hIL2-BChE C1-IRES-PRIMA1).

11. The rAAV according to claim 1, wherein the AAV capsid has tropism for skeletal muscle.

12. The rAAV according to claim 1, wherein the AAV capsid is AAV8.

13. An aqueous liquid suspension comprising an rAAV according to claim 1 and an aqueous suspension base.

* * * * *

```
SEQUENCE LISTING

<160> NUMBER OF SEQ ID NOS: 51

<210> SEQ ID NO 1
<211> LENGTH: 602
<212> TYPE: PRT
<213> ORGANISM: Homo sapiens
```

-continued

<220> FEATURE:
<221> NAME/KEY: MISC_FEATURE
<222> LOCATION: (1)..(26)
<223> OTHER INFORMATION: Innate leader/signal peptide/sequence
<220> FEATURE:
<221> NAME/KEY: mat_peptide
<222> LOCATION: (27)..(602)

<400> SEQUENCE: 1

```
Met His Ser Lys Val Thr Ile Ile Cys Ile Arg Phe Leu Phe Trp Phe
    -25                 -20                 -15

Leu Leu Leu Cys Met Leu Ile Gly Lys Ser His Thr Glu Asp Asp Ile
-10                 -5                  -1  1               5

Ile Ile Ala Thr Lys Asn Gly Lys Val Arg Gly Met Asn Leu Thr Val
            10                  15                  20

Phe Gly Gly Thr Val Thr Ala Phe Leu Gly Ile Pro Tyr Ala Gln Pro
        25                  30                  35

Pro Leu Gly Arg Leu Arg Phe Lys Lys Pro Gln Ser Leu Thr Lys Trp
    40                  45                  50

Ser Asp Ile Trp Asn Ala Thr Lys Tyr Ala Asn Ser Cys Cys Gln Asn
55                  60                  65                  70

Ile Asp Gln Ser Phe Pro Gly Phe His Gly Ser Glu Met Trp Asn Pro
                75                  80                  85

Asn Thr Asp Leu Ser Glu Asp Cys Leu Tyr Leu Asn Val Trp Ile Pro
            90                  95                  100

Ala Pro Lys Pro Lys Asn Ala Thr Val Leu Ile Trp Ile Tyr Gly Gly
        105                 110                 115

Gly Phe Gln Thr Gly Thr Ser Ser Leu His Val Tyr Asp Gly Lys Phe
    120                 125                 130

Leu Ala Arg Val Glu Arg Val Ile Val Val Ser Met Asn Tyr Arg Val
135                 140                 145                 150

Gly Ala Leu Gly Phe Leu Ala Leu Pro Gly Asn Pro Glu Ala Pro Gly
                155                 160                 165

Asn Met Gly Leu Phe Asp Gln Gln Leu Ala Leu Gln Trp Val Gln Lys
            170                 175                 180

Asn Ile Ala Ala Phe Gly Gly Asn Pro Lys Ser Val Thr Leu Phe Gly
        185                 190                 195

Glu Ser Ala Gly Ala Ala Ser Val Ser Leu His Leu Leu Ser Pro Gly
    200                 205                 210

Ser His Ser Leu Phe Thr Arg Ala Ile Leu Gln Ser Gly Ser Phe Asn
215                 220                 225                 230

Ala Pro Trp Ala Val Thr Ser Leu Tyr Glu Ala Arg Asn Arg Thr Leu
                235                 240                 245

Asn Leu Ala Lys Leu Thr Gly Cys Ser Arg Glu Asn Glu Thr Glu Ile
            250                 255                 260

Ile Lys Cys Leu Arg Asn Lys Asp Pro Gln Glu Ile Leu Leu Asn Glu
        265                 270                 275

Ala Phe Val Val Pro Tyr Gly Thr Pro Leu Ser Val Asn Phe Gly Pro
    280                 285                 290

Thr Val Asp Gly Asp Phe Leu Thr Asp Met Pro Asp Ile Leu Leu Glu
295                 300                 305                 310

Leu Gly Gln Phe Lys Lys Thr Gln Ile Leu Val Gly Val Asn Lys Asp
                315                 320                 325

Glu Gly Thr Ala Phe Leu Val Tyr Gly Ala Pro Gly Phe Ser Lys Asp
            330                 335                 340
```

```
Asn Asn Ser Ile Ile Thr Arg Lys Glu Phe Gln Glu Gly Leu Lys Ile
        345                 350                 355

Phe Phe Pro Gly Val Ser Glu Phe Gly Lys Glu Ser Ile Leu Phe His
    360                 365                 370

Tyr Thr Asp Trp Val Asp Asp Gln Arg Pro Glu Asn Tyr Arg Glu Ala
375                 380                 385                 390

Leu Gly Asp Val Val Gly Asp Tyr Asn Phe Ile Cys Pro Ala Leu Glu
                395                 400                 405

Phe Thr Lys Lys Phe Ser Glu Trp Gly Asn Asn Ala Phe Phe Tyr Tyr
            410                 415                 420

Phe Glu His Arg Ser Ser Lys Leu Pro Trp Pro Glu Trp Met Gly Val
        425                 430                 435

Met His Gly Tyr Glu Ile Glu Phe Val Phe Gly Leu Pro Leu Glu Arg
    440                 445                 450

Arg Asp Asn Tyr Thr Lys Ala Glu Glu Ile Leu Ser Arg Ser Ile Val
455                 460                 465                 470

Lys Arg Trp Ala Asn Phe Ala Lys Tyr Gly Asn Pro Asn Glu Thr Gln
                475                 480                 485

Asn Asn Ser Thr Ser Trp Pro Val Phe Lys Ser Thr Glu Gln Lys Tyr
            490                 495                 500

Leu Thr Leu Asn Thr Glu Ser Thr Arg Ile Met Thr Lys Leu Arg Ala
        505                 510                 515

Gln Gln Cys Arg Phe Trp Thr Ser Phe Phe Pro Lys Val Leu Glu Met
    520                 525                 530

Thr Gly Asn Ile Asp Glu Ala Glu Trp Glu Trp Lys Ala Gly Phe His
535                 540                 545                 550

Arg Trp Asn Asn Tyr Met Met Asp Trp Lys Asn Gln Phe Asn Asp Tyr
                555                 560                 565

Thr Ser Lys Lys Glu Ser Cys Val Gly Leu
            570                 575
```

<210> SEQ ID NO 2
<211> LENGTH: 2416
<212> TYPE: DNA
<213> ORGANISM: Homo sapiens

<400> SEQUENCE: 2

```
tactgaatgt cagtgcagtc caatttacag gctggagcag cagctgcatc ctgcatttcc      60

ccgaagtatt acatgatttt cactccttgc aaactttacc atctttgttg cagagaatcg     120

gaaatcaata tgcatagcaa agtcacaatc atatgcatca gatttctctt ttggtttctt     180

ttgctctgca tgcttattgg gaagtcacat actgaagatg acatcataat tgcaacaaag     240

aatggaaaag tcagagggat gaacttgaca gtttttggtg gcacggtaac agcctttctt     300

ggaattccct atgcacagcc acctcttggt agacttcgat tcaaaaagcc acagtctctg     360

accaagtggt ctgatatttg gaatgccaca aaatatgcaa attcttgctg tcagaacata     420

gatcaaagtt ttccaggctt ccatggatca gagatgtgga acccaaacac tgacctcagt     480

gaagactgtt tatatctaaa tgtatggatt ccagcaccta aaccaaaaaa tgccactgta     540

ttgatatgga tttatggtgg tggttttcaa actggaacat catctttaca tgtttatgat     600

ggcaagtttc tggctcgggt tgaaagagtt attgtagtgt caatgaacta tagggtgggt     660

gccctaggat tcttagcttt gccaggaaat cctgaggctc cagggaacat gggtttattt     720

gatcaacagt tggctcttca gtgggttcaa aaaaatatag cagcctttgg tggaaatcct     780
```

aaaagtgtaa ctctctttgg agaaagtgca ggagcagctt cagttagcct gcatttgctt 840
tctcctggaa gccattcatt gttcaccaga gccattctgc aaagtggatc ctttaatgct 900
ccttgggcgg taacatctct ttatgaagct aggaacagaa cgttgaactt agctaaattg 960
actggttgct ctagagagaa tgagactgaa ataatcaagt gtcttagaaa taaagatccc 1020
caagaaattc ttctgaatga agcatttgtt gtcccctatg ggactccttt gtcagtaaac 1080
tttggtccga ccgtggatgg tgattttctc actgacatgc cagacatatt acttgaactt 1140
ggacaattta aaaaaaccca gattttggtg ggtgttaata aagatgaagg gacagctttt 1200
ttagtctatg gtgctcctgg cttcagcaaa gataacaata gtatcataac tagaaaagaa 1260
tttcaggaag gtttaaaaat attttttcca ggagtgagtg agtttggaaa ggaatccatc 1320
ctttttcatt acacagactg ggtagatgat cagagacctg aaaactaccg tgaggccttg 1380
ggtgatgttg ttggggatta taatttcata tgccctgcct tggagttcac caagaagttc 1440
tcagaatggg gaaataatgc ctttttctac tattttgaac accgatcctc caaacttccg 1500
tggccagaat ggatgggagt gatgcatggc tatgaaattg aatttgtctt tggtttacct 1560
ctggaaagaa gagataatta cacaaaagcc gaggaaattt tgagtagatc catagtgaaa 1620
cggtgggcaa attttgcaaa atatgggaat ccaaatgaga ctcagaacaa tagcacaagc 1680
tggcctgtct tcaaaagcac tgaacaaaaa tatctaacct tgaatacaga gtcaacaaga 1740
ataatgacga aactacgtgc tcaacaatgt cgattctgga catcattttt tccaaaagtc 1800
ttggaaatga caggaaatat tgatgaagca gaatgggagt ggaaagcagg attccatcgc 1860
tggaacaatt acatgatgga ctggaaaaat caatttaacg attacactag caagaaagaa 1920
agttgtgtgg gtctctaatt aatagattta ccctttatag aacatatttt cctttagatc 1980
aaggcaaaaa tatcaggagc tttttttacac acctactaaa aaagttatta tgtagctgaa 2040
acaaaaatgc cagaaggata atattgattc ctcacatctt taacttagta ttttacctag 2100
catttcaaaa cccaaatggc tagaacatgt ttaattaaat ttcacaatat aaagttctac 2160
agttaattat gtgcatatta aaacaatggc ctggttcaat ttctttcttt ccttaataaa 2220
tttaagtttt ttccccccaa aattatcagt gctctgcttt tagtcacgtg tattttcatt 2280
accactcgta aaaaggtatc ttttttaaat gaattaaata ttgaaacact gtacaccata 2340
gtttacaata ttatgtttcc taattaaaat aagaattgaa tgtcaatatg agatattaaa 2400
ataagcacag aaaatc 2416

<210> SEQ ID NO 3
<211> LENGTH: 1832
<212> TYPE: DNA
<213> ORGANISM: Artificial Sequence
<220> FEATURE:
<223> OTHER INFORMATION: human BChE C0 with innate leader peptide.

<400> SEQUENCE: 3
tctagaccca ccatgcacag caaggtgacc atcatctgca tccggttcct gttctggttc 60
ctgctgctgt gcatgctgat cggaaagagc cacaccgagg atgatatcat catcgccacc 120
aagaacggaa aggtgcgggg aatgaacctg accgtgttcg gaggaaccgt gaccgccttc 180
ctgggaatcc catacgccca gccaccactg ggacggctgc ggttcaagaa gccacagagc 240
ctgaccaagt ggagcgatat ctggaacgcc accaagtacg ccaacagctg ctgccagaac 300
atcgatcaga gcttcccagg attccacgga agcgagatgt ggaacccaaa caccgatctg 360
agcgaggatt gcctgtacct gaacgtgtgg atcccagccc caaagccaaa gaacgccacc 420
gtgctgatct ggatctacgg aggaggattc cagaccggaa ccagcagcct gcacgtgtac 480
gatggaaagt tcctggcccg ggtggagcgg gtgatcgtgg tgagcatgaa ctaccgggtg 540
ggagccctgg gattcctggc cctgccagga aacccagagg ccccaggaaa catgggactg 600
ttcgatcagc agctggccct gcagtgggtg cagaagaaca tcgccgcctt cggaggaaac 660
ccaaagagcg tgaccctgtt cggagagagc gccggagccg ccagcgtgag cctgcacctg 720
ctgagcccag gaagccacag cctgttcacc cgggccatcc tgcagagcgg aagcttcaac 780
gccccatggg ccgtgaccag cctgtacgag gcccggaacc ggaccctgaa cctggccaag 840
ctgaccggat gcagccggga gaacgagacc gagatcatca agtgcctgcg gaacaaggat 900
ccacaggaga tcctgctgaa cgaggccttc gtggtgccat acggaacccc actgagcgtg 960
aacttcggac caaccgtgga tggagatttc ctgaccgata tgccagatat cctgctggag 1020
ctgggacagt tcaagaagac ccagatcctg gtgggagtga acaaggatga gggaaccgcc 1080
ttcctggtgt acggagcccc aggattcagc aaggataaca acagcatcat cacccggaag 1140
gagttccagg agggactgaa gatcttcttc ccaggagtga gcgagttcgg aaaggagagc 1200
atcctgttcc actacaccga ttgggtggat gatcagcggc cagagaacta ccgggaggcc 1260
ctgggagatg tggtgggaga ttacaacttc atctgcccag ccctggagtt caccaagaag 1320
ttcagcgagt ggggaaacaa cgccttcttc tactacttcg agcaccggag cagcaagctg 1380
ccatggccag agtggatggg agtgatgcac ggatacgaga tcgagttcgt gttcggactg 1440
ccactggagc ggcgggataa ctacaccaag gccgaggaga tcctgagccg gagcatcgtg 1500
aagcggtggg ccaacttcgc caagtacgga aacccaaacg agacccagaa caacagcacc 1560
agctggccag tgttcaagag caccgagcag aagtacctga ccctgaacac cgagagcacc 1620
cggatcatga ccaagctgcg ggcccagcag tgccggttct ggaccagctt cttcccaaag 1680
gtgctggaga tgaccggaaa catcgatgag gccgagtggg agtggaaggc cggattccac 1740
cggtggaaca actacatgat ggattggaag aaccagttca acgattacac cagcaagaag 1800
gagagctgcg tgggactgtg ataaggccgg cc 1832

<210> SEQ ID NO 4
<211> LENGTH: 1803
<212> TYPE: DNA
<213> ORGANISM: Artificial Sequence
<220> FEATURE:
<223> OTHER INFORMATION: human BChE C0 with IL2 leader peptide.

<400> SEQUENCE: 4
tctagaccca ccatgcggat gcagctgctg ctgctgatcg ccctgagcct ggccctggtg 60
accaacagcg aggatgatat catcatcgcc accaagaacg gaaaggtgcg gggaatgaac 120
ctgaccgtgt tcggaggaac cgtgaccgcc ttcctgggaa tcccatacgc ccagccacca 180
ctgggacggc tgcggttcaa gaagccacag agcctgacca agtggagcga tatctggaac 240
gccaccaagt acgccaacag ctgctgccag aacatcgatc agagcttccc aggattccac 300
ggaagcgaga tgtggaaccc aaacaccgat ctgagcgagg attgcctgta cctgaacgtg 360
tggatcccag ccccaaagcc aaagaacgcc accgtgctga tctggatcta cggaggagga 420
ttccagaccg gaaccagcag cctgcacgtg tacgatggaa agttcctggc ccgggtggag 480
cgggtgatcg tggtgagcat gaactaccgg gtgggagccc tgggattcct ggccctgcca 540
ggaaacccag aggccccagg aaacatggga ctgttcgatc agcagctggc cctgcagtgg 600

-continued gtgcagaaga acatcgccgc cttcggagga aacccaaaga gcgtgaccct gttcggagag 660
agcgccggag ccgccagcgt gagcctgcac ctgctgagcc caggaagcca cagcctgttc 720
acccgggcca tcctgcagag cggaagcttc aacgccccat gggccgtgac cagcctgtac 780
gaggcccgga accggaccct gaacctggcc aagctgaccg gatgcagccg ggagaacgag 840
accgagatca tcaagtgcct gcggaacaag gatccacagg agatcctgct gaacgaggcc 900
ttcgtggtgc catacggaac ccccactgagc gtgaacttcg gaccaaccgt ggatggagat 960
ttcctgaccg atatgccaga tatcctgctg gagctgggac agttcaagaa gacccagatc 1020
ctggtgggag tgaacaagga tgagggaacc gccttcctgg tgtacggagc cccaggattc 1080
agcaaggata acaacagcat catcacccgg aaggagttcc aggagggact gaagatcttc 1140
ttcccaggag tgagcgagtt cggaaaggag agcatcctgt tccactacac cgattgggtg 1200
gatgatcagc ggccagagaa ctaccgggag gccctgggag atgtggtggg agattacaac 1260
ttcatctgcc cagccctgga gttcaccaag aagttcagcg agtggggaaa caacgccttc 1320
ttctactact tcgagcaccg gagcagcaag ctgccatggc cagagtggat gggagtgatg 1380
cacggatacg agatcgagtt cgtgttcgga ctgccactgg agcggcggga taactacacc 1440
aaggccgagg agatcctgag ccggagcatc gtgaagcggt gggccaactt cgccaagtac 1500
ggaaacccaa acgagaccca gaacaacagc accagctggc cagtgttcaa gagcaccgag 1560
cagaagtacc tgaccctgaa caccgagagc acccggatca tgaccaagct gcgggcccag 1620
cagtgccggt tctggaccag cttcttccca aaggtgctgg agatgaccgg aaacatcgat 1680
gaggccgagt gggagtggaa ggccggattc caccggtgga acaactacat gatggattgg 1740
aagaaccagt tcaacgatta caccagcaag aaggagagct gcgtgggact gtgataaggc 1800
cgg 1803

<210> SEQ ID NO 5
<211> LENGTH: 1802
<212> TYPE: DNA
<213> ORGANISM: Artificial Sequence
<220> FEATURE:
<223> OTHER INFORMATION: human BChE C1 with IL2 leader peptide.
<220> FEATURE:
<221> NAME/KEY: sig_peptide
<222> LOCATION: (11)..(67)
<223> OTHER INFORMATION: IL2

<400> SEQUENCE: 5
ctagacccac catgcggatg cagctgctgc tgctgattgc tctgagcctg gctctggtga 60
ccaacagcga agacgacatt attattgcta ccaagaacgg caaggtgcgg ggcatgaacc 120
tgaccgtgtt tggcggcacc gtgaccgctt ttctgggcat tccctatgct cagccccccc 180
tgggccggct gcggtttaag aagccccaga gcctgaccaa gtggagcgac atttggaacg 240
ctaccaagta tgctaacagc tgttgtcaga acattgacca gagctttccc ggctttcatg 300
gcagcgaaat gtggaacccc aacaccgacc tgagcgaaga ctgtctgtat ctgaacgtgt 360
ggattcccgc tcccaagccc aagaacgcta ccgtgctgat ttggatttat ggcggcggct 420
ttcagaccgg caccagcagc ctgcatgtgt atgacggcaa gtttctggct cgggtggaac 480
gggtgattgt ggtgagcatg aactatcggg tgggcgctct gggctttctg gctctgcccg 540
gcaaccccga agctcccggc aacatgggcc tgtttgacca gcagctggct ctgcagtggg 600
tgcagaagaa cattgctgct tttggcggca accccaagag cgtgaccctg tttggcgaaa 660
gcgctggcgc tgctagcgtg agcctgcatc tgctgagccc cggcagccat agcctgttta 720

```
cccgggctat tctgcagagc ggcagcttta acgctccctg ggctgtgacc agcctgtatg    780

aagctcggaa ccggaccctg aacctggcta agctgaccgg ctgtagccgg gaaaacgaaa    840

ccgaaattat taagtgtctg cggaacaagg acccccagga aattctgctg aacgaagctt    900

ttgtggtgcc ctatggcacc cccctgagcg tgaactttgg ccccaccgtg gacggcgact    960

ttctgaccga catgcccgac attctgctgg aactgggcca gtttaagaag acccagattc   1020

tggtgggcgt gaacaaggac gaaggcaccg cttttctggt gtatggcgct cccggcttta   1080

gcaaggacaa caacagcatt attacccgga aggaatttca ggaaggcctg aagatttttt   1140

ttcccggcgt gagcgaattt ggcaaggaaa gcattctgtt tcattatacc gactgggtgg   1200

acgaccagcg gcccgaaaac tatcgggaag ctctgggcga cgtggtgggc gactataact   1260

ttatttgtcc cgctctggaa tttaccaaga agtttagcga atggggcaac aacgcttttt   1320

tttattattt tgaacatcgg agcagcaagc tgccctggcc cgaatggatg ggcgtgatgc   1380

atggctatga aattgaattt gtgtttggcc tgcccctgga acggcgggac aactatacca   1440

aggctgaaga aattctgagc cggagcattg tgaagcggtg ggctaacttt gctaagtatg   1500

gcaaccccaa cgaaacccag aacaacagca ccagctggcc cgtgtttaag agcaccgaac   1560

agaagtatct gaccctgaac accgaaagca cccggattat gaccaagctg cgggctcagc   1620

agtgtcggtt ttggaccagc ttttttccca aggtgctgga aatgaccggc aacattgacg   1680

aagctgaatg ggaatggaag gctggctttc atcggtggaa caactatatg atggactgga   1740

agaaccagtt taacgactat accagcaaga aggaaagctg tgtgggcctg tgataaggcc   1800

gg                                                                  1802
```

<210> SEQ ID NO 6
<211> LENGTH: 1805
<212> TYPE: DNA
<213> ORGANISM: Artificial Sequence
<220> FEATURE:
<223> OTHER INFORMATION: human BChE C2 with IL2 leader peptide.

<400> SEQUENCE: 6

```
tctagaccca ccatgagaat gcaattgttg ttgttgattg cattgtcatt ggcattggtg     60

acaaattcag aagatgatat tattattgca acaaaaaatg gtaaagtgag aggtatgaat    120

ttgacagtgt ttggtggtac agtgacagca tttttgggta ttccatatgc acaaccacca    180

ttgggtagat tgagatttaa aaaaccacaa tcattgacaa aatggtcaga tatttggaat    240

gcaacaaaat atgcaaattc atgttgtcaa aatattgatc aatcatttcc aggttttcat    300

ggttcagaaa tgtggaatcc aaatacagat ttgtcagaag attgtttgta tttgaatgtg    360

tggattccag caccaaaacc aaaaaatgca acagtgttga tttggattta tggtggtggt    420

tttcaaacag gtacatcatc attgcatgtg tatgatggta aatttttggc aagagtggaa    480

agagtgattg tggtgtcaat gaattataga gtgggtgcat tgggtttttt ggcattgcca    540

ggtaatccag aagcaccagg taatatgggt ttgtttgatc aacaattggc attgcaatgg    600

gtgcaaaaaa atattgcagc atttggtggt aatccaaaat cagtgacatt gtttggtgaa    660

tcagcaggtg cagcatcagt gtcattgcat ttgttgtcac caggttcaca ttcattgttt    720

acaagagcaa ttttgcaatc aggttcattt aatgcaccat gggcagtgac atcattgtat    780

gaagcaagaa atagaacatt gaatttggca aaattgacag gttgttcaag agaaaatgaa    840

acagaaatta ttaaatgttt gagaaataaa gatccacaag aaattttgtt gaatgaagca    900
```

-continued

```
tttgtggtgc catatggtac accattgtca gtgaattttg gtccaacagt ggatggtgat    960

tttttgacag atatgccaga tattttgttg gaattgggtc aatttaaaaa aacacaaatt   1020

ttggtgggtg tgaataaaga tgaaggtaca gcatttttgg tgtatggtgc accaggtttt   1080

tcaaaagata ataattcaat tattacaaga aaagaatttc aagaaggttt gaaaattttt   1140

tttccaggtg tgtcagaatt tggtaaagaa tcaattttgt ttcattatac agattgggtg   1200

gatgatcaaa gaccagaaaa ttatagagaa gcattgggtg atgtggtggg tgattataat   1260

tttatttgtc cagcattgga atttacaaaa aaattttcag aatggggtaa taatgcattt   1320

ttttattatt ttgaacatag atcatcaaaa ttgccatggc cagaatggat gggtgtgatg   1380

catggttatg aaattgaatt tgtgtttggt ttgccattgg aaagaagaga taattataca   1440

aaagcagaag aaattttgtc aagatcaatt gtgaaaagat gggcaaattt tgcaaaatat   1500

ggtaatccaa atgaaacaca aaataattca acatcatggc cagtgtttaa atcaacagaa   1560

caaaaatatt tgacattgaa tacagaatca acaagaatta tgacaaaatt gagagcacaa   1620

caatgtagat tttggacatc atttttttcca aaagtgttgg aaatgacagg taatattgat   1680

gaagcagaat gggaatggaa agcaggtttt catagatgga ataattatat gatggattgg   1740

aaaaatcaat ttaatgatta tacatcaaaa aaagaatcat gtgtgggttt gtgataaggc   1800

cggcc                                                               1805
```

<210> SEQ ID NO 7
<211> LENGTH: 1805
<212> TYPE: DNA
<213> ORGANISM: Artificial Sequence
<220> FEATURE:
<223> OTHER INFORMATION: human BChE C3 with IL2 leader peptide.

<400> SEQUENCE: 7

```
tctagaccca ccatgagaat gcagcttctt cttcttatcg ctcttagcct tgctcttgtg     60

acaaacagcg aagatgatat catcatcgct acaaagaacg ggaaggtgag agggatgaac    120

cttacagtgt ttgggggggac agtgacagct tttcttggga tcccttatgc tcagcctcct    180

cttgggagac ttagatttaa gaagcctcag agccttacaa agtggagcga tatctggaac    240

gctacaaagt atgctaacag ctgttgtcag aacatcgatc agagctttcc tgggtttcac    300

gggagcgaaa tgtggaaccc taacacagat cttagcgaag attgtcttta tcttaacgtg    360

tggatccctg ctcctaagcc taagaacgct acagtgctta tctggatcta tggggggggg    420

tttcagacag ggacaagcag ccttcacgtg tatgatggga agtttcttgc tagagtggaa    480

agagtgatcg tggtgagcat gaactataga gtgggggctc ttgggtttct tgctcttcct    540

gggaaccctg aagctcctgg gaacatgggg ctttttgatc agcagcttgc tcttcagtgg    600

gtgcagaaga acatcgctgc ttttgggggg aaccctaaga gcgtgacact tttggggaa    660

agcgctgggg ctgctagcgt gagccttcac cttcttagcc ctgggagcca cagccttttt    720

acaagagcta tccttcagag cgggagcttt aacgctcctt gggctgtgac aagcctttat    780

gaagctagaa acagaacact taaccttgct aagcttacag ggtgtagcag agaaaacgaa    840

acagaaatca tcaagtgtct tagaaacaag gatcctcagg aaatccttct taacgaagct    900

tttgtggtgc cttatgggac acctcttagc gtgaactttg ggcctacagt ggatggggat    960

tttcttacag atatgcctga tatccttctt gaacttgggc agtttaagaa gacacagatc   1020

cttgtggggg tgaacaagga tgaagggaca gcttttcttg tgtatggggc tcctgggttt   1080

agcaaggata acaacagcat catcacaaga aaggaatttc aggaagggct taagatcttt   1140
```

```
tttcctgggg tgagcgaatt tgggaaggaa agcatccttt ttcactatac agattgggtg   1200

gatgatcaga gacctgaaaa ctatagagaa gctcttgggg atgtggtggg ggattataac   1260

tttatctgtc ctgctcttga atttacaaag aagtttagcg aatgggggaa caacgctttt   1320

ttttattatt ttgaacacag aagcagcaag cttccttggc ctgaatggat gggggtgatg   1380

cacgggtatg aaatcgaatt tgtgtttggg cttcctcttg aaagaagaga taactataca   1440

aaggctgaag aaatccttag cagaagcatc gtgaagagat gggctaactt tgctaagtat   1500

gggaacccta acgaaacaca gaacaacagc acaagctggc ctgtgtttaa gagcacagaa   1560

cagaagtatc ttacacttaa cacagaaagc acaagaatca tgacaaagct tagagctcag   1620

cagtgtagat tttggacaag ctttttttcct aaggtgcttg aaatgacagg gaacatcgat   1680

gaagctgaat gggaatggaa ggctgggttt cacagatgga acaactatat gatggattgg   1740

aagaaccagt ttaacgatta tacaagcaag aaggaaagct gtgtggggct ttgataaggc   1800

cggcc                                                               1805
```

```
<210> SEQ ID NO 8
<211> LENGTH: 1805
<212> TYPE: DNA
<213> ORGANISM: Artificial Sequence
<220> FEATURE:
<223> OTHER INFORMATION: human BChE C4 with IL2 leader peptide.

<400> SEQUENCE: 8

tctagaccca ccatgagaat gcaacttctt cttcttattg cactttcact tgcacttgtt     60

acaaattcag aagatgatat tattattgca acaaaaaatg gaaaagttag aggaatgaat    120

cttacagttt tcggaggaac agttacagca ttccttggaa ttccatatgc acaaccacca    180

cttggaagac ttagattcaa aaaaccacaa tcacttacaa aatggtcaga tatttggaat    240

gcaacaaaat atgcaaattc atgttgtcaa aatattgatc aatcattccc aggattccat    300

ggatcagaaa tgtggaatcc aaatacagat ctttcagaag attgtcttta tcttaatgtt    360

tggattccag caccaaaacc aaaaaatgca acagttctta tttggattta tggaggagga    420

ttccaaacag gaacatcatc acttcatgtt tatgatggaa aattccttgc aagagttgaa    480

agagttattg ttgtttcaat gaattataga gttggagcac ttggattcct tgcacttcca    540

ggaaatccag aagcaccagg aaatatggga cttttcgatc aacaacttgc acttcaatgg    600

gttcaaaaaa atattgcagc attcggagga aatccaaaat cagttacact tttcggagaa    660

tcagcaggag cagcatcagt ttcacttcat cttctttcac caggatcaca ttcacttttc    720

acaagagcaa ttcttcaatc aggatcattc aatgcaccat gggcagttac atcactttat    780

gaagcaagaa atagaacact taatcttgca aaacttacag gatgttcaag agaaaatgaa    840

acagaaatta ttaaatgtct tagaaataaa gatccacaag aaattcttct taatgaagca    900

ttcgttgttc catatggaac accactttca gttaatttcg gaccaacagt tgatggagat    960

ttccttacag atatgccaga tattcttctt gaacttggac aattcaaaaa aacacaaatt   1020

cttgttggag ttaataaaga tgaaggaaca gcattccttg tttatggagc accaggattc   1080

tcaaaagata ataattcaat tattacaaga aaagaattcc aagaaggact taaaattttc   1140

ttcccaggag tttcagaatt cggaaaagaa tcaattcttt tccattatac agattgggtt   1200

gatgatcaaa gaccagaaaa ttatagagaa gcacttggag atgttgttgg agattataat   1260

ttcatttgtc cagcacttga attcacaaaa aaattctcag aatggggaaa taatgcattc   1320
```

-continued

```
ttctattatt tcgaacatag atcatcaaaa cttccatggc cagaatggat gggagttatg   1380
catggatatg aaattgaatt cgttttcgga cttccacttg aaagaagaga taattataca   1440
aaagcagaag aaattctttc aagatcaatt gttaaaagat gggcaaattt cgcaaaatat   1500
ggaaatccaa atgaaacaca aaataattca acatcatggc cagttttcaa atcaacagaa   1560
caaaaatatc ttacacttaa tacagaatca acaagaatta tgacaaaact tagagcacaa   1620
caatgtagat tctggacatc attcttccca aaagttcttg aaatgacagg aaatattgat   1680
gaagcagaat gggaatggaa agcaggattc catagatgga ataattatat gatggattgg   1740
aaaaatcaat tcaatgatta tacatcaaaa aaagaatcat gtgttggact ttgataaggc   1800
cggcc                                                               1805
```

<210> SEQ ID NO 9
<211> LENGTH: 1805
<212> TYPE: DNA
<213> ORGANISM: Artificial Sequence
<220> FEATURE:
<223> OTHER INFORMATION: human BChE C5 with IL2 leader peptide.

<400> SEQUENCE: 9

```
tctagaccca ccatgcgtat gcagctgctg ctgctgattg cgctgagcct ggcgctggtg     60
accaacagcg aagatgatat tattattgcg accaaaaacg gcaaagtgcg tggcatgaac    120
ctgaccgtgt ttggcggcac cgtgaccgcg tttctgggca ttccgtatgc gcagccgccg    180
ctgggccgtc tgcgttttaa aaaaccgcag agcctgacca aatggagcga tatttggaac    240
gcgaccaaat atgcgaacag ctgctgccag aacattgatc agagctttcc gggctttcat    300
ggcagcgaaa tgtggaaccc gaacaccgat ctgagcgaag attgcctgta tctgaacgtg    360
tggattccgg cgccgaaacc gaaaaacgcg accgtgctga tttggattta tggcggcggc    420
tttcagaccg gcaccagcag cctgcatgtg tatgatggca aatttctggc gcgtgtggaa    480
cgtgtgattg tggtgagcat gaactatcgt gtgggcgcgc tgggctttct ggcgctgccg    540
ggcaacccgg aagcgccggg caacatgggc ctgtttgatc agcagctggc gctgcagtgg    600
gtgcagaaaa acattgcggc gtttggcggc aacccgaaaa gcgtgaccct gtttggcgaa    660
agcgcgggcg cggcgagcgt gagcctgcat ctgctgagcc cgggcagcca tagcctgttt    720
acccgtgcga ttctgcagag cggcagcttt aacgcgccgt gggcggtgac cagcctgtat    780
gaagcgcgta accgtaccct gaacctggcg aaactgaccg gctgcagccg tgaaaacgaa    840
accgaaatta ttaaatgcct gcgtaacaaa gatccgcagg aaattctgct gaacgaagcg    900
tttgtggtgc cgtatggcac cccgctgagc gtgaactttg gcccgaccgt ggatggcgat    960
tttctgaccg atatgccgga tattctgctg gaactgggcc agtttaaaaa aacccagatt   1020
ctggtgggcg tgaacaaaga tgaaggcacc gcgtttctgg tgtatggcgc gccgggcttt   1080
agcaaagata acaacagcat tattacccgt aaagaatttc aggaaggcct gaaaattttt   1140
tttccgggcg tgagcgaatt tggcaaagaa agcattctgt ttcattatac cgattgggtg   1200
gatgatcagc gtccggaaaa ctatcgtgaa gcgctgggcg atgtggtggg cgattataac   1260
tttatttgcc cggcgctgga atttaccaaa aaatttagcg aatggggcaa caacgcgttt   1320
ttttattatt ttgaacatcg tagcagcaaa ctgccgtggc cggaatggat gggcgtgatg   1380
catggctatg aaattgaatt tgtgtttggc ctgccgctgg aacgtcgtga taactatacc   1440
aaagcggaag aaattctgag ccgtagcatt gtgaaacgtt gggcgaactt tgcgaaatat   1500
ggcaacccga acgaaaccca gaacaacagc accagctggc cggtgtttaa aagcaccgaa   1560
```

```
cagaaatatc tgaccctgaa caccgaaagc acccgtatta tgaccaaact gcgtgcgcag   1620

cagtgccgtt tttggaccag ctttttttccg aaagtgctgg aaatgaccgg caacattgat   1680

gaagcggaat gggaatggaa agcgggcttt catcgttgga acaactatat gatggattgg   1740

aaaaaccagt ttaacgatta taccagcaaa aaagaaagct gcgtgggcct gtgataaggc   1800

cggcc                                                               1805


<210> SEQ ID NO 10
<211> LENGTH: 1805
<212> TYPE: DNA
<213> ORGANISM: Artificial Sequence
<220> FEATURE:
<223> OTHER INFORMATION: human BChE C6 with IL2 leader peptide.

<400> SEQUENCE: 10

tctagaccca ccatgcgaat gcagctgctg ctgctgatcg cactgagcct ggcactggtg     60

accaacagcg aggacgacat catcatcgca accaagaacg gaaaggtgcg aggaatgaac    120

ctgaccgtgt tcggaggaac cgtgaccgca ttcctgggaa tcccatacgc acagccacca    180

ctgggacgac tgcgattcaa gaagccacag agcctgacca agtggagcga catctggaac    240

gcaaccaagt acgcaaacag ctgttgtcag aacatcgacc agagcttccc aggattccat    300

ggaagcgaga tgtggaaccc aaacaccgac ctgagcgagg actgtctgta cctgaacgtg    360

tggatcccag caccaaagcc aaagaacgca accgtgctga tctggatcta cggaggagga    420

ttccagaccg gaaccagcag cctgcatgtg tacgacggaa agttcctggc acgagtggag    480

cgagtgatcg tggtgagcat gaactaccga gtgggagcac tgggattcct ggcactgcca    540

ggaaacccag aggcaccagg aaacatggga ctgttcgacc agcagctggc actgcagtgg    600

gtgcagaaga acatcgcagc attcggagga aacccaaaga gcgtgaccct gttcggagag    660

agcgcaggag cagcaagcgt gagcctgcat ctgctgagcc caggaagcca tagcctgttc    720

acccgagcaa tcctgcagag cggaagcttc aacgcaccat gggcagtgac cagcctgtac    780

gaggcacgaa accgaaccct gaacctggca aagctgaccg gatgtagccg agagaacgag    840

accgagatca tcaagtgtct gcgaaacaag gacccacagg agatcctgct gaacgaggca    900

ttcgtggtgc catacggaac ccccactgagc gtgaacttcg gaccaaccgt ggacggagac    960

ttcctgaccg acatgccaga catcctgctg gagctgggac agttcaagaa gacccagatc   1020

ctggtgggag tgaacaagga cgagggaacc gcattcctgg tgtacggagc accaggattc   1080

agcaaggaca acaacagcat catcacccga aaggagttcc aggagggact gaagatcttc   1140

ttcccaggag tgagcgagtt cggaaaggag agcatcctgt tccattacac cgactgggtg   1200

gacgaccagc gaccagagaa ctaccgagag gcactgggag acgtggtggg agactacaac   1260

ttcatctgtc cagcactgga gttcaccaag aagttcagcg agtggggaaa caacgcattc   1320

ttctactact tcgagcatcg aagcagcaag ctgccatggc cagagtggat gggagtgatg   1380

catggatacg agatcgagtt cgtgttcgga ctgccactgg agcgacgaga caactacacc   1440

aaggcagagg agatcctgag ccgaagcatc gtgaagcgat gggcaaactt cgcaaagtac   1500

ggaaacccaa acgagaccca gaacaacagc accagctggc cagtgttcaa gagcaccgag   1560

cagaagtacc tgaccctgaa caccgagagc acccgaatca tgaccaagct gcgagcacag   1620

cagtgtcgat tctggaccag cttcttccca aaggtgctgg agatgaccgg aaacatcgac   1680

gaggcagagt gggagtggaa ggcaggattc catcgatgga acaactacat gatggactgg   1740
```

aagaaccagt tcaacgacta caccagcaag aaggagagct gtgtgggact gtgataaggc 1800
cggcc 1805

<210> SEQ ID NO 11
<211> LENGTH: 1805
<212> TYPE: DNA
<213> ORGANISM: Artificial Sequence
<220> FEATURE:
<223> OTHER INFORMATION: human BChE C7 with IL2 leader peptide.

<400> SEQUENCE: 11
tctagaccca ccatgagaat gcaattatta ttattaattg cattatcatt agcattagtt 60
acaaattcag aagatgatat tattattgca acaaaaaatg gtaaagttag aggtatgaat 120
ttaacagttt ttggtggtac agttacagca tttttaggta ttccatatgc acaaccacca 180
ttaggtagat taagatttaa aaaaccacaa tcattaacaa aatggtcaga tatttggaat 240
gcaacaaaat atgcaaattc atgttgtcaa aatattgatc aatcatttcc aggttttcat 300
ggttcagaaa tgtggaatcc aaatacagat ttatcagaag attgtttata tttaaatgtt 360
tggattccag caccaaaacc aaaaaatgca acagttttaa tttggattta tggtggtggt 420
tttcaaacag gtacatcatc attacatgtt tatgatggta aatttttagc aagagttgaa 480
agagttattg ttgtttcaat gaattataga gttggtgcat taggtttttt agcattacca 540
ggtaatccag aagcaccagg taatatgggt ttatttgatc aacaattagc attacaatgg 600
gttcaaaaaa atattgcagc atttggtggt aatccaaaat cagttacatt atttggtgaa 660
tcagcaggtg cagcatcagt ttcattacat ttattatcac caggttcaca ttcattattt 720
acaagagcaa ttttacaatc aggttcattt aatgcaccat gggcagttac atcattatat 780
gaagcaagaa atagaacatt aaatttagca aaattaacag gttgttcaag agaaaatgaa 840
acagaaatta ttaaatgttt aagaaataaa gatccacaag aaattttatt aaatgaagca 900
tttgttgttc catatggtac accattatca gttaattttg gtccaacagt tgatggtgat 960
tttttaacag atatgccaga tattttatta gaattaggtc aatttaaaaa aacacaaatt 1020
ttagttggtg ttaataaaga tgaaggtaca gcatttttag tttatggtgc accaggtttt 1080
tcaaaagata ataattcaat tattacaaga aaagaatttc aagaaggttt aaaaattttt 1140
tttccaggtg tttcagaatt tggtaaagaa tcaattttat ttcattatac agattgggtt 1200
gatgatcaaa gaccagaaaa ttatagagaa gcattaggtg atgttgttgg tgattataat 1260
tttatttgtc cagcattaga atttacaaaa aaattttcag aatggggtaa taatgcattt 1320
ttttattatt ttgaacatag atcatcaaaa ttaccatggc cagaatggat gggtgttatg 1380
catggttatg aaattgaatt tgtttttggt ttaccattag aaagaagaga taattataca 1440
aaagcagaag aaattttatc aagatcaatt gttaaaagat gggcaaattt tgcaaaatat 1500
ggtaatccaa atgaaacaca aaataattca acatcatggc cagtttttaa atcaacagaa 1560
caaaaatatt taacattaaa tacagaatca acaagaatta tgacaaaatt aagagcacaa 1620
caatgtagat tttggacatc atttttttcca aaagttttag aaatgacagg taatattgat 1680
gaagcagaat gggaatggaa agcaggtttt catagatgga ataattatat gatggattgg 1740
aaaaatcaat ttaatgatta tacatcaaaa aaagaatcat gtgttggttt atgataaggc 1800
cggcc 1805

<210> SEQ ID NO 12
<211> LENGTH: 1802

<212> TYPE: DNA
<213> ORGANISM: Artificial Sequence
<220> FEATURE:
<223> OTHER INFORMATION: human BChE C8 with IL2 leader peptide.

<400> SEQUENCE: 12
ctagacccac catgagaatg cagctgctgc tgctgatcgc tctgtcactg gctctggtga 60
ccaactcaga ggatgatatc atcatcgcta ccaaaaacgg aaaagtgaga ggaatgaacc 120
tgaccgtgtt cggaggaacc gtgaccgctt tcctgggaat cccctatgct cagccccccc 180
tgggaagact gagattcaaa aaaccccagt cactgaccaa atggtcagat atctggaacg 240
ctaccaaata tgctaactca tgctgccaga acatcgatca gtcattcccc ggattccatg 300
gatcagagat gtggaacccc aacaccgatc tgtcagagga ttgcctgtat ctgaacgtgt 360
ggatccccgc tcccaaaccc aaaaacgcta ccgtgctgat ctggatctat ggaggaggat 420
tccagaccgg aacctcatca ctgcatgtgt atgatggaaa attcctggct agagtggaga 480
gagtgatcgt ggtgtcaatg aactatagag tgggagctct gggattcctg gctctgcccg 540
gaaaccccga ggctcccgga aacatgggac tgttcgatca gcagctggct ctgcagtggg 600
tgcagaaaaa catcgctgct ttcggaggaa accccaaatc agtgaccctg ttcggagagt 660
cagctggagc tgcttcagtg tcactgcatc tgctgtcacc cggatcacat tcactgttca 720
ccagagctat cctgcagtca ggatcattca acgctccctg ggctgtgacc tcactgtatg 780
aggctagaaa cagaaccctg aacctggcta aactgaccgg atgctcaaga gagaacgaga 840
ccgagatcat caaatgcctg agaaacaaag atccccagga gatcctgctg aacgaggctt 900
tcgtggtgcc ctatggaacc cccctgtcag tgaacttcgg acccaccgtg gatggagatt 960
tcctgaccga tatgcccgat atcctgctgg agctgggaca gttcaaaaaa acccagatcc 1020
tggtgggagt gaacaaagat gagggaaccg ctttcctggt gtatggagct cccggattct 1080
caaaagataa caactcaatc atcaccagaa aagagttcca ggagggactg aaaatcttct 1140
tccccggagt gtcagagttc ggaaaagagt caatcctgtt ccattatacc gattgggtgg 1200
atgatcagag acccgagaac tatagagagg ctctgggaga tgtggtggga gattataact 1260
tcatctgccc cgctctggag ttcaccaaaa aattctcaga gtggggaaac aacgctttct 1320
tctattattt cgagcataga tcatcaaaac tgccctggcc cgagtggatg ggagtgatgc 1380
atggatatga gatcgagttc gtgttcggac tgcccctgga gagaagagat aactatacca 1440
aagctgagga gatcctgtca agatcaatcg tgaaaagatg ggctaacttc gctaaatatg 1500
gaaaccccaa cgagacccag aacaactcaa cctcatggcc cgtgttcaaa tcaaccgagc 1560
agaaatatct gaccctgaac accgagtcaa ccagaatcat gaccaaactg agagctcagc 1620
agtgcagatt ctggacctca ttcttcccca aagtgctgga gatgaccgga aacatcgatg 1680
aggctgagtg ggagtggaaa gctggattcc atagatggaa caactatatg atggattgga 1740
aaaaccagtt caacgattat acctcaaaaa aagagtcatg cgtgggactg tgataaggcc 1800
gg 1802

<210> SEQ ID NO 13
<211> LENGTH: 1805
<212> TYPE: DNA
<213> ORGANISM: Artificial Sequence
<220> FEATURE:
<223> OTHER INFORMATION: human BChE mutated at G117H and E197Q with IL2 leader peptide.

<400> SEQUENCE: 13
tctagaccca ccatgcggat gcagctgctg ctgctgatcg ccctgagcct ggccctggtg 60
accaacagcg aggatgatat catcatcgcc accaagaacg gaaaggtgcg gggaatgaac 120
ctgaccgtgt tcggaggaac cgtgaccgcc ttcctgggaa tcccatacgc ccagccacca 180
ctgggacggc tgcggttcaa gaagccacag agcctgacca agtggagcga tatctggaac 240
gccaccaagt acgccaacag ctgctgccag aacatcgatc agagcttccc aggattccac 300
ggaagcgaga tgtggaaccc aaacaccgat ctgagcgagg attgcctgta cctgaacgtg 360
tggatcccag ccccaaagcc aaagaacgcc accgtgctga tctggatcta cggaggacac 420
ttccagaccg gaaccagcag cctgcacgtg tacgatggaa agttcctggc ccgggtggag 480
cgggtgatcg tggtgagcat gaactaccgg gtgggagccc tgggattcct ggccctgcca 540
ggaaacccag aggccccagg aaacatggga ctgttcgatc agcagctggc cctgcagtgg 600
gtgcagaaga acatcgccgc cttcggagga aacccaaaga gcgtgaccct gttcggacag 660
agcgccggag ccgccagcgt gagcctgcac ctgctgagcc caggaagcca cagcctgttc 720
acccgggcca tcctgcagag cggaagcttc aacgccccat gggccgtgac cagcctgtac 780
gaggcccgga accggaccct gaacctggcc aagctgaccg gatgcagccg ggagaacgag 840
accgagatca tcaagtgcct gcggaacaag gatccacagg agatcctgct gaacgaggcc 900
ttcgtggtgc catacggaac cccactgagc gtgaacttcg gaccaaccgt ggatggagat 960
ttcctgaccg atatgccaga tatcctgctg gagctgggac agttcaagaa gacccagatc 1020
ctggtgggag tgaacaagga tgagggaacc gccttcctgg tgtacggagc cccaggattc 1080
agcaaggata acaacagcat catcacccgg aaggagttcc aggagggact gaagatcttc 1140
ttcccaggag tgagcgagtt cggaaaggag agcatcctgt tccactacac cgattgggtg 1200
gatgatcagc ggccagagaa ctaccgggag gccctgggag atgtggtggg agattacaac 1260
ttcatctgcc cagccctgga gttcaccaag aagttcagcg agtggggaaa caacgccttc 1320
ttctactact tcgagcaccg gagcagcaag ctgccatggc cagagtggat gggagtgatg 1380
cacggatacg agatcgagtt cgtgttcgga ctgccactgg agcggcggga taactacacc 1440
aaggccgagg agatcctgag ccggagcatc gtgaagcggt gggccaactt cgccaagtac 1500
ggaaacccaa acgagaccca gaacaacagc accagctggc cagtgttcaa gagcaccgag 1560
cagaagtacc tgaccctgaa caccgagagc acccggatca tgaccaagct gcgggcccag 1620
cagtgccggt tctggaccag cttcttccca aaggtgctgg agatgaccgg aaacatcgat 1680
gaggccgagt gggagtggaa ggccggattc caccggtgga acaactacat gatggattgg 1740
aagaaccagt tcaacgatta caccagcaag aaggagagct gcgtgggact gtgataaggc 1800
cggcc 1805

<210> SEQ ID NO 14
<211> LENGTH: 742
<212> TYPE: DNA
<213> ORGANISM: Artificial Sequence
<220> FEATURE:
<223> OTHER INFORMATION: CMV promoter

<400> SEQUENCE: 14
tcaatattgg ccattagcca tattattcat tggttatata gcataaatca atattggcta 60
ttggccattg catacgttgt atctatatca taatatgtac atttatattg gctcatgtcc 120
aatatgaccg ccatgttggc attgattatt gactagttat taatagtaat caattacggg 180

-continued

```
gtcattagtt catagcccat atatggagtt ccgcgttaca taacttacgg taaatggccc    240

gcctggctga ccgcccaacg acccccgccc attgacgtca ataatgacgt atgttcccat    300

agtaacgcca atagggactt tccattgacg tcaatgggtg gagtatttac ggtaaactgc    360

ccacttggca gtacatcaag tgtatcatat gccaagtccg ccccctattg acgtcaatga    420

cggtaaatgg cccgcctggc attatgccca gtacatgacc ttacgggact ttcctacttg    480

gcagtacatc tacgtattag tcatcgctat taccatggtg atgcggtttt ggcagtacac    540

caatgggcgt ggatagcggt ttgactcacg gggatttcca agtctccacc ccattgacgt    600

caatgggagt ttgttttggc accaaaatca acgggacttt ccaaaatgtc gtaataaccc    660

cgccccgttg acgcaaatgg gcggtaggcg tgtacggtgg gaggtctata taagcagagc    720

tcgtttagtg aaccgtcaga tc                                              742


<210> SEQ ID NO 15
<211> LENGTH: 382
<212> TYPE: DNA
<213> ORGANISM: Artificial Sequence
<220> FEATURE:
<223> OTHER INFORMATION: CMV IE promoter

<400> SEQUENCE: 15

ctagtcgaca ttgattattg actagttatt aatagtaatc aattacgggg tcattagttc     60

atagcccata tatggagttc cgcgttacat aacttacggt aaatggcccg cctggctgac    120

cgcccaacga cccccgccca ttgacgtcaa taatgacgta tgttcccata gtaacgccaa    180

tagggacttt ccattgacgt caatgggtgg agtatttacg gtaaactgcc cacttggcag    240

tacatcaagt gtatcatatg ccaagtacgc cccctattga cgtcaatgac ggtaaatggc    300

ccgcctggca ttatgcccag tacatgacct tatgggactt tcctacttgg cagtacatct    360

acgtattagt catcgctatt ac                                              382


<210> SEQ ID NO 16
<211> LENGTH: 281
<212> TYPE: DNA
<213> ORGANISM: Artificial Sequence
<220> FEATURE:
<223> OTHER INFORMATION: CB promoter

<400> SEQUENCE: 16

tggtcgaggt gagccccacg ttctgcttca ctctccccat ctcccccccc tccccacccc     60

caattttgta tttatttatt ttttaattat tttgtgcagc gatgggggcg gggggggggg    120

gggggcgcgc gccaggcggg gcggggcggg gcgaggggcg gggcggggcg aggcggagag    180

gtgcggcggc agccaatcag agcggcgcgc tccgaaagtt tccttttatg gcgaggcggc    240

ggcggcggcg gccctataaa aagcgaagcg cgcggcgggc g                         281


<210> SEQ ID NO 17
<211> LENGTH: 260
<212> TYPE: DNA
<213> ORGANISM: Artificial Sequence
<220> FEATURE:
<223> OTHER INFORMATION: C4 enhancer

<400> SEQUENCE: 17

gcgttacata acttacggta aatggcccgc ctggctgacc gcccaacgac ccccgcccat     60

tgacgtcaat aatgacgtat gttcccatag taacgccaat agggactttc cattgacgtc    120

aatgggtgga gtatttacgg taaactgccc acttggcagt acatcaagtg tatcatatgc    180
```

caagtacgcc ccctattgac gtcaatgacg gtaaatggcc cgcctggcat tatgcccagt 240
acatgacctt atgggacttt 260

<210> SEQ ID NO 18
<211> LENGTH: 1227
<212> TYPE: DNA
<213> ORGANISM: Artificial Sequence
<220> FEATURE:
<223> OTHER INFORMATION: UbC pormoter

<400> SEQUENCE: 18
ggcctccgcg ccgggttttg gcgcctcccg cgggcgcccc cctcctcacg gcgagcgctg 60
ccacgtcaga cgaagggcgc aggagcgtcc tgatccttcc gcccggacgc tcaggacagc 120
ggcccgctgc tcataagact cggccttaga accccagtat cagcagaagg acattttagg 180
acgggacttg ggtgactcta gggcactggt tttctttcca gagagcggaa caggcgagga 240
aaagtagtcc cttctcggcg attctgcgga gggatctccg tggggcggtg aacgccgatg 300
attatataag gacgcgccgg gtgtggcaca gctagttccg tcgcagccgg gatttgggtc 360
gcggttcttg tttgtggatc gctgtgatcg tcacttggtg agtagcgggc tgctgggctg 420
gccggggctt tcgtggccgc cgggccgctc ggtgggacgg aagcgtgtgg agagaccgcc 480
aagggctgta gtctgggtcc gcgagcaagg ttgccctgaa ctgggggttg gggggagcgc 540
agcaaaatgg cggctgttcc cgagtcttga atggaagacg cttgtgaggc gggctgtgag 600
gtcgttgaaa caaggtgggg ggcatggtgg gcggcaagaa cccaaggtct tgaggccttc 660
gctaatgcgg gaaagctctt attcgggtga gatgggctgg ggcaccatct ggggaccctg 720
acgtgaagtt tgtcactgac tggagaactc ggtttgtcgt ctgttgcggg ggcggcagtt 780
atgcggtgcc gttgggcagt gcacccgtac ctttgggagc gcgcgccctc gtcgtgtcgt 840
gacgtcaccc gttctgttgg cttataatgc agggtggggc cacctgccgg taggtgtgcg 900
gtaggctttt ctccgtcgca ggacgcaggg ttcgggccta gggtaggctc tcctgaatcg 960
acaggcgccg gacctctggt gaggggaggg ataagtgagg cgtcagtttc tttggtcggt 1020
tttatgtacc tatcttctta agtagctgaa gctccggttt tgaactatgc gctcggggtt 1080
ggcgagtgtg ttttgtgaag ttttttaggc accttttgaa atgtaatcat ttgggtcaat 1140
atgtaatttt cagtgttaga ctagtaaatt gtccgctaaa ttctggccgt ttttggcttt 1200
tttgttagac gaagctttat tgcggta 1227

<210> SEQ ID NO 19
<211> LENGTH: 51
<212> TYPE: DNA
<213> ORGANISM: Artificial Sequence
<220> FEATURE:
<223> OTHER INFORMATION: c-myc

<400> SEQUENCE: 19
gcggggactt tgcactggaa cttacaacac ccgagcaagg acgcgactct a 51

<210> SEQ ID NO 20
<211> LENGTH: 57
<212> TYPE: DNA
<213> ORGANISM: Artificial Sequence
<220> FEATURE:
<223> OTHER INFORMATION: IL2 leader sequence

<400> SEQUENCE: 20
atgcggatgc agctgctgct gctgattgct ctgagcctgg ctctggtgac caacagc 57

<210> SEQ ID NO 21
<211> LENGTH: 57
<212> TYPE: DNA
<213> ORGANISM: Artificial Sequence
<220> FEATURE:
<223> OTHER INFORMATION: Mutated IL2 leader sequence

<400> SEQUENCE: 21
atgcggatgc agctgctgct gctgatcgcc ctgagcctgg ccctggtgac caacagc 57

<210> SEQ ID NO 22
<211> LENGTH: 591
<212> TYPE: DNA
<213> ORGANISM: Artificial Sequence
<220> FEATURE:
<223> OTHER INFORMATION: IRES

<400> SEQUENCE: 22
gcccctctcc ctcccccccc cctaacgtta ctggccgaag ccgcttggaa taaggccggt 60
gtgcgtttgt ctatatgtta ttttccacca tattgccgtc ttttggcaat gtgagggccc 120
ggaaacctgg ccctgtcttc ttgacgagca ttcctagggg tctttcccct ctcgccaaag 180
gaatgcaagg tctgttgaat gtcgtgaagg aagcagttcc tctggaagct tcttgaagac 240
aaacaacgtc tgtagcgacc ctttgcaggc agcggaaccc cccacctggc gacaggtgcc 300
tctgcggcca aaagccacgt gtataagata cacctgcaaa ggcggcacaa ccccagtgcc 360
acgttgtgag ttggatagtt gtggaaagag tcaaatggct ctcctcaagc gtattcaaca 420
aggggctgaa ggatgcccag aaggtacccc attgtatggg atctgatctg gggcctcggt 480
acacatgctt tacatgtgtt tagtcgaggt taaaaaaacg tctaggcccc ccgaaccacg 540
gggacgtggt tttcctttga aaaacacgat gataatatgg ccacaaccat g 591

<210> SEQ ID NO 23
<211> LENGTH: 226
<212> TYPE: DNA
<213> ORGANISM: Artificial Sequence
<220> FEATURE:
<223> OTHER INFORMATION: PRIMA1 PRP

<400> SEQUENCE: 23
gcatgcaact cctgtcttgc attgcactaa gtcttgcact tgtcacaaac agtccacaga 60
agagctgcag caaggtgacc gatagctgcc ggcacgtgtg ccagtgccgg ccaccaccac 120
cactgccacc accaccacca cggctgctga gcgccccagc cccaaacagc accagctgcc 180
caaccgagga gagctggtgg agcggatgat gaaagcttgc ggccgc 226

<210> SEQ ID NO 24
<211> LENGTH: 280
<212> TYPE: DNA
<213> ORGANISM: Artificial Sequence
<220> FEATURE:
<223> OTHER INFORMATION: lamelledipodin (LDPN) PRP

<400> SEQUENCE: 24
gcatgcaact cctgtcttgc attgcactaa gtcttgcact tgtcacaaac agtccacagc 60
caaagatcgt gaccccatac accgccagcc agccaagccc accactgcca ccaccaccac 120
caccaccacc accaccacca ccaccaccac caccaccacc accaccactg ccaagccaga 180
gcgccccaag cgccggaagc gccgccccaa tgttcgtgaa gtacagcacc atcacccggc 240
tgcagaacgc cagccagcac agcggaaagc ttgcggccgc 280

<210> SEQ ID NO 25
<211> LENGTH: 595
<212> TYPE: DNA
<213> ORGANISM: Artificial Sequence
<220> FEATURE:
<223> OTHER INFORMATION: WPRE

<400> SEQUENCE: 25
cgataatcaa cctctggatt acaaaatttg tgaaagattg actggtattc ttaactatgt 60
tgctcctttt acgctatgtg gatacgctgc tttaatgcct ttgtatcatg ctattgcttc 120
ccgtatggct ttcattttct cctccttgta taaatcctgg ttgctgtctc tttatgagga 180
gttgtggccc gttgtcaggc aacgtggcgt ggtgtgcact gtgtttgctg acgcaacccc 240
cactggttgg ggcattgcca ccacctgtca gctcctttcc gggactttcg ctttccccct 300
ccctattgcc acggcggaac tcatcgccgc ctgccttgcc cgctgctgga caggggctcg 360
gctgttgggc actgacaatt ccgtggtgtt gtcggggaaa tcatcgtcct ttccttggct 420
gctcgcctgt gttgccacct ggattctgcg cgggacgtcc ttctgctacg tcccttcggc 480
cctcaatcca gcggaccttc cttcccgcgg cctgctgccg gctctgcggc ctcttccgcg 540
tcttcgcctt cgccctcaga cgagtcggat ctccctttgg gccgcctccc cgcat 595

<210> SEQ ID NO 26
<211> LENGTH: 127
<212> TYPE: DNA
<213> ORGANISM: Artificial Sequence
<220> FEATURE:
<223> OTHER INFORMATION: Rabbit beta-globin (rBG) polyA

<400> SEQUENCE: 26
gatctttttc cctctgccaa aaattatggg gacatcatga agccccttga gcatctgact 60
tctggctaat aaaggaaatt tattttcatt gcaatagtgt gttggaattt tttgtgtctc 120
tcactcg 127

<210> SEQ ID NO 27
<211> LENGTH: 232
<212> TYPE: DNA
<213> ORGANISM: Artificial Sequence
<220> FEATURE:
<223> OTHER INFORMATION: SV40 polyA

<400> SEQUENCE: 27
cgagcagaca tgataagata cattgatgag tttggacaaa ccacaactag aatgcagtga 60
aaaaaatgct ttatttgtga aatttgtgat gctattgctt tatttgtaac cattataagc 120
tgcaataaac aagttaacaa caacaattgc attcatttta tgtttcaggt tcagggggag 180
atgtgggagg ttttttaaag caagtaaaac ctctacaaat gtggtaaaat cg 232

<210> SEQ ID NO 28
<211> LENGTH: 130
<212> TYPE: DNA
<213> ORGANISM: Artificial Sequence
<220> FEATURE:
<223> OTHER INFORMATION: AAV2 5'ITR

<400> SEQUENCE: 28
ctgcgcgctc gctcgctcac tgaggccgcc cgggcaaagc ccgggcgtcg ggcgaccttt 60

-continued ggtcgcccgg cctcagtgag cgagcgagcg cgcagagagg gagtggccaa ctccatcact 120
aggggttcct 130

<210> SEQ ID NO 29
<211> LENGTH: 130
<212> TYPE: DNA
<213> ORGANISM: Artificial Sequence
<220> FEATURE:
<223> OTHER INFORMATION: AAV2 3'ITR

<400> SEQUENCE: 29
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgcag 130

<210> SEQ ID NO 30
<211> LENGTH: 4835
<212> TYPE: DNA
<213> ORGANISM: Artificial Sequence
<220> FEATURE:
<223> OTHER INFORMATION: UbC-cmyc-IL2-BChE C1-IRES-IL2-PRIMA1-SV40
<220> FEATURE:
<221> NAME/KEY: repeat_region
<222> LOCATION: (14)..(143)
<223> OTHER INFORMATION: 5'ITR
<220> FEATURE:
<221> NAME/KEY: promoter
<222> LOCATION: (204)..(1430)
<223> OTHER INFORMATION: UbC promoter
<220> FEATURE:
<221> NAME/KEY: Intron
<222> LOCATION: (1524)..(1656)
<223> OTHER INFORMATION: Promega chimeric intron (PI)
<220> FEATURE:
<221> NAME/KEY: misc_feature
<222> LOCATION: (1771)..(3572)
<223> OTHER INFORMATION: BChE coding sequence C1
<220> FEATURE:
<221> NAME/KEY: misc_feature
<222> LOCATION: (1782)..(1838)
<223> OTHER INFORMATION: human IL2 leader sequence
<220> FEATURE:
<221> NAME/KEY: misc_feature
<222> LOCATION: (3572)..(4162)
<223> OTHER INFORMATION: IRES
<220> FEATURE:
<221> NAME/KEY: misc_feature
<222> LOCATION: (4167)..(4407)
<223> OTHER INFORMATION: PRIMA1 PRP
<220> FEATURE:
<221> NAME/KEY: polyA
<222> LOCATION: (4410)..(4641)
<223> OTHER INFORMATION: SV40 late PolyA
<220> FEATURE:
<221> NAME/KEY: repeat_region
<222> LOCATION: (4706)..(4835)
<223> OTHER INFORMATION: 3'ITR

<400> SEQUENCE: 30
ggccttaatt aggctgcgcg ctcgctcgct cactgaggcc gcccgggcaa agcccgggcg 60
tcgggcgacc tttggtcgcc cggcctcagt gagcgagcga gcgcgcagag agggagtggc 120
caactccatc actaggggtt ccttgtagtt aatgattaac ccgccatgct acttatctac 180
gtagccatgc tctaggaaga tctggcctcc gcgccgggtt ttggcgcctc ccgcgggcgc 240
ccccctcctc acggcgagcg ctgccacgtc agacgaaggg cgcaggagcg tcctgatcct 300
tccgcccgga cgctcaggac agcggcccgc tgctcataag actcggcctt agaaccccag 360
tatcagcaga aggacatttt aggacgggac ttgggtgact ctagggcact ggttttcttt 420

-continued

```
ccagagagcg gaacaggcga ggaaaagtag tcccttctcg gcgattctgc ggagggatct    480
ccgtggggcg gtgaacgccg atgattatat aaggacgcgc cgggtgtggc acagctagtt    540
ccgtcgcagc cgggatttgg gtcgcggttc ttgtttgtgg atcgctgtga tcgtcacttg    600
gtgagtagcg ggctgctggg ctggccgggg ctttcgtggc cgccgggccg ctcggtggga    660
cggaagcgtg tggagagacc gccaagggct gtagtctggg tccgcgagca aggttgccct    720
gaactggggg ttggggggag cgcagcaaaa tggcggctgt tcccgagtct tgaatggaag    780
acgcttgtga ggcgggctgt gaggtcgttg aaacaaggtg gggggcatgg tgggcggcaa    840
gaacccaagg tcttgaggcc ttcgctaatg cgggaaagct cttattcggg tgagatgggc    900
tggggcacca tctggggacc ctgacgtgaa gtttgtcact gactggagaa ctcggtttgt    960
cgtctgttgc gggggcggca gttatgcggt gccgttgggc agtgcacccg tacctttggg   1020
agcgcgcgcc ctcgtcgtgt cgtgacgtca cccgttctgt tggcttataa tgcagggtgg   1080
ggccacctgc cggtaggtgt gcggtaggct tttctccgtc gcaggacgca gggttcgggc   1140
ctagggtagg ctctcctgaa tcgacaggcg ccggacctct ggtgagggga gggataagtg   1200
aggcgtcagt ttctttggtc ggttttatgt acctatcttc ttaagtagct gaagctccgg   1260
ttttgaacta tgcgctcggg gttggcgagt gtgttttgtg aagtttttta ggcacctttt   1320
gaaatgtaat catttgggtc aatatgtaat ttcagtgtt agactagtaa attgtccgct   1380
aaattctggc cgtttttggc ttttttgtta gacgaagctt tattgcggta gtttatcaca   1440
gttaaattgc taacgcagtc agtgcttctg acacaacagt ctcgaactta agctgcagaa   1500
gttggtcgtg aggcactggg caggtaagta tcaaggttac aagacaggtt taaggagacc   1560
aatagaaact gggcttgtcg agacagagaa gactcttgcg tttctgatag gcacctattg   1620
gtcttactga catccacttt gcctttctct ccacaggtgt ccactcccag ttcaattaca   1680
gctcttaagg ctagagtact taatacgact cactataggc tagcggggac tttgcactgg   1740
aacttacaac acccgagcaa ggacgcgact ctagacccac catgcggatg cagctgctgc   1800
tgctgattgc tctgagcctg gctctggtga ccaacagcga agacgacatt attattgcta   1860
ccaagaacgg caaggtgcgg ggcatgaacc tgaccgtgtt tggcggcacc gtgaccgctt   1920
ttctgggcat tccctatgct cagccccccc tgggccggct gcggtttaag aagccccaga   1980
gcctgaccaa gtggagcgac atttggaacg ctaccaagta tgctaacagc tgttgtcaga   2040
acattgacca gagctttccc ggctttcatg gcagcgaaat gtggaacccc aacaccgacc   2100
tgagcgaaga ctgtctgtat ctgaacgtgt ggattcccgc tcccaagccc aagaacgcta   2160
ccgtgctgat ttggatttat ggcggcggct ttcagaccgg caccagcagc ctgcatgtgt   2220
atgacggcaa gtttctggct cgggtggaac gggtgattgt ggtgagcatg aactatcggg   2280
tgggcgctct gggctttctg gctctgcccg gcaaccccga agctcccggc aacatgggcc   2340
tgtttgacca gcagctggct ctgcagtggg tgcagaagaa cattgctgct tttggcggca   2400
accccaagag cgtgaccctg tttggcgaaa gcgctggcgc tgctagcgtg agcctgcatc   2460
tgctgagccc cggcagccat agcctgttta cccgggctat tctgcagagc ggcagcttta   2520
acgctccctg ggctgtgacc agcctgtatg aagctcggaa ccggaccctg aacctggcta   2580
agctgaccgg ctgtagccgg gaaaacgaaa ccgaaattat taagtgtctg cggaacaagg   2640
acccccagga aattctgctg aacgaagctt ttgtggtgcc ctatggcacc cccctgagcg   2700
tgaactttgg ccccaccgtg gacggcgact ttctgaccga catgcccgac attctgctgg   2760
```

-continued aactgggcca gtttaagaag acccagattc tggtgggcgt gaacaaggac gaaggcaccg 2820
cttttctggt gtatggcgct cccggcttta gcaaggacaa caacagcatt attacccgga 2880
aggaatttca ggaaggcctg aagatttttt ttcccggcgt gagcgaattt ggcaaggaaa 2940
gcattctgtt tcattatacc gactgggtgg acgaccagcg gcccgaaaac tatcgggaag 3000
ctctgggcga cgtggtgggc gactataact ttatttgtcc cgctctggaa tttaccaaga 3060
agtttagcga atggggcaac aacgcttttt tttattattt tgaacatcgg agcagcaagc 3120
tgccctggcc cgaatggatg ggcgtgatgc atggctatga aattgaattt gtgtttggcc 3180
tgcccctgga acggcgggac aactatacca aggctgaaga aattctgagc cggagcattg 3240
tgaagcggtg ggctaacttt gctaagtatg gcaaccccaa cgaaacccag aacaacagca 3300
ccagctggcc cgtgtttaag agcaccgaac agaagtatct gaccctgaac accgaaagca 3360
cccggattat gaccaagctg cgggctcagc agtgtcggtt ttggaccagc tttttttccca 3420 aggtgctgga aatgaccggc aacattgacg aagctgaatg ggaatggaag gctggctttc 3480
atcggtggaa caactatatg atggactgga agaaccagtt taacgactat accagcaaga 3540
aggaaagctg tgtgggcctg tgataaggcc ggcccctctc cctccccccc ccctaacgtt 3600
actggccgaa gccgcttgga ataaggccgg tgtgcgtttg tctatatgtt attttccacc 3660
atattgccgt cttttggcaa tgtgagggcc cggaaacctg gccctgtctt cttgacgagc 3720
attcctaggg gtctttcccc tctcgccaaa ggaatgcaag gtctgttgaa tgtcgtgaag 3780
gaagcagttc ctctggaagc ttcttgaaga caaacaacgt ctgtagcgac cctttgcagg 3840
cagcggaacc ccccacctgg cgacaggtgc ctctgcggcc aaaagccacg tgtataagat 3900
acacctgcaa aggcggcaca accccagtgc cacgttgtga gttggatagt tgtggaaaga 3960
gtcaaatggc tctcctcaag cgtattcaac aaggggctga aggatgccca gaaggtaccc 4020
cattgtatgg gatctgatct ggggcctcgg tacacatgct ttacatgtgt ttagtcgagg 4080
ttaaaaaaac gtctaggccc cccgaaccac ggggacgtgg ttttcctttg aaaaacacga 4140
tgataatatg gccacaacca tgtaccgcat gcaactcctg tcttgcattg cactaagtct 4200
tgcacttgtc acaaacagtc cacagaagag ctgcagcaag gtgaccgata gctgccggca 4260
cgtgtgccag tgccggccac caccaccact gccaccacca ccaccaccac caccaccacc 4320
acggctgctg agcgccccag ccccaaacag caccagctgc ccaaccgagg agagctggtg 4380
gagcggatga tgaaagcttg cggccgcttc gagcagacat gataagatac attgatgagt 4440
ttggacaaac cacaactaga atgcagtgaa aaaaatgctt tatttgtgaa atttgtgatg 4500
ctattgcttt atttgtaacc attataagct gcaataaaca agttaacaac aacaattgca 4560
ttcattttat gtttcaggtt cagggggaga tgtgggaggt tttttaaagc aagtaaaacc 4620
tctacaaatg tggtaaaatc gataaggatc ttcctagagc atggctacgt agataagtag 4680
catggcgggt taatcattaa ctacaaggaa cccctagtga tggagttggc cactccctct 4740
ctgcgcgctc gctcgctcac tgaggccggg cgaccaaagg tcgcccgacg cccgggcttt 4800
gcccgggcgg cctcagtgag cgagcgagcg cgcag 4835

<210> SEQ ID NO 31
<211> LENGTH: 4874
<212> TYPE: DNA
<213> ORGANISM: Artificial Sequence
<220> FEATURE:
<223> OTHER INFORMATION: UbC-cmyc-IL2-BChE C1-IRES-IL2-LPDN-SV40
<220> FEATURE:
<221> NAME/KEY: repeat_region
<222> LOCATION: (14)..(143)
<223> OTHER INFORMATION: 5'ITR
<220> FEATURE:
<221> NAME/KEY: promoter
<222> LOCATION: (204)..(1430)
<223> OTHER INFORMATION: UbC promoter
<220> FEATURE:
<221> NAME/KEY: Intron
<222> LOCATION: (1524)..(1656)
<223> OTHER INFORMATION: Promega chimeric intron
<220> FEATURE:
<221> NAME/KEY: misc_feature
<222> LOCATION: (1770)..(3574)
<223> OTHER INFORMATION: BChE coding sequence C1
<220> FEATURE:
<221> NAME/KEY: misc_feature
<222> LOCATION: (1782)..(1838)
<223> OTHER INFORMATION: human IL2 leader sequence
<220> FEATURE:
<221> NAME/KEY: misc_feature
<222> LOCATION: (3572)..(4162)
<223> OTHER INFORMATION: IRES
<220> FEATURE:
<221> NAME/KEY: misc_feature
<222> LOCATION: (4167)..(4446)
<223> OTHER INFORMATION: LPDN PRP
<220> FEATURE:
<221> NAME/KEY: polyA_signal
<222> LOCATION: (4449)..(4680)
<223> OTHER INFORMATION: SV40 late polyadenylation signal
<220> FEATURE:
<221> NAME/KEY: repeat_region
<222> LOCATION: (4745)..(4874)
<223> OTHER INFORMATION: 5'ITR

<400> SEQUENCE: 31
ggccttaatt aggctgcgcg ctcgctcgct cactgaggcc gcccgggcaa agcccgggcg 60
tcgggcgacc tttggtcgcc cggcctcagt gagcgagcga gcgcgcagag agggagtggc 120
caactccatc actaggggtt ccttgtagtt aatgattaac ccgccatgct acttatctac 180
gtagccatgc tctaggaaga tctggcctcc gcgccgggtt ttggcgcctc ccgcgggcgc 240
ccccctcctc acggcgagcg ctgccacgtc agacgaaggg cgcaggagcg tcctgatcct 300 tccgccccgga cgctcaggac agcggcccgc tgctcataag actcggcctt agaaccccag 360
tatcagcaga aggacatttt aggacgggac ttgggtgact ctagggcact ggttttcttt 420
ccagagagcg gaacaggcga ggaaaagtag tcccttctcg gcgattctgc ggagggatct 480
ccgtggggcg gtgaacgccg atgattatat aaggacgcgc cgggtgtggc acagctagtt 540
ccgtcgcagc cgggatttgg gtcgcggttc ttgtttgtgg atcgctgtga tcgtcacttg 600
gtgagtagcg ggctgctggg ctggccgggg ctttcgtggc cgccgggccg ctcggtggga 660
cggaagcgtg tggagagacc gccaagggct gtagtctggg tccgcgagca aggttgccct 720
gaactggggg ttggggggag cgcagcaaaa tggcggctgt tcccgagtct tgaatggaag 780
acgcttgtga ggcgggctgt gaggtcgttg aaacaaggtg gggggcatgg tgggcggcaa 840
gaacccaagg tcttgaggcc ttcgctaatg cgggaaagct cttattcggg tgagatgggc 900
tggggcacca tctggggacc ctgacgtgaa gtttgtcact gactggagaa ctcggtttgt 960
cgtctgttgc gggggcggca gttatgcggt gccgttgggc agtgcacccg tacctttggg 1020
agcgcgcgcc ctcgtcgtgt cgtgacgtca cccgttctgt tggcttataa tgcagggtgg 1080
ggccacctgc cggtaggtgt gcggtaggct tttctccgtc gcaggacgca gggttcgggc 1140
ctagggtagg ctctcctgaa tcgacaggcg ccggacctct ggtgaggggga gggataagtg 1200 aggcgtcagt ttctttggtc ggttttatgt acctatcttc ttaagtagct gaagctccgg 1260

-continued

```
ttttgaacta tgcgctcggg gttggcgagt gtgttttgtg aagtttttta ggcacctttt   1320
gaaatgtaat catttgggtc aatatgtaat tttcagtgtt agactagtaa attgtccgct   1380
aaattctggc cgtttttggc tttttttgtta gacgaagctt tattgcggta gtttatcaca   1440
gttaaattgc taacgcagtc agtgcttctg acacaacagt ctcgaactta agctgcagaa   1500
gttggtcgtg aggcactggg caggtaagta tcaaggttac aagacaggtt taaggagacc   1560
aatagaaact gggcttgtcg agacagagaa gactcttgcg tttctgatag gcacctattg   1620
gtcttactga catccacttt gcctttctct ccacaggtgt ccactcccag ttcaattaca   1680
gctcttaagg ctagagtact taatacgact cactataggc tagcggggac tttgcactgg   1740
aacttacaac acccgagcaa ggacgcgact ctagacccac catgcggatg cagctgctgc   1800
tgctgattgc tctgagcctg gctctggtga ccaacagcga agacgacatt attattgcta   1860
ccaagaacgg caaggtgcgg ggcatgaacc tgaccgtgtt tggcggcacc gtgaccgctt   1920
ttctgggcat tccctatgct cagcccccc tgggccggct gcggtttaag aagccccaga   1980
gcctgaccaa gtggagcgac atttggaacg ctaccaagta tgctaacagc tgttgtcaga   2040
acattgacca gagctttccc ggctttcatg gcagcgaaat gtggaacccc aacaccgacc   2100
tgagcgaaga ctgtctgtat ctgaacgtgt ggattcccgc tcccaagccc aagaacgcta   2160
ccgtgctgat ttggatttat ggcggcggct ttcagaccgg caccagcagc ctgcatgtgt   2220
atgacggcaa gtttctggct cgggtggaac gggtgattgt ggtgagcatg aactatcggg   2280
tgggcgctct gggctttctg gctctgcccg gcaaccccga agctcccggc aacatgggcc   2340
tgtttgacca gcagctggct ctgcagtggg tgcagaagaa cattgctgct tttggcggca   2400
accccaagag cgtgaccctg tttggcgaaa gcgctggcgc tgctagcgtg agcctgcatc   2460
tgctgagccc cggcagccat agcctgttta cccgggctat tctgcagagc ggcagcttta   2520
acgctccctg ggctgtgacc agcctgtatg aagctcggaa ccggaccctg aacctggcta   2580
agctgaccgg ctgtagccgg gaaaacgaaa ccgaaattat taagtgtctg cggaacaagg   2640
acccccagga aattctgctg aacgaagctt ttgtggtgcc ctatggcacc cccctgagcg   2700
tgaactttgg ccccaccgtg gacggcgact ttctgaccga catgcccgac attctgctgg   2760
aactgggcca gtttaagaag acccagattc tggtgggcgt gaacaaggac gaaggcaccg   2820
cttttctggt gtatggcgct cccggcttta gcaaggacaa caacagcatt attacccgga   2880
aggaatttca ggaaggcctg aagatttttt ttcccggcgt gagcgaattt ggcaaggaaa   2940
gcattctgtt tcattatacc gactgggtgg acgaccagcg gcccgaaaac tatcgggaag   3000
ctctgggcga cgtggtgggc gactataact ttatttgtcc cgctctggaa tttaccaaga   3060
agtttagcga atggggcaac aacgcttttt tttattattt tgaacatcgg agcagcaagc   3120
tgccctggcc cgaatggatg ggcgtgatgc atggctatga aattgaattt gtgtttggcc   3180
tgcccctgga acggcgggac aactatacca aggctgaaga aattctgagc cggagcattg   3240
tgaagcggtg ggctaacttt gctaagtatg gcaaccccaa cgaaacccag aacaacagca   3300
ccagctggcc cgtgtttaag agcaccgaac agaagtatct gaccctgaac accgaaagca   3360
cccggattat gaccaagctg cgggctcagc agtgtcggtt ttggaccagc ttttttccca   3420
aggtgctgga aatgaccggc aacattgacg aagctgaatg ggaatggaag gctggctttc   3480
atcggtggaa caactatatg atggactgga agaaccagtt taacgactat accagcaaga   3540
aggaaagctg tgtgggcctg tgataaggcc ggcccctctc cctcccccc ccctaacgtt   3600
actggccgaa gccgcttgga ataaggccgg tgtgcgtttg tctatatgtt attttccacc   3660
```

```
atattgccgt cttttggcaa tgtgagggcc cggaaacctg gccctgtctt cttgacgagc   3720

attcctaggg gtctttcccc tctcgccaaa ggaatgcaag gtctgttgaa tgtcgtgaag   3780

gaagcagttc ctctggaagc ttcttgaaga caaacaacgt ctgtagcgac cctttgcagg   3840

cagcggaacc ccccacctgg cgacaggtgc ctctgcggcc aaaagccacg tgtataagat   3900

acacctgcaa aggcggcaca accccagtgc cacgttgtga gttggatagt tgtggaaaga   3960

gtcaaatggc tctcctcaag cgtattcaac aaggggctga aggatgccca gaaggtaccc   4020

cattgtatgg gatctgatct ggggcctcgg tacacatgct ttacatgtgt ttagtcgagg   4080

ttaaaaaaac gtctaggccc cccgaaccac ggggacgtgg ttttcctttg aaaaacacga   4140

tgataatatg gccacaacca tgtaccgcat gcaactcctg tcttgcattg cactaagtct   4200

tgcacttgtc acaaacagtc cacagccaaa gatcgtgacc ccatacaccg ccagccagcc   4260

aagcccacca ctgccaccac caccaccacc accaccacca ccaccaccac caccaccacc   4320

accaccacca ccactgccaa gccagagcgc cccaagcgcc ggaagcgccg ccccaatgtt   4380

cgtgaagtac agcaccatca cccggctgca gaacgccagc cagcacagcg gaaagcttgc   4440

ggccgcttcg agcagacatg ataagataca ttgatgagtt tggacaaacc acaactagaa   4500

tgcagtgaaa aaaatgcttt atttgtgaaa tttgtgatgc tattgcttta tttgtaacca   4560

ttataagctg caataaacaa gttaacaaca acaattgcat tcattttatg tttcaggttc   4620

agggggagat gtgggaggtt ttttaaagca agtaaaacct ctacaaatgt ggtaaaatcg   4680

ataaggatct tcctagagca tggctacgta gataagtagc atggcgggtt aatcattaac   4740

tacaaggaac ccctagtgat ggagttggcc actccctctc tgcgcgctcg ctcgctcact   4800

gaggccgggc gaccaaaggt cgcccgacgc ccgggctttg cccgggcggc ctcagtgagc   4860

gagcgagcgc gcag                                                     4874
```

```
<210> SEQ ID NO 32
<211> LENGTH: 4965
<212> TYPE: DNA
<213> ORGANISM: Artificial Sequence
<220> FEATURE:
<223> OTHER INFORMATION: CB7-cmyc-IL2-BChE C1-IRES-IL2-PRIMA1-rBG
<220> FEATURE:
<221> NAME/KEY: repeat_region
<222> LOCATION: (1)..(130)
<223> OTHER INFORMATION: 5'ITR
<220> FEATURE:
<221> NAME/KEY: promoter
<222> LOCATION: (198)..(579)
<223> OTHER INFORMATION: CMV IE promoter
<220> FEATURE:
<221> NAME/KEY: enhancer
<222> LOCATION: (279)..(538)
<223> OTHER INFORMATION: C4 enhancer with 2 mismatches
<220> FEATURE:
<221> NAME/KEY: promoter
<222> LOCATION: (582)..(862)
<223> OTHER INFORMATION: CB promoter
<220> FEATURE:
<221> NAME/KEY: TATA_signal
<222> LOCATION: (836)..(839)
<220> FEATURE:
<221> NAME/KEY: Intron
<222> LOCATION: (956)..(1928)
<223> OTHER INFORMATION: Chicken beta-actin intron
<220> FEATURE:
<221> NAME/KEY: misc_feature
<222> LOCATION: (1941)..(3742)
<223> OTHER INFORMATION: BChE coding sequence C1
<220> FEATURE:
<221> NAME/KEY: misc_feature
```

<222> LOCATION: (1950)..(2006)
<223> OTHER INFORMATION: human IL2 leader sequence
<220> FEATURE:
<221> NAME/KEY: misc_feature
<222> LOCATION: (3740)..(4330)
<223> OTHER INFORMATION: IRES
<220> FEATURE:
<221> NAME/KEY: misc_feature
<222> LOCATION: (4335)..(4560)
<223> OTHER INFORMATION: PRIMA1 PRP
<220> FEATURE:
<221> NAME/KEY: polyA_signal
<222> LOCATION: (4621)..(4747)
<223> OTHER INFORMATION: Rabbit beta globin polyA
<220> FEATURE:
<221> NAME/KEY: repeat_region
<222> LOCATION: (4836)..(4965)
<223> OTHER INFORMATION: 3'ITR

<400> SEQUENCE: 32
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctaccag ggtaatgggg 180
atcctctaga actatagcta gtcgacattg attattgact agttattaat agtaatcaat 240
tacggggtca ttagttcata gcccatatat ggagttccgc gttacataac ttacggtaaa 300
tggcccgcct ggctgaccgc ccaacgaccc ccgcccattg acgtcaataa tgacgtatgt 360
tcccatagta acgccaatag ggactttcca ttgacgtcaa tgggtggagt atttacggta 420
aactgcccac ttggcagtac atcaagtgta tcatatgcca agtacgcccc ctattgacgt 480
caatgacggt aaatggcccg cctggcatta tgcccagtac atgaccttat gggactttcc 540
tacttggcag tacatctacg tattagtcat cgctattacc atggtcgagg tgagccccac 600
gttctgcttc actctcccca tctcccccc ctccccaccc ccaattttgt atttatttat 660
tttttaatta ttttgtgcag cgatgggggc gggggggggg ggggggcgcg cgccaggcgg 720
ggcggggcgg ggcgaggggc ggggcggggc gaggcggaga ggtgcggcgg cagccaatca 780
gagcggcgcg ctccgaaagt ttccttttat ggcgaggcgg cggcggcggc ggccctataa 840
aaagcgaagc gcgcggcggg cgggagtcgc tgcgcgctgc cttcgccccg tgccccgctc 900
cgccgccgcc tcgcgccgcc cgccccggct ctgactgacc gcgttactcc cacaggtgag 960
cgggcgggac ggcccttctc ctccgggctg taattagcgc ttggtttaat gacggcttgt 1020
ttcttttctg tggctgcgtg aaagccttga ggggctccgg gagggccctt tgtgcggggg 1080
gagcggctcg gggggtgcgt gcgtgtgtgt gtgcgtgggg agcgccgcgt gcggctccgc 1140
gctgcccggc ggctgtgagc gctgcgggcg cggcgcgggg ctttgtgcgc tccgcagtgt 1200
gcgcgagggg agcgcggccg gggcggtgc cccgcggtgc gggggggct gcgaggggaa 1260 caaaggctgc gtgcggggtg tgtgcgtggg ggggtgagca gggggtgtgg gcgcgtcggt 1320
cgggctgcaa cccccccctgc accccccctcc ccgagttgct gagcacggcc cggcttcggg 1380
tgcggggctc cgtacggggc gtggcgcggg gctcgccgtg ccgggcgggg ggtggcggca 1440
ggtgggggtg ccgggcgggg cggggccgcc tcgggccggg gagggctcgg gggaggggcg 1500
cggcggcccc cggagcgccg gcggctgtcg aggcgcggcg agccgcagcc attgcctttt 1560
atggtaatcg tgcgagaggg cgcagggact tcctttgtcc caaatctgtg cggagccgaa 1620
atctgggagg cgccgccgca ccccctctag cgggcgcggg gcgaagcggt gcggcgccgg 1680
caggaaggaa atgggcgggg agggccttcg tgcgtcgccg cgccgccgtc cccttctccc 1740

-continued

```
tctccagcct cggggctgtc cgcgggggga cggctgcctt cggggggggac ggggcagggc   1800
ggggttcggc ttctggcgtg tgaccggcgg ctctagagcc tctgctaacc atgttcatgc   1860
cttcttcttt ttcctacagc tcctgggcaa cgtgctggtt attgtgctgt ctcatcattt   1920
tggcaaagaa ttaattcgct agacccacca tgcggatgca gctgctgctg ctgattgctc   1980
tgagcctggc tctggtgacc aacagcgaag acgacattat tattgctacc aagaacggca   2040
aggtgcgggg catgaacctg accgtgtttg gcggcaccgt gaccgctttt ctgggcattc   2100
cctatgctca gcccccccctg ggccggctgc ggtttaagaa gccccagagc ctgaccaagt   2160
ggagcgacat ttggaacgct accaagtatg ctaacagctg ttgtcagaac attgaccaga   2220
gctttcccgg ctttcatggc agcgaaatgt ggaaccccaa caccgacctg agcgaagact   2280
gtctgtatct gaacgtgtgg attcccgctc ccaagcccaa gaacgctacc gtgctgattt   2340
ggatttatgg cggcggcttt cagaccggca ccagcagcct gcatgtgtat gacggcaagt   2400
ttctggctcg ggtggaacgg gtgattgtgg tgagcatgaa ctatcgggtg ggcgctctgg   2460
gctttctggc tctgcccggc aaccccgaag ctcccggcaa catgggcctg tttgaccagc   2520
agctggctct gcagtgggtg cagaagaaca ttgctgcttt tggcggcaac cccaagagcg   2580
tgaccctgtt tggcgaaagc gctggcgctg ctagcgtgag cctgcatctg ctgagccccg   2640
gcagccatag cctgtttacc cgggctattc tgcagagcgg cagctttaac gctccctggg   2700
ctgtgaccag cctgtatgaa gctcggaacc ggaccctgaa cctggctaag ctgaccggct   2760
gtagccggga aaacgaaacc gaaattatta agtgtctgcg gaacaaggac ccccaggaaa   2820
ttctgctgaa cgaagctttt gtggtgccct atggcacccc cctgagcgtg aactttggcc   2880
ccaccgtgga cggcgacttt ctgaccgaca tgcccgacat tctgctggaa ctgggccagt   2940
ttaagaagac ccagattctg gtgggcgtga acaaggacga aggcaccgct tttctggtgt   3000
atggcgctcc cggctttagc aaggacaaca acagcattat tacccggaag gaatttcagg   3060
aaggcctgaa gatttttttt cccggcgtga gcgaatttgg caaggaaagc attctgtttc   3120
attataccga ctgggtggac gaccagcggc ccgaaaacta tcgggaagct ctgggcgacg   3180
tggtgggcga ctataacttt atttgtcccg ctctggaatt taccaagaag tttagcgaat   3240
ggggcaacaa cgcttttttt tattattttg aacatcggag cagcaagctg ccctggcccg   3300
aatggatggg cgtgatgcat ggctatgaaa ttgaatttgt gtttggcctg cccctggaac   3360
ggcgggacaa ctataccaag gctgaagaaa ttctgagccg gagcattgtg aagcggtggg   3420
ctaactttgc taagtatggc aaccccaacg aaacccagaa caacagcacc agctggcccg   3480
tgtttaagag caccgaacag aagtatctga ccctgaacac cgaaagcacc cggattatga   3540
ccaagctgcg ggctcagcag tgtcggtttt ggaccagctt ttttcccaag gtgctggaaa   3600
tgaccggcaa cattgacgaa gctgaatggg aatggaaggc tggctttcat cggtggaaca   3660
actatatgat ggactggaag aaccagttta acgactatac cagcaagaag gaaagctgtg   3720
tgggcctgtg ataaggccgg cccctctccc tcccccccc ctaacgttac tggccgaagc   3780
cgcttggaat aaggccggtg tgcgtttgtc tatatgttat tttccaccat attgccgtct   3840
tttggcaatg tgagggcccg gaaacctggc cctgtcttct tgacgagcat tcctaggggt   3900
ctttcccctc tcgccaaagg aatgcaaggt ctgttgaatg tcgtgaagga agcagttcct   3960
ctggaagctt cttgaagaca aacaacgtct gtagcgaccc tttgcaggca gcggaacccc   4020
ccacctggcg acaggtgcct ctgcggccaa aagccacgtg tataagatac acctgcaaag   4080
gcggcacaac cccagtgcca cgttgtgagt tggatagttg tggaaagagt caaatggctc   4140
```

```
tcctcaagcg tattcaacaa ggggctgaag gatgcccaga aggtacccca ttgtatggga   4200

tctgatctgg ggcctcggta cacatgcttt acatgtgttt agtcgaggtt aaaaaaacgt   4260

ctaggccccc cgaaccacgg ggacgtggtt ttcctttgaa aaacacgatg ataatatggc   4320

cacaaccatg taccgcatgc aactcctgtc ttgcattgca ctaagtcttg cacttgtcac   4380

aaacagtcca cagaagagct gcagcaaggt gaccgatagc tgccggcacg tgtgccagtg   4440

ccggccacca ccaccactgc caccaccacc accacggctg ctgagcgccc cagccccaaa   4500

cagcaccagc tgcccaaccg aggagagctg gtggagcgga tgatgaaagc ttgcggccgc   4560

ggtacctcta gagtcgaccc gggcggcctc gaggacgggg tgaactacgc ctgaggatcc   4620

gatctttttc cctctgccaa aaattatggg gacatcatga agccccttga gcatctgact   4680

tctggctaat aaaggaaatt tattttcatt gcaatagtgt gttggaattt tttgtgtctc   4740

tcactcggaa gcaattcgtt gatctgaatt tcgaccaccc ataataccca ttaccctggt   4800

agataagtag catggcgggt taatcattaa ctacaaggaa cccctagtga tggagttggc   4860

cactccctct ctgcgcgctc gctcgctcac tgaggccggg cgaccaaagg tcgcccgacg   4920

cccgggcttt gcccgggcgg cctcagtgag cgagcgagcg cgcag                     4965
```

```
<210> SEQ ID NO 33
<211> LENGTH: 5019
<212> TYPE: DNA
<213> ORGANISM: Artificial Sequence
<220> FEATURE:
<223> OTHER INFORMATION: CB7-cmyc-IL2-BChE C1-IRES-IL2-LPDN-rBG
<220> FEATURE:
<221> NAME/KEY: repeat_region
<222> LOCATION: (1)..(130)
<223> OTHER INFORMATION: 5'ITR
<220> FEATURE:
<221> NAME/KEY: enhancer
<222> LOCATION: (279)..(538)
<223> OTHER INFORMATION: C4 enhancer with 2 mismatches
<220> FEATURE:
<221> NAME/KEY: promoter
<222> LOCATION: (582)..(862)
<223> OTHER INFORMATION: CB promoter
<220> FEATURE:
<221> NAME/KEY: TATA_signal
<222> LOCATION: (836)..(839)
<220> FEATURE:
<221> NAME/KEY: Intron
<222> LOCATION: (956)..(1928)
<223> OTHER INFORMATION: Chicken beta-actin intron
<220> FEATURE:
<221> NAME/KEY: misc_feature
<222> LOCATION: (1941)..(3739)
<223> OTHER INFORMATION: BChE conding sequence C1
<220> FEATURE:
<221> NAME/KEY: misc_feature
<222> LOCATION: (3740)..(4330)
<223> OTHER INFORMATION: IRES
<220> FEATURE:
<221> NAME/KEY: misc_feature
<222> LOCATION: (4335)..(4614)
<223> OTHER INFORMATION: LPDN PRP
<220> FEATURE:
<221> NAME/KEY: polyA_signal
<222> LOCATION: (4675)..(4801)
<223> OTHER INFORMATION: Rabbit beta globin polyA
<220> FEATURE:
<221> NAME/KEY: repeat_region
<222> LOCATION: (4890)..(5019)

<400> SEQUENCE: 33

ctgcgcgctc gctcgctcac tgaggccgcc cgggcaaagc ccgggcgtcg ggcgaccttt     60
```

```
ggtcgcccgg cctcagtgag cgagcgagcg cgcagagagg gagtggccaa ctccatcact    120
aggggttcct tgtagttaat gattaacccg ccatgctact tatctaccag ggtaatgggg    180
atcctctaga actatagcta gtcgacattg attattgact agttattaat agtaatcaat    240
tacggggtca ttagttcata gcccatatat ggagttccgc gttacataac ttacggtaaa    300
tggcccgcct ggctgaccgc ccaacgaccc ccgcccattg acgtcaataa tgacgtatgt    360
tcccatagta acgccaatag ggactttcca ttgacgtcaa tgggtggagt atttacggta    420
aactgcccac ttggcagtac atcaagtgta tcatatgcca agtacgcccc ctattgacgt    480
caatgacggt aaatggcccg cctggcatta tgcccagtac atgaccttat gggactttcc    540
tacttggcag tacatctacg tattagtcat cgctattacc atggtcgagg tgagccccac    600
gttctgcttc actctcccca tctccccccc ctccccaccc ccaattttgt atttatttat    660
tttttaatta ttttgtgcag cgatgggggc gggggggggg ggggggcgcg cgccaggcgg    720
ggcggggcgg ggcgaggggc ggggcggggc gaggcggaga ggtgcggcgg cagccaatca    780
gagcggcgcg ctccgaaagt ttccttttat ggcgaggcgg cggcggcggc ggccctataa    840
aaagcgaagc gcgcggcggg cgggagtcgc tgcgcgctgc cttcgccccg tgccccgctc    900
cgccgccgcc tcgcgccgcc cgccccggct ctgactgacc gcgttactcc cacaggtgag    960
cgggcgggac ggcccttctc ctccgggctg taattagcgc ttggtttaat gacggcttgt   1020
ttcttttctg tggctgcgtg aaagccttga ggggctccgg gagggccctt tgtgcggggg   1080
gagcggctcg gggggtgcgt gcgtgtgtgt gtgcgtgggg agcgccgcgt gcggctccgc   1140
gctgcccggc ggctgtgagc gctgcgggcg cggcgcgggg ctttgtgcgc tccgcagtgt   1200
gcgcgagggg agcgcggccg gggcggtgc cccgcggtgc ggggggggct gcgaggggaa    1260
caaaggctgc gtgcggggtg tgtgcgtggg ggggtgagca gggggtgtgg gcgcgtcggt   1320
cgggctgcaa ccccccctgc acccccctcc ccgagttgct gagcacggcc cggcttcggg   1380
tgcggggctc cgtacggggc gtggcgcggg gctcgccgtg ccgggcgggg ggtggcggca   1440
ggtgggggtg ccgggcgggg cggggccgcc tcgggccggg gagggctcgg gggaggggcg   1500
cggcggcccc cggagcgccg gcggctgtcg aggcgcggcg agccgcagcc attgcctttt   1560
atggtaatcg tgcgagaggg cgcagggact tcctttgtcc caaatctgtg cggagccgaa   1620
atctgggagg cgccgccgca ccccctctag cgggcgcggg gcgaagcggt gcggcgccgg   1680
caggaaggaa atgggcgggg agggccttcg tgcgtcgccg cgccgccgtc cccttctccc   1740
tctccagcct cggggctgtc cgcgggggga cggctgcctt cgggggggac ggggcagggc   1800
ggggttcggc ttctggcgtg tgaccggcgg ctctagagcc tctgctaacc atgttcatgc   1860
cttcttcttt ttcctacagc tcctgggcaa cgtgctggtt attgtgctgt ctcatcattt   1920
tggcaaagaa ttaattcgct agacccacca tgcggatgca gctgctgctg ctgattgctc   1980
tgagcctggc tctggtgacc aacagcgaag acgacattat tattgctacc aagaacggca   2040
aggtgcgggg catgaacctg accgtgtttg gcggcaccgt gaccgctttt ctgggcattc   2100
cctatgctca gcccccccctg ggccggctgc ggtttaagaa gccccagagc ctgaccaagt   2160
ggagcgacat ttggaacgct accaagtatg ctaacagctg ttgtcagaac attgaccaga   2220
gctttcccgg ctttcatggc agcgaaatgt ggaaccccaa caccgacctg agcgaagact   2280
gtctgtatct gaacgtgtgg attcccgctc ccaagcccaa gaacgctacc gtgctgattt   2340
ggatttatgg cggcggcttt cagaccggca ccagcagcct gcatgtgtat gacggcaagt   2400
ttctggctcg ggtggaacgg gtgattgtgg tgagcatgaa ctatcgggtg ggcgctctgg   2460
```

```
gctttctggc tctgcccggc aaccccgaag ctcccggcaa catgggcctg tttgaccagc   2520
agctggctct gcagtgggtg cagaagaaca ttgctgcttt tggcggcaac cccaagagcg   2580
tgaccctgtt tggcgaaagc gctggcgctg ctagcgtgag cctgcatctg ctgagccccg   2640
gcagccatag cctgtttacc cgggctattc tgcagagcgg cagctttaac gctccctggg   2700
ctgtgaccag cctgtatgaa gctcggaacc ggaccctgaa cctggctaag ctgaccggct   2760
gtagccggga aaacgaaacc gaaattatta agtgtctgcg gaacaaggac ccccaggaaa   2820
ttctgctgaa cgaagctttt gtggtgccct atggcacccc cctgagcgtg aactttggcc   2880
ccaccgtgga cggcgacttt ctgaccgaca tgcccgacat tctgctggaa ctgggccagt   2940
ttaagaagac ccagattctg gtgggcgtga acaaggacga aggcaccgct tttctggtgt   3000
atggcgctcc cggctttagc aaggacaaca acagcattat tacccggaag gaatttcagg   3060
aaggcctgaa gatttttttt cccggcgtga gcgaatttgg caaggaaagc attctgtttc   3120
attataccga ctgggtggac gaccagcggc ccgaaaacta tcgggaagct ctgggcgacg   3180
tggtgggcga ctataacttt atttgtcccg ctctggaatt taccaagaag tttagcgaat   3240
ggggcaacaa cgcttttttt tattattttg aacatcggag cagcaagctg ccctggcccg   3300
aatggatggg cgtgatgcat ggctatgaaa ttgaatttgt gtttggcctg cccctggaac   3360
ggcgggacaa ctataccaag gctgaagaaa ttctgagccg gagcattgtg aagcggtggg   3420
ctaactttgc taagtatggc aaccccaacg aaacccagaa caacagcacc agctggcccg   3480
tgtttaagag caccgaacag aagtatctga ccctgaacac cgaaagcacc cggattatga   3540
ccaagctgcg ggctcagcag tgtcggtttt ggaccagctt ttttcccaag gtgctggaaa   3600
tgaccggcaa cattgacgaa gctgaatggg aatggaaggc tggctttcat cggtggaaca   3660
actatatgat ggactggaag aaccagttta acgactatac cagcaagaag gaaagctgtg   3720
tgggcctgtg ataaggccgg cccctctccc tccccccccc ctaacgttac tggccgaagc   3780
cgcttggaat aaggccggtg tgcgtttgtc tatatgttat tttccaccat attgccgtct   3840
tttggcaatg tgagggcccg gaaacctggc cctgtcttct tgacgagcat tcctaggggt   3900
ctttcccctc tcgccaaagg aatgcaaggt ctgttgaatg tcgtgaagga agcagttcct   3960
ctggaagctt cttgaagaca aacaacgtct gtagcgaccc tttgcaggca gcggaacccc   4020
ccacctggcg acaggtgcct ctgcggccaa aagccacgtg tataagatac acctgcaaag   4080
gcggcacaac cccagtgcca cgttgtgagt tggatagttg tggaaagagt caaatggctc   4140
tcctcaagcg tattcaacaa ggggctgaag gatgcccaga aggtacccca ttgtatggga   4200
tctgatctgg ggcctcggta cacatgcttt acatgtgttt agtcgaggtt aaaaaaacgt   4260
ctaggccccc cgaaccacgg ggacgtggtt ttcctttgaa aaacacgatg ataatatggc   4320
cacaaccatg taccgcatgc aactcctgtc ttgcattgca ctaagtcttg cacttgtcac   4380
aaacagtcca cagccaaaga tcgtgacccc atacaccgcc agccagccaa gcccaccact   4440
gccaccacca ccaccaccac caccaccacc accaccacca ccaccaccac caccaccacc   4500
actgccaagc cagagcgccc caagcgccgg aagcgccgcc ccaatgttcg tgaagtacag   4560
caccatcacc cggctgcaga acgccagcca gcacagcgga aagcttgcgg ccgcggtacc   4620
tctagagtcg acccgggcgg cctcgaggac ggggtgaact acgcctgagg atccgatctt   4680
tttccctctg ccaaaaatta tggggacatc atgaagcccc ttgagcatct gacttctggc   4740
taataaagga aatttatttt cattgcaata gtgtgttgga atttttgtg tctctcactc   4800
```

```
ggaagcaatt cgttgatctg aatttcgacc acccataata cccattaccc tggtagataa   4860

gtagcatggc gggttaatca ttaactacaa ggaaccccta gtgatggagt tggccactcc   4920

ctctctgcgc gctcgctcgc tcactgaggc cgggcgacca aaggtcgccc gacgcccggg   4980

ctttgcccgg gcggcctcag tgagcgagcg agcgcgcag                          5019
```

<210> SEQ ID NO 34
<211> LENGTH: 4904
<212> TYPE: DNA
<213> ORGANISM: Artificial Sequence
<220> FEATURE:
<223> OTHER INFORMATION: C4/Ubc hIL2 BChE C1 IRES LPDN
<220> FEATURE:
<221> NAME/KEY: repeat_region
<222> LOCATION: (1)..(130)
<223> OTHER INFORMATION: 5'ITR
<220> FEATURE:
<221> NAME/KEY: enhancer
<222> LOCATION: (279)..(538)
<223> OTHER INFORMATION: C4 enhancer with 2 mismatches
<220> FEATURE:
<221> NAME/KEY: promoter
<222> LOCATION: (565)..(1791)
<223> OTHER INFORMATION: UbC promoter
<220> FEATURE:
<221> NAME/KEY: misc_feature
<222> LOCATION: (1826)..(3624)
<223> OTHER INFORMATION: BChE coding sequence C1
<220> FEATURE:
<221> NAME/KEY: misc_feature
<222> LOCATION: (3625)..(4215)
<223> OTHER INFORMATION: IRES
<220> FEATURE:
<221> NAME/KEY: misc_feature
<222> LOCATION: (4220)..(4499)
<223> OTHER INFORMATION: LPDN PRP
<220> FEATURE:
<221> NAME/KEY: polyA_signal
<222> LOCATION: (4560)..(4686)
<223> OTHER INFORMATION: Rabbit beta globin polyA
<220> FEATURE:
<221> NAME/KEY: repeat_region
<222> LOCATION: (4775)..(4904)
<223> OTHER INFORMATION: 3'ITR

<400> SEQUENCE: 34

```
ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct tgtagttaat gattaacccg ccatgctact tatctaccag ggtaatgggg    180

atcctctaga actatagcta gtcgacattg attattgact agttattaat agtaatcaat    240

tacggggtca ttagttcata gcccatatat ggagttccgc gttacataac ttacggtaaa    300

tggcccgcct ggctgaccgc ccaacgaccc ccgcccattg acgtcaataa tgacgtatgt    360

tcccatagta acgccaatag ggactttcca ttgacgtcaa tgggtggagt atttacggta    420

aactgcccac ttggcagtac atcaagtgta tcatatgcca agtacgcccc ctattgacgt    480

caatgacggt aaatggcccg cctggcatta tgcccagtac atgaccttat gggactttcc    540

tacttggcag tacatctacg atctggcctc cgcgccgggt tttggcgcct cccgcgggcg    600

ccccccctcct cacggcgagc gctgccacgt cagacgaagg gcgcaggagc gtcctgatcc    660

ttccgcccgg acgctcagga cagcggcccg ctgctcataa gactcggcct tagaacccca    720

gtatcagcag aaggacattt taggacggga cttgggtgac tctagggcac tggttttctt    780

tccagagagc ggaacaggcg aggaaaagta gtcccttctc ggcgattctg cggagggatc    840

tccgtggggc ggtgaacgcc gatgattata taaggacgcg ccgggtgtgg cacagctagt    900
```

-continued

```
tccgtcgcag ccgggatttg ggtcgcggtt cttgtttgtg gatcgctgtg atcgtcactt    960
ggtgagtagc gggctgctgg gctggccggg gctttcgtgg ccgccgggcc gctcggtggg   1020
acggaagcgt gtggagagac cgccaagggc tgtagtctgg gtccgcgagc aaggttgccc   1080
tgaactgggg gttgggggga gcgcagcaaa atggcggctg ttcccgagtc ttgaatggaa   1140
gacgcttgtg aggcgggctg tgaggtcgtt gaaacaaggt ggggggcatg gtgggcggca   1200
agaacccaag gtcttgaggc cttcgctaat gcgggaaagc tcttattcgg gtgagatggg   1260
ctggggcacc atctggggac cctgacgtga agtttgtcac tgactggaga actcggtttg   1320
tcgtctgttg cgggggcggc agttatgcgg tgccgttggg cagtgcaccc gtacctttgg   1380
gagcgcgcgc cctcgtcgtg tcgtgacgtc acccgttctg ttggcttata atgcagggtg   1440
gggccacctg ccggtaggtg tgcggtaggc ttttctccgt cgcaggacgc agggttcggg   1500
cctagggtag gctctcctga atcgacaggc gccggacctc tggtgagggg agggataagt   1560
gaggcgtcag tttctttggt cggttttatg tacctatctt cttaagtagc tgaagctccg   1620
gttttgaact atgcgctcgg ggttggcgag tgtgttttgt gaagtttttt aggcaccttt   1680
tgaaatgtaa tcatttgggt caatatgtaa ttttcagtgt tagactagta aattgtccgc   1740
taaattctgg ccgtttttgg ctttttttgtt agacgaagct tggtaccgag ctcggatcca   1800
ctagtccagt gtggtggaat tcgctagacc caccatgcgg atgcagctgc tgctgctgat   1860
tgctctgagc ctggctctgg tgaccaacag cgaagacgac attattattg ctaccaagaa   1920
cggcaaggtg cggggcatga acctgaccgt gtttggcggc accgtgaccg cttttctggg   1980
cattccctat gctcagcccc ccctgggccg gctgcggttt aagaagcccc agagcctgac   2040
caagtggagc gacatttgga acgctaccaa gtatgctaac agctgttgtc agaacattga   2100
ccagagcttt cccggctttc atggcagcga aatgtggaac cccaacaccg acctgagcga   2160
agactgtctg tatctgaacg tgtggattcc cgctcccaag cccaagaacg ctaccgtgct   2220
gatttggatt tatggcggcg gctttcagac cggcaccagc agcctgcatg tgtatgacgg   2280
caagtttctg gctcgggtgg aacgggtgat tgtggtgagc atgaactatc gggtgggcgc   2340
tctgggcttt ctggctctgc ccggcaaccc cgaagctccc ggcaacatgg gcctgtttga   2400
ccagcagctg gctctgcagt gggtgcagaa gaacattgct gcttttggcg gcaaccccaa   2460
gagcgtgacc ctgtttggcg aaagcgctgg cgctgctagc gtgagcctgc atctgctgag   2520
ccccggcagc catagcctgt ttacccgggc tattctgcag agcggcagct ttaacgctcc   2580
ctgggctgtg accagcctgt atgaagctcg gaaccggacc ctgaacctgg ctaagctgac   2640
cggctgtagc cgggaaaacg aaaccgaaat tattaagtgt ctgcggaaca aggaccccca   2700
ggaaattctg ctgaacgaag cttttgtggt gccctatggc accccccctga gcgtgaactt   2760
tggccccacc gtggacggcg actttctgac cgacatgccc gacattctgc tggaactggg   2820
ccagtttaag aagacccaga ttctggtggg cgtgaacaag gacgaaggca ccgcttttct   2880
ggtgtatggc gctcccggct ttagcaagga caacaacagc attattaccc ggaaggaatt   2940
tcaggaaggc ctgaagattt tttttcccgg cgtgagcgaa tttggcaagg aaagcattct   3000
gtttcattat accgactggg tggacgacca gcggcccgaa aactatcggg aagctctggg   3060
cgacgtggtg ggcgactata actttatttg tcccgctctg gaatttacca agaagtttag   3120
cgaatggggc aacaacgctt ttttttatta ttttgaacat cggagcagca agctgccctg   3180
gcccgaatgg atgggcgtga tgcatggcta tgaaattgaa tttgtgtttg gcctgcccct   3240
```

```
ggaacggcgg gacaactata ccaaggctga agaaattctg agccggagca ttgtgaagcg   3300

gtgggctaac tttgctaagt atggcaaccc caacgaaacc cagaacaaca gcaccagctg   3360

gcccgtgttt aagagcaccg aacagaagta tctgaccctg aacaccgaaa gcacccggat   3420

tatgaccaag ctgcgggctc agcagtgtcg gttttggacc agctttttc ccaaggtgct    3480

ggaaatgacc ggcaacattg acgaagctga atgggaatgg aaggctggct ttcatcggtg   3540

gaacaactat atgatggact ggaagaacca gtttaacgac tataccagca agaaggaaag   3600

ctgtgtgggc ctgtgataag gccggcccct ctccctcccc ccccctaac gttactggcc    3660

gaagccgctt ggaataaggc cggtgtgcgt ttgtctatat gttattttcc accatattgc   3720

cgtcttttgg caatgtgagg gcccggaaac ctggccctgt cttcttgacg agcattccta   3780

ggggtctttc ccctctcgcc aaaggaatgc aaggtctgtt gaatgtcgtg aaggaagcag   3840

ttcctctgga agcttcttga agacaaacaa cgtctgtagc gaccctttgc aggcagcgga   3900

accccccacc tggcgacagg tgcctctgcg gccaaaagcc acgtgtataa gatacacctg   3960

caaaggcggc acaaccccag tgccacgttg tgagttggat agttgtggaa agagtcaaat   4020

ggctctcctc aagcgtattc aacaaggggc tgaaggatgc ccagaaggta ccccattgta   4080

tgggatctga tctggggcct cggtacacat gctttacatg tgtttagtcg aggttaaaaa   4140

aacgtctagg ccccccgaac cacggggacg tggttttcct ttgaaaaaca cgatgataat   4200

atggccacaa ccatgtaccg catgcaactc ctgtcttgca ttgcactaag tcttgcactt   4260

gtcacaaaca gtccacagcc aaagatcgtg accccataca ccgccagcca gccaagccca   4320

ccactgccac caccaccacc accaccacca ccaccaccac caccaccacc accaccacca   4380

ccaccactgc caagccagag cgccccaagc gccggaagcg ccgccccaat gttcgtgaag   4440

tacagcacca tcacccggct gcagaacgcc agccagcaca gcggaaagct tgcggccgcg   4500

gtacctctag agtcgacccg ggcggcctcg aggacggggt gaactacgcc tgaggatccg   4560

atctttttcc ctctgccaaa aattatgggg acatcatgaa gccccttgag catctgactt   4620

ctggctaata aaggaaattt attttcattg caatagtgtg ttggaatttt ttgtgtctct   4680

cactcggaag caattcgttg atctgaattt cgaccaccca taatacccat taccctggta   4740

gataagtagc atggcgggtt aatcattaac tacaaggaac ccctagtgat ggagttggcc   4800

actccctctc tgcgcgctcg ctcgctcact gaggccgggc gaccaaaggt cgcccgacgc   4860

ccgggctttg cccgggcggc ctcagtgagc gagcgagcgc gcag                    4904
```

<210> SEQ ID NO 35
<211> LENGTH: 4865
<212> TYPE: DNA
<213> ORGANISM: Artificial Sequence
<220> FEATURE:
<223> OTHER INFORMATION: C4/UbC hIL2 BuChE11 IRES PRIMA
<220> FEATURE:
<221> NAME/KEY: repeat_region
<222> LOCATION: (1)..(130)
<223> OTHER INFORMATION: 5'ITR
<220> FEATURE:
<221> NAME/KEY: enhancer
<222> LOCATION: (279)..(538)
<223> OTHER INFORMATION: C4 enhancer with 2 mismatches
<220> FEATURE:
<221> NAME/KEY: promoter
<222> LOCATION: (565)..(1791)
<223> OTHER INFORMATION: UbC promoter
<220> FEATURE:
<221> NAME/KEY: misc_feature
<222> LOCATION: (1826)..(3624)
<223> OTHER INFORMATION: hBChE coding sequence C1

<220> FEATURE:
<221> NAME/KEY: misc_signal
<222> LOCATION: (1835)..(1891)
<223> OTHER INFORMATION: human IL2 leader sequence
<220> FEATURE:
<221> NAME/KEY: misc_feature
<222> LOCATION: (3625)..(4215)
<223> OTHER INFORMATION: IRES
<220> FEATURE:
<221> NAME/KEY: misc_feature
<222> LOCATION: (4220)..(4460)
<223> OTHER INFORMATION: PRIMA1 PRP
<220> FEATURE:
<221> NAME/KEY: polyA_signal
<222> LOCATION: (4521)..(4647)
<223> OTHER INFORMATION: Rabbit beta globin polyA
<220> FEATURE:
<221> NAME/KEY: repeat_region
<222> LOCATION: (4736)..(4865)
<223> OTHER INFORMATION: 3'ITR

<400> SEQUENCE: 35
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctaccag ggtaatgggg 180
atcctctaga actatagcta gtcgacattg attattgact agttattaat agtaatcaat 240
tacggggtca ttagttcata gcccatatat ggagttccgc gttacataac ttacggtaaa 300
tggcccgcct ggctgaccgc ccaacgaccc ccgcccattg acgtcaataa tgacgtatgt 360
tcccatagta acgccaatag ggactttcca ttgacgtcaa tgggtggagt atttacggta 420
aactgcccac ttggcagtac atcaagtgta tcatatgcca agtacgcccc ctattgacgt 480
caatgacggt aaatggcccg cctggcatta tgcccagtac atgaccttat gggactttcc 540
tacttggcag tacatctacg atctggcctc cgcgccgggt tttggcgcct cccgcgggcg 600 ccccccctcct cacggcgagc gctgccacgt cagacgaagg gcgcaggagc gtcctgatcc 660
ttccgcccgg acgctcagga cagcggcccg ctgctcataa gactcggcct tagaacccca 720
gtatcagcag aaggacattt taggacggga cttgggtgac tctagggcac tggttttctt 780
tccagagagc ggaacaggcg aggaaaagta gtcccttctc ggcgattctg cggagggatc 840
tccgtggggc ggtgaacgcc gatgattata taaggacgcg ccgggtgtgg cacagctagt 900
tccgtcgcag ccgggatttg ggtcgcggtt cttgtttgtg gatcgctgtg atcgtcactt 960
ggtgagtagc gggctgctgg gctggccggg gctttcgtgg ccgccgggcc gctcggtggg 1020
acggaagcgt gtggagagac cgccaagggc tgtagtctgg gtccgcgagc aaggttgccc 1080
tgaactgggg gttgggggga gcgcagcaaa atggcggctg ttcccgagtc ttgaatggaa 1140
gacgcttgtg aggcgggctg tgaggtcgtt gaaacaaggt ggggggcatg gtgggcggca 1200
agaacccaag gtcttgaggc cttcgctaat gcgggaaagc tcttattcgg gtgagatggg 1260
ctggggcacc atctggggac cctgacgtga agtttgtcac tgactggaga actcggtttg 1320
tcgtctgttg cgggggcggc agttatgcgg tgccgttggg cagtgcaccc gtacctttgg 1380
gagcgcgcgc cctcgtcgtg tcgtgacgtc acccgttctg ttggcttata atgcagggtg 1440
gggccacctg ccggtaggtg tgcggtaggc ttttctccgt cgcaggacgc agggttcggg 1500
cctagggtag gctctcctga atcgacaggc gccggacctc tggtgagggg agggataagt 1560
gaggcgtcag tttctttggt cggttttatg tacctatctt cttaagtagc tgaagctccg 1620
gttttgaact atgcgctcgg ggttggcgag tgtgttttgt gaagtttttt aggcaccttt 1680

-continued

```
tgaaatgtaa tcatttgggt caatatgtaa ttttcagtgt tagactagta aattgtccgc   1740
taaattctgg ccgtttttgg ctttttttgtt agacgaagct tggtaccgag ctcggatcca   1800
ctagtccagt gtggtggaat tcgctagacc caccatgcgg atgcagctgc tgctgctgat   1860
tgctctgagc ctggctctgg tgaccaacag cgaagacgac attattattg ctaccaagaa   1920
cggcaaggtg cggggcatga acctgaccgt gtttggcggc accgtgaccg cttttctggg   1980
cattccctat gctcagcccc ccctgggccg gctgcggttt aagaagcccc agagcctgac   2040
caagtggagc gacatttgga acgctaccaa gtatgctaac agctgttgtc agaacattga   2100
ccagagcttt cccggctttc atggcagcga aatgtggaac cccaacaccg acctgagcga   2160
agactgtctg tatctgaacg tgtggattcc cgctcccaag cccaagaacg ctaccgtgct   2220
gatttggatt tatggcggcg gctttcagac cggcaccagc agcctgcatg tgtatgacgg   2280
caagtttctg gctcgggtgg aacgggtgat tgtggtgagc atgaactatc gggtgggcgc   2340
tctgggcttt ctggctctgc ccggcaaccc cgaagctccc ggcaacatgg gcctgtttga   2400
ccagcagctg gctctgcagt gggtgcagaa gaacattgct gcttttggcg gcaaccccaa   2460
gagcgtgacc ctgtttggcg aaagcgctgg cgctgctagc gtgagcctgc atctgctgag   2520
ccccggcagc catagcctgt ttacccgggc tattctgcag agcggcagct ttaacgctcc   2580
ctgggctgtg accagcctgt atgaagctcg gaaccggacc ctgaacctgg ctaagctgac   2640
cggctgtagc cgggaaaacg aaaccgaaat tattaagtgt ctgcggaaca aggaccccca   2700
ggaaattctg ctgaacgaag cttttgtggt gccctatggc acccccctga gcgtgaactt   2760
tggccccacc gtggacggcg actttctgac cgacatgccc gacattctgc tggaactggg   2820
ccagtttaag aagacccaga ttctggtggg cgtgaacaag gacgaaggca ccgcttttct   2880
ggtgtatggc gctcccggct ttagcaagga caacaacagc attattaccc ggaaggaatt   2940
tcaggaaggc ctgaagattt tttttcccgg cgtgagcgaa tttggcaagg aaagcattct   3000
gtttcattat accgactggg tggacgacca gcggcccgaa aactatcggg aagctctggg   3060
cgacgtggtg ggcgactata actttatttg tcccgctctg gaatttacca agaagtttag   3120
cgaatggggc aacaacgctt ttttttatta ttttgaacat cggagcagca agctgccctg   3180
gcccgaatgg atgggcgtga tgcatggcta tgaaattgaa tttgtgtttg gcctgcccct   3240
ggaacggcgg gacaactata ccaaggctga agaaattctg agccggagca ttgtgaagcg   3300
gtgggctaac tttgctaagt atggcaaccc caacgaaacc cagaacaaca gcaccagctg   3360
gcccgtgttt aagagcaccg aacagaagta tctgaccctg aacaccgaaa gcacccggat   3420
tatgaccaag ctgcgggctc agcagtgtcg gttttggacc agctttttttc ccaaggtgct   3480
ggaaatgacc ggcaacattg acgaagctga atgggaatgg aaggctggct ttcatcggtg   3540
gaacaactat atgatggact ggaagaacca gtttaacgac tataccagca agaaggaaag   3600
ctgtgtgggc ctgtgataag gccggcccct ctccctcccc cccccctaac gttactggcc   3660
gaagccgctt ggaataaggc cggtgtgcgt ttgtctatat gttattttcc accatattgc   3720
cgtcttttgg caatgtgagg gcccggaaac ctggccctgt cttcttgacg agcattccta   3780
ggggtctttc ccctctcgcc aaaggaatgc aaggtctgtt gaatgtcgtg aaggaagcag   3840
ttcctctgga agcttcttga agacaaacaa cgtctgtagc gaccctttgc aggcagcgga   3900
acccccccacc tggcgacagg tgcctctgcg gccaaaagcc acgtgtataa gatacacctg   3960
caaaggcggc acaaccccag tgccacgttg tgagttggat agttgtggaa agagtcaaat   4020
ggctctcctc aagcgtattc aacaaggggc tgaaggatgc ccagaaggta ccccattgta   4080
```

```
tgggatctga tctggggcct cggtacacat gctttacatg tgtttagtcg aggttaaaaa   4140

aacgtctagg ccccccgaac cacggggacg tggttttcct ttgaaaaaca cgatgataat   4200

atggccacaa ccatgtaccg catgcaactc ctgtcttgca ttgcactaag tcttgcactt   4260

gtcacaaaca gtccacagaa gagctgcagc aaggtgaccg atagctgccg gcacgtgtgc   4320

cagtgccggc caccaccacc actgccacca ccaccaccac caccaccacc accacggctg   4380

ctgagcgccc cagccccaaa cagcaccagc tgcccaaccg aggagagctg gtggagcgga   4440

tgatgaaagc ttgcggccgc ggtacctcta gagtcgaccc gggcggcctc gaggacgggg   4500

tgaactacgc ctgaggatcc gatctttttc cctctgccaa aaattatggg gacatcatga   4560

agccccttga gcatctgact tctggctaat aaaggaaatt tattttcatt gcaatagtgt   4620

gttggaattt tttgtgtctc tcactcggaa gcaattcgtt gatctgaatt tcgaccaccc   4680

ataataccca ttaccctggt agataagtag catggcgggt taatcattaa ctacaaggaa   4740

cccctagtga tggagttggc cactccctct ctgcgcgctc gctcgctcac tgaggccggg   4800

cgaccaaagg tcgcccgacg cccgggcttt gcccgggcgg cctcagtgag cgagcgagcg   4860

cgcag                                                               4865
```

```
<210> SEQ ID NO 36
<211> LENGTH: 4254
<212> TYPE: DNA
<213> ORGANISM: Artificial Sequence
<220> FEATURE:
<223> OTHER INFORMATION: hBChE C4
<220> FEATURE:
<221> NAME/KEY: misc_feature
<222> LOCATION: (1)..(25)
<223> OTHER INFORMATION: ITR
<220> FEATURE:
<221> NAME/KEY: misc_feature
<222> LOCATION: (87)..(828)
<223> OTHER INFORMATION: human CMV IE enhancer and promoter
<220> FEATURE:
<221> NAME/KEY: TATA_signal
<222> LOCATION: (793)..(797)
<220> FEATURE:
<221> NAME/KEY: Intron
<222> LOCATION: (943)..(1075)
<223> OTHER INFORMATION: Promega chimeric intron
<220> FEATURE:
<221> NAME/KEY: misc_feature
<222> LOCATION: (1189)..(2993)
<223> OTHER INFORMATION: hBChE C4
<220> FEATURE:
<221> NAME/KEY: misc_feature
<222> LOCATION: (2991)..(3581)
<223> OTHER INFORMATION: IRES
<220> FEATURE:
<221> NAME/KEY: misc_feature
<222> LOCATION: (3586)..(3826)
<223> OTHER INFORMATION: PRIMA1 PRP
<220> FEATURE:
<221> NAME/KEY: polyA
<222> LOCATION: (3829)..(4060)
<223> OTHER INFORMATION: SV40 late polyA
<220> FEATURE:
<221> NAME/KEY: misc_feature
<222> LOCATION: (4125)..(4254)
<223> OTHER INFORMATION: ITR

<400> SEQUENCE: 36

ggccaactcc atcactaggg gttccttgta gttaatgatt aacccgccat gctacttatc     60

tacgtagcca tgctctagga agatcttcaa tattggccat tagccatatt attcattggt    120

tatatagcat aaatcaatat tggctattgg ccattgcata cgttgtatct atatcataat    180
```

```
atgtacattt atattggctc atgtccaata tgaccgccat gttggcattg attattgact    240
agttattaat agtaatcaat tacggggtca ttagttcata gcccatatat ggagttccgc    300
gttacataac ttacggtaaa tggcccgcct ggctgaccgc ccaacgaccc ccgcccattg    360
acgtcaataa tgacgtatgt tcccatagta acgccaatag ggactttcca ttgacgtcaa    420
tgggtggagt atttacggta aactgcccac ttggcagtac atcaagtgta tcatatgcca    480
agtccgcccc ctattgacgt caatgacggt aaatggcccg cctggcatta tgcccagtac    540
atgaccttac gggactttcc tacttggcag tacatctacg tattagtcat cgctattacc    600
atggtgatgc ggttttggca gtacaccaat gggcgtggat agcggtttga ctcacgggga    660
tttccaagtc tccaccccat tgacgtcaat gggagtttgt tttggcacca aaatcaacgg    720
gactttccaa aatgtcgtaa taaccccgcc ccgttgacgc aaatgggcgg taggcgtgta    780
cggtgggagg tctatataag cagagctcgt ttagtgaacc gtcagatcac tagaagcttt    840
attgcggtag tttatcacag ttaaattgct aacgcagtca gtgcttctga cacaacagtc    900
tcgaacttaa gctgcagaag ttggtcgtga ggcactgggc aggtaagtat caaggttaca    960
agacaggttt aaggagacca atagaaactg ggcttgtcga gacagagaag actcttgcgt   1020
ttctgatagg cacctattgg tcttactgac atccactttg cctttctctc cacaggtgtc   1080
cactcccagt tcaattacag ctcttaaggc tagagtactt aatacgactc actataggct   1140
agcggggact ttgcactgga acttacaaca cccgagcaag gacgcgactc tagacccacc   1200
atgagaatgc aacttcttct tcttattgca ctttcacttg cacttgttac aaattcagaa   1260
gatgatatta ttattgcaac aaaaaatgga aaagttagag gaatgaatct tacagttttc   1320
ggaggaacag ttacagcatt ccttggaatt ccatatgcac aaccaccact tggaagactt   1380
agattcaaaa aaccacaatc acttacaaaa tggtcagata tttggaatgc aacaaaatat   1440
gcaaattcat gttgtcaaaa tattgatcaa tcattcccag gattccatgg atcagaaatg   1500
tggaatccaa atacagatct ttcagaagat tgtctttatc ttaatgtttg gattccagca   1560
ccaaaaccaa aaaatgcaac agttcttatt tggatttatg gaggaggatt ccaaacagga   1620
acatcatcac ttcatgttta tgatggaaaa ttccttgcaa gagttgaaag agttattgtt   1680
gtttcaatga attatagagt tggagcactt ggattccttg cacttccagg aaatccagaa   1740
gcaccaggaa atatgggact tttcgatcaa caacttgcac ttcaatgggt tcaaaaaaat   1800
attgcagcat tcggaggaaa tccaaaatca gttacacttt tcggagaatc agcaggagca   1860
gcatcagttt cacttcatct tctttcacca ggatcacatt cacttttcac aagagcaatt   1920
cttcaatcag gatcattcaa tgcaccatgg gcagttacat cactttatga agcaagaaat   1980
agaacactta atcttgcaaa acttacagga tgttcaagag aaaatgaaac agaaattatt   2040
aaatgtctta gaaataaaga tccacaagaa attcttctta atgaagcatt cgttgttcca   2100
tatggaacac cactttcagt taatttcgga ccaacagttg atggagattt ccttacagat   2160
atgccagata ttcttcttga acttggacaa ttcaaaaaaa cacaaattct tgttggagtt   2220
aataaagatg aaggaacagc attccttgtt tatggagcac caggattctc aaaagataat   2280
aattcaatta ttacaagaaa agaattccaa gaaggactta aaattttctt cccaggagtt   2340
tcagaattcg gaaaagaatc aattcttttc cattatacag attgggttga tgatcaaaga   2400
ccagaaaatt atagagaagc acttggagat gttgttggag attataattt catttgtcca   2460
gcacttgaat tcacaaaaaa attctcagaa tggggaaata atgcattctt ctattatttc   2520
```

-continued

```
gaacatagat catcaaaact tccatggcca gaatggatgg gagttatgca tggatatgaa   2580

attgaattcg ttttcggact tccacttgaa agaagagata attatacaaa agcagaagaa   2640

attctttcaa gatcaattgt taaaagatgg gcaaatttcg caaaatatgg aaatccaaat   2700

gaaacacaaa ataattcaac atcatggcca gttttcaaat caacagaaca aaaatatctt   2760

acacttaata cagaatcaac aagaattatg acaaaactta gagcacaaca atgtagattc   2820

tggacatcat tcttcccaaa agttcttgaa atgacaggaa atattgatga agcagaatgg   2880

gaatggaaag caggattcca tagatggaat aattatatga tggattggaa aaatcaattc   2940

aatgattata catcaaaaaa agaatcatgt gttggacttt gataaggccg gcccctctcc   3000

ctcccccccc cctaacgtta ctggccgaag ccgcttggaa taaggccggt gtgcgtttgt   3060

ctatatgtta ttttccacca tattgccgtc ttttggcaat gtgagggccc ggaaacctgg   3120

ccctgtcttc ttgacgagca ttcctagggg tctttcccct ctcgccaaag gaatgcaagg   3180

tctgttgaat gtcgtgaagg aagcagttcc tctggaagct tcttgaagac aaacaacgtc   3240

tgtagcgacc ctttgcaggc agcggaaccc cccacctggc gacaggtgcc tctgcggcca   3300

aaagccacgt gtataagata cacctgcaaa ggcggcacaa ccccagtgcc acgttgtgag   3360

ttggatagtt gtggaaagag tcaaatggct ctcctcaagc gtattcaaca aggggctgaa   3420

ggatgcccag aaggtacccc attgtatggg atctgatctg gggcctcggt acacatgctt   3480

tacatgtgtt tagtcgaggt taaaaaaacg tctaggcccc ccgaaccacg gggacgtggt   3540

tttcctttga aaaacacgat gataatatgg ccacaaccat gtaccgcatg caactcctgt   3600

cttgcattgc actaagtctt gcacttgtca caaacagtcc acagaagagc tgcagcaagg   3660

tgaccgatag ctgccggcac gtgtgccagt gccggccacc accaccactg ccaccaccac   3720

caccaccacc accaccacca cggctgctga gcgccccagc cccaaacagc accagctgcc   3780

caaccgagga gagctggtgg agcggatgat gaaagcttgc ggccgcttcg agcagacatg   3840

ataagataca ttgatgagtt tggacaaacc acaactagaa tgcagtgaaa aaaatgcttt   3900

atttgtgaaa tttgtgatgc tattgcttta tttgtaacca ttataagctg caataaacaa   3960

gttaacaaca acaattgcat tcattttatg tttcaggttc agggggagat gtgggaggtt   4020

ttttaaagca agtaaaacct ctacaaatgt ggtaaaatcg ataaggatct tcctagagca   4080

tggctacgta gataagtagc atggcgggtt aatcattaac tacaaggaac ccctagtgat   4140

ggagttggcc actccctctc tgcgcgctcg ctcgctcact gaggccgggc gaccaaaggt   4200

cgcccgacgc ccgggctttg cccgggcggc ctcagtgagc gagcgagcgc gcag         4254
```

<210> SEQ ID NO 37
<211> LENGTH: 7254
<212> TYPE: DNA
<213> ORGANISM: Artificial Sequence
<220> FEATURE:
<223> OTHER INFORMATION: CMV.hBChE C5.IRES.PRIMA1.
<220> FEATURE:
<221> NAME/KEY: misc_feature
<222> LOCATION: (87)..(828)
<223> OTHER INFORMATION: human CMV IE enahncer promoter
<220> FEATURE:
<221> NAME/KEY: TATA_signal
<222> LOCATION: (793)..(797)
<220> FEATURE:
<221> NAME/KEY: Intron
<222> LOCATION: (943)..(1075)
<223> OTHER INFORMATION: promoga chimeric intron
<220> FEATURE:
<221> NAME/KEY: misc_feature
<222> LOCATION: (1189)..(2993)

<223> OTHER INFORMATION: hBChE C5
<220> FEATURE:
<221> NAME/KEY: misc_feature
<222> LOCATION: (2991)..(3581)
<223> OTHER INFORMATION: IRES
<220> FEATURE:
<221> NAME/KEY: misc_feature
<222> LOCATION: (3586)..(3826)
<223> OTHER INFORMATION: PRIMA1 PRP
<220> FEATURE:
<221> NAME/KEY: polyA_signal
<222> LOCATION: (3829)..(4060)
<223> OTHER INFORMATION: SV40 late polyA
<220> FEATURE:
<221> NAME/KEY: misc_feature
<222> LOCATION: (4125)..(4254)
<223> OTHER INFORMATION: ITR

<400> SEQUENCE: 37
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatct tcaatattgg ccattagcca tattattcat tggttatata gcataaatca 240
atattggcta ttggccattg catacgttgt atctatatca taatatgtac atttatattg 300
gctcatgtcc aatatgaccg ccatgttggc attgattatt gactagttat taatagtaat 360
caattacggg gtcattagtt catagcccat atatggagtt ccgcgttaca taacttacgg 420
taaatggccc gcctggctga ccgcccaacg acccccgccc attgacgtca ataatgacgt 480
atgttcccat agtaacgcca atagggactt tccattgacg tcaatgggtg gagtatttac 540
ggtaaactgc ccacttggca gtacatcaag tgtatcatat gccaagtccg ccccctattg 600
acgtcaatga cggtaaatgg cccgcctggc attatgccca gtacatgacc ttacgggact 660
ttcctacttg gcagtacatc tacgtattag tcatcgctat taccatggtg atgcggtttt 720
ggcagtacac caatgggcgt ggatagcggt ttgactcacg gggatttcca agtctccacc 780
ccattgacgt caatgggagt ttgttttggc accaaaatca acgggacttt ccaaaatgtc 840
gtaataaccc cgccccgttg acgcaaatgg gcggtaggcg tgtacggtgg gaggtctata 900
taagcagagc tcgtttagtg aaccgtcaga tcactagaag ctttattgcg gtagtttatc 960
acagttaaat tgctaacgca gtcagtgctt ctgacacaac agtctcgaac ttaagctgca 1020
gaagttggtc gtgaggcact gggcaggtaa gtatcaaggt tacaagacag gtttaaggag 1080
accaatagaa actgggcttg tcgagacaga gaagactctt gcgtttctga taggcaccta 1140
ttggtcttac tgacatccac tttgcctttc tctccacagg tgtccactcc cagttcaatt 1200
acagctctta aggctagagt acttaatacg actcactata ggctagcggg gactttgcac 1260
tggaacttac aacacccgag caaggacgcg actctagacc caccatgcgt atgcagctgc 1320
tgctgctgat tgcgctgagc ctggcgctgg tgaccaacag cgaagatgat attattattg 1380
cgaccaaaaa cggcaaagtg cgtggcatga acctgaccgt gtttggcggc accgtgaccg 1440
cgtttctggg cattccgtat gcgcagccgc cgctgggccg tctgcgtttt aaaaaaccgc 1500
agagcctgac caaatggagc gatatttgga acgcgaccaa atatgcgaac agctgctgcc 1560
agaacattga tcagagcttt ccgggctttc atggcagcga aatgtggaac ccgaacaccg 1620
atctgagcga agattgcctg tatctgaacg tgtggattcc ggcgccgaaa ccgaaaaacg 1680
cgaccgtgct gatttggatt tatggcggcg gctttcagac cggcaccagc agcctgcatg 1740
tgtatgatgg caaatttctg gcgcgtgtgg aacgtgtgat tgtggtgagc atgaactatc 1800
gtgtgggcgc gctgggcttt ctggcgctgc cgggcaaccc ggaagcgccg ggcaacatgg 1860
gcctgtttga tcagcagctg gcgctgcagt gggtgcagaa aaacattgcg gcgtttggcg 1920
gcaacccgaa aagcgtgacc ctgtttggcg aaagcgcggg cgcggcgagc gtgagcctgc 1980
atctgctgag cccgggcagc catagcctgt ttacccgtgc gattctgcag agcggcagct 2040
ttaacgcgcc gtgggcggtg accagcctgt atgaagcgcg taaccgtacc ctgaacctgg 2100
cgaaactgac cggctgcagc cgtgaaaacg aaaccgaaat tattaaatgc ctgcgtaaca 2160
aagatccgca ggaaattctg ctgaacgaag cgtttgtggt gccgtatggc accccgctga 2220
gcgtgaactt tggcccgacc gtggatggcg attttctgac cgatatgccg gatattctgc 2280
tggaactggg ccagtttaaa aaaacccaga ttctggtggg cgtgaacaaa gatgaaggca 2340
ccgcgtttct ggtgtatggc gcgccgggct ttagcaaaga taacaacagc attattaccc 2400
gtaaagaatt tcaggaaggc ctgaaaattt tttttccggg cgtgagcgaa tttggcaaag 2460
aaagcattct gtttcattat accgattggg tggatgatca gcgtccggaa aactatcgtg 2520
aagcgctggg cgatgtggtg ggcgattata actttatttg cccggcgctg gaatttacca 2580
aaaaatttag cgaatggggc aacaacgcgt ttttttatta ttttgaacat cgtagcagca 2640
aactgccgtg gccggaatgg atgggcgtga tgcatggcta tgaaattgaa tttgtgtttg 2700
gcctgccgct ggaacgtcgt gataactata ccaaagcgga agaaattctg agccgtagca 2760
ttgtgaaacg ttgggcgaac tttgcgaaat atggcaaccc gaacgaaacc cagaacaaca 2820
gcaccagctg gccggtgttt aaaagcaccg aacagaaata tctgaccctg aacaccgaaa 2880
gcacccgtat tatgaccaaa ctgcgtgcgc agcagtgccg tttttggacc agcttttttc 2940
cgaaagtgct ggaaatgacc ggcaacattg atgaagcgga atgggaatgg aaagcgggct 3000
ggccaactcc atcactaggg gttccttgta gttaatgatt aacccgccat gctacttatc 3060
tacgtagcca tgctctagga agatcttcaa tattggccat tagccatatt attcattggt 3120
tatatagcat aaatcaatat tggctattgg ccattgcata cgttgtatct atatcataat 3180
atgtacattt atattggctc atgtccaata tgaccgccat gttggcattg attattgact 3240
agttattaat agtaatcaat tacggggtca ttagttcata gcccatatat ggagttccgc 3300
gttacataac ttacggtaaa tggcccgcct ggctgaccgc ccaacgaccc ccgcccattg 3360
acgtcaataa tgacgtatgt tcccatagta acgccaatag ggactttcca ttgacgtcaa 3420
tgggtggagt atttacggta aactgcccac ttggcagtac atcaagtgta tcatatgcca 3480
agtccgcccc ctattgacgt caatgacggt aaatggcccg cctggcatta tgcccagtac 3540
atgaccttac gggactttcc tacttggcag tacatctacg tattagtcat cgctattacc 3600
atggtgatgc ggttttggca gtacaccaat gggcgtggat agcggtttga ctcacgggga 3660
tttccaagtc tccaccccat tgacgtcaat gggagtttgt tttggcacca aaatcaacgg 3720
gactttccaa aatgtcgtaa taaccccgcc ccgttgacgc aaatgggcgg taggcgtgta 3780
cggtgggagg tctatataag cagagctcgt ttagtgaacc gtcagatcac tagaagcttt 3840
attgcggtag tttatcacag ttaaattgct aacgcagtca gtgcttctga cacaacagtc 3900
tcgaacttaa gctgcagaag ttggtcgtga ggcactgggc aggtaagtat caaggttaca 3960
agacaggttt aaggagacca atagaaactg ggcttgtcga gacagagaag actcttgcgt 4020
ttctgatagg cacctattgg tcttactgac atccactttg cctttctctc cacaggtgtc 4080
cactcccagt tcaattacag ctcttaaggc tagagtactt aatacgactc actataggct 4140

-continued

```
agcggggact ttgcactgga acttacaaca cccgagcaag gacgcgactc tagacccacc   4200
atgcgtatgc agctgctgct gctgattgcg ctgagcctgg cgctggtgac caacagcgaa   4260
gatgatatta ttattgcgac caaaaacggc aaagtgcgtg gcatgaacct gaccgtgttt   4320
ggcggcaccg tgaccgcgtt tctgggcatt ccgtatgcgc agccgccgct gggccgtctg   4380
cgttttaaaa aaccgcagag cctgaccaaa tggagcgata tttggaacgc gaccaaatat   4440
gcgaacagct gctgccagaa cattgatcag agctttccgg gctttcatgg cagcgaaatg   4500
tggaacccga acaccgatct gagcgaagat tgcctgtatc tgaacgtgtg gattccggcg   4560
ccgaaaccga aaaacgcgac cgtgctgatt tggatttatg gcggcggctt tcagaccggc   4620
accagcagcc tgcatgtgta tgatggcaaa tttctggcgc gtgtggaacg tgtgattgtg   4680
gtgagcatga actatcgtgt gggcgcgctg ggctttctgg cgctgccggg caacccggaa   4740
gcgccgggca acatgggcct gtttgatcag cagctggcgc tgcagtgggt gcagaaaaac   4800
attgcggcgt ttggcggcaa cccgaaaagc gtgaccctgt ttggcgaaag cgcgggcgcg   4860
gcgagcgtga gcctgcatct gctgagcccg ggcagccata gcctgtttac ccgtgcgatt   4920
ctgcagagcg gcagctttaa cgcgccgtgg gcggtgacca gcctgtatga agcgcgtaac   4980
cgtaccctga acctggcgaa actgaccggc tgcagccgtg aaaacgaaac cgaaattatt   5040
aaatgcctgc gtaacaaaga tccgcaggaa attctgctga acgaagcgtt tgtggtgccg   5100
tatggcaccc cgctgagcgt gaactttggc ccgaccgtgg atggcgattt tctgaccgat   5160
atgccggata ttctgctgga actgggccag tttaaaaaaa cccagattct ggtgggcgtg   5220
aacaaagatg aaggcaccgc gtttctggtg tatggcgcgc cgggctttag caaagataac   5280
aacagcatta ttacccgtaa agaatttcag gaaggcctga aatttttttt tccgggcgtg   5340
agcgaatttg gcaaagaaag cattctgttt cattataccg attgggtgga tgatcagcgt   5400
ccggaaaact atcgtgaagc gctgggcgat gtggtgggcg attataactt tatttgcccg   5460
gcgctggaat ttaccaaaaa atttagcgaa tggggcaaca acgcgttttt ttattatttt   5520
gaacatcgta gcagcaaact gccgtggccg gaatggatgg gcgtgatgca tggctatgaa   5580
attgaatttg tgtttggcct gccgctggaa cgtcgtgata actataccaa agcggaagaa   5640
attctgagcc gtagcattgt gaaacgttgg gcgaactttg cgaaatatgg caacccgaac   5700
gaaacccaga acaacagcac cagctggccg gtgtttaaaa gcaccgaaca gaaatatctg   5760
accctgaaca ccgaaagcac ccgtattatg accaaactgc gtgcgcagca gtgccgtttt   5820
tggaccagct tttttccgaa agtgctggaa atgaccggca acattgatga agcggaatgg   5880
gaatggaaag cgggctttca tcgttggaac aactatatga tggattggaa aaaccagttt   5940
aacgattata ccagcaaaaa agaaagctgc gtgggcctgt gataaggccg gcccctctcc   6000
ctcccccccc cctaacgtta ctggccgaag ccgcttggaa taaggccggt gtgcgtttgt   6060
ctatatgtta ttttccacca tattgccgtc ttttggcaat gtgagggccc ggaaacctgg   6120
ccctgtcttc ttgacgagca ttcctagggg tctttcccct ctcgccaaag gaatgcaagg   6180
tctgttgaat gtcgtgaagg aagcagttcc tctggaagct tcttgaagac aaacaacgtc   6240
tgtagcgacc ctttgcaggc agcggaaccc cccacctggc gacaggtgcc tctgcggcca   6300
aaagccacgt gtataagata cacctgcaaa ggcggcacaa ccccagtgcc acgttgtgag   6360
ttggatagtt gtggaaagag tcaaatggct ctcctcaagc gtattcaaca aggggctgaa   6420
ggatgcccag aaggtacccc attgtatggg atctgatctg gggcctcggt acacatgctt   6480
tacatgtgtt tagtcgaggt taaaaaaacg tctaggcccc ccgaaccacg gggacgtggt   6540
```

```
tttcctttga aaaacacgat gataatatgg ccacaaccat gtaccgcatg caactcctgt   6600

cttgcattgc actaagtctt gcacttgtca caaacagtcc acagaagagc tgcagcaagg   6660

tgaccgatag ctgccggcac gtgtgccagt gccggccacc accaccactg ccaccaccac   6720

caccaccacc accaccacca cggctgctga gcgccccagc cccaaacagc accagctgcc   6780

caaccgagga gagctggtgg agcggatgat gaaagcttgc ggccgcttcg agcagacatg   6840

ataagataca ttgatgagtt tggacaaacc acaactagaa tgcagtgaaa aaaatgcttt   6900

atttgtgaaa tttgtgatgc tattgcttta tttgtaacca ttataagctg caataaacaa   6960

gttaacaaca acaattgcat tcattttatg tttcaggttc agggggagat gtgggaggtt   7020

ttttaaagca agtaaaacct ctacaaatgt ggtaaaatcg ataaggatct tcctagagca   7080

tggctacgta gataagtagc atggcgggtt aatcattaac tacaaggaac ccctagtgat   7140

ggagttggcc actccctctc tgcgcgctcg ctcgctcact gaggccgggc gaccaaaggt   7200

cgcccgacgc ccgggctttg cccgggcggc ctcagtgagc gagcgagcgc gcag         7254
```

<210> SEQ ID NO 38
<211> LENGTH: 4254
<212> TYPE: DNA
<213> ORGANISM: Artificial Sequence
<220> FEATURE:
<223> OTHER INFORMATION: CMV.hBChE C7.IRES.PRIMA1
<220> FEATURE:
<221> NAME/KEY: misc_feature
<222> LOCATION: (87)..(828)
<223> OTHER INFORMATION: human CMV IE enhancer/promoter
<220> FEATURE:
<221> NAME/KEY: TATA_signal
<222> LOCATION: (793)..(797)
<220> FEATURE:
<221> NAME/KEY: Intron
<222> LOCATION: (943)..(1075)
<223> OTHER INFORMATION: Promega chimeric intron
<220> FEATURE:
<221> NAME/KEY: misc_feature
<222> LOCATION: (1189)..(2993)
<223> OTHER INFORMATION: hBChE C7
<220> FEATURE:
<221> NAME/KEY: misc_feature
<222> LOCATION: (2991)..(3581)
<223> OTHER INFORMATION: IRES
<220> FEATURE:
<221> NAME/KEY: misc_feature
<222> LOCATION: (3586)..(3826)
<223> OTHER INFORMATION: PRIMA1 PRP
<220> FEATURE:
<221> NAME/KEY: polyA_signal
<222> LOCATION: (3829)..(4060)
<223> OTHER INFORMATION: SV40 late polyA signal
<220> FEATURE:
<221> NAME/KEY: misc_feature
<222> LOCATION: (4125)..(4254)
<223> OTHER INFORMATION: ITR

<400> SEQUENCE: 38

```
ggccaactcc atcactaggg gttccttgta gttaatgatt aacccgccat gctacttatc     60

tacgtagcca tgctctagga agatcttcaa tattggccat tagccatatt attcattggt    120

tatatagcat aaatcaatat tggctattgg ccattgcata cgttgtatct atatcataat    180

atgtacattt atattggctc atgtccaata tgaccgccat gttggcattg attattgact    240

agttattaat agtaatcaat tacggggtca ttagttcata gcccatatat ggagttccgc    300

gttacataac ttacggtaaa tggcccgcct ggctgaccgc ccaacgaccc ccgcccattg    360

acgtcaataa tgacgtatgt tcccatagta acgccaatag ggactttcca ttgacgtcaa    420
```

```
tgggtggagt atttacggta aactgcccac ttggcagtac atcaagtgta tcatatgcca    480
agtccgcccc ctattgacgt caatgacggt aaatggcccg cctggcatta tgcccagtac    540
atgaccttac gggactttcc tacttggcag tacatctacg tattagtcat cgctattacc    600
atggtgatgc ggttttggca gtacaccaat gggcgtggat agcggtttga ctcacgggga    660
tttccaagtc tccaccccat tgacgtcaat gggagtttgt tttggcacca aaatcaacgg    720
gactttccaa aatgtcgtaa taaccccgcc ccgttgacgc aaatgggcgg taggcgtgta    780
cggtgggagg tctatataag cagagctcgt ttagtgaacc gtcagatcac tagaagcttt    840
attgcggtag tttatcacag ttaaattgct aacgcagtca gtgcttctga cacaacagtc    900
tcgaacttaa gctgcagaag ttggtcgtga ggcactgggc aggtaagtat caaggttaca    960
agacaggttt aaggagacca atagaaactg ggcttgtcga gacagagaag actcttgcgt   1020
ttctgatagg cacctattgg tcttactgac atccactttg cctttctctc cacaggtgtc   1080
cactcccagt tcaattacag ctcttaaggc tagagtactt aatacgactc actataggct   1140
agcggggact ttgcactgga acttacaaca cccgagcaag gacgcgactc tagacccacc   1200
atgagaatgc aattattatt attaattgca ttatcattag cattagttac aaattcagaa   1260
gatgatatta ttattgcaac aaaaaatggt aaagttagag gtatgaattt aacagttttt   1320
ggtggtacag ttacagcatt tttaggtatt ccatatgcac aaccaccatt aggtagatta   1380
agatttaaaa aaccacaatc attaacaaaa tggtcagata tttggaatgc aacaaaatat   1440
gcaaattcat gttgtcaaaa tattgatcaa tcatttccag gttttcatgg ttcagaaatg   1500
tggaatccaa atacagattt atcagaagat tgtttatatt taaatgtttg gattccagca   1560
ccaaaaccaa aaaatgcaac agttttaatt tggatttatg gtggtggttt tcaaacaggt   1620
acatcatcat tacatgttta tgatggtaaa tttttagcaa gagttgaaag agttattgtt   1680
gtttcaatga attatagagt tggtgcatta ggtttttttag cattaccagg taatccagaa   1740
gcaccaggta atatgggttt atttgatcaa caattagcat tacaatgggt tcaaaaaaat   1800
attgcagcat ttggtggtaa tccaaaatca gttacattat ttggtgaatc agcaggtgca   1860
gcatcagttt cattacattt attatcacca ggttcacatt cattatttac aagagcaatt   1920
ttacaatcag gttcatttaa tgcaccatgg gcagttacat cattatatga agcaagaaat   1980
agaacattaa atttagcaaa attaacaggt tgttcaagag aaaatgaaac agaaattatt   2040
aaatgtttaa gaaataaaga tccacaagaa attttattaa atgaagcatt tgttgttcca   2100
tatggtacac cattatcagt taattttggt ccaacagttg atggtgattt tttaacagat   2160
atgccagata ttttattaga attaggtcaa tttaaaaaaa cacaaatttt agttggtgtt   2220
aataaagatg aaggtacagc atttttagtt tatggtgcac caggtttttc aaaagataat   2280
aattcaatta ttacaagaaa agaatttcaa gaaggtttaa aaattttttt tccaggtgtt   2340
tcagaatttg gtaaagaatc aattttattt cattatacag attgggttga tgatcaaaga   2400
ccagaaaatt atagagaagc attaggtgat gttgttggtg attataattt tatttgtcca   2460
gcattagaat ttacaaaaaa attttcagaa tggggtaata atgcattttt ttattatttt   2520
gaacatagat catcaaaatt accatggcca gaatggatgg gtgttatgca tggttatgaa   2580
attgaatttg tttttggttt accattagaa agaagagata attatacaaa agcagaagaa   2640
attttatcaa gatcaattgt taaaagatgg gcaaattttg caaaatatgg taatccaaat   2700
gaaacacaaa ataattcaac atcatggcca gtttttaaat caacagaaca aaaatattta   2760
```

```
acattaaata cagaatcaac aagaattatg acaaaattaa gagcacaaca atgtagattt   2820

tggacatcat tttttccaaa agttttagaa atgacaggta atattgatga agcagaatgg   2880

gaatggaaag caggttttca tagatggaat aattatatga tggattggaa aaatcaattt   2940

aatgattata catcaaaaaa agaatcatgt gttggtttat gataaggccg gcccctctcc   3000

ctcccccccc cctaacgtta ctggccgaag ccgcttggaa taaggccggt gtgcgtttgt   3060

ctatatgtta ttttccacca tattgccgtc ttttggcaat gtgagggccc ggaaacctgg   3120

ccctgtcttc ttgacgagca ttcctagggg tctttcccct ctcgccaaag gaatgcaagg   3180

tctgttgaat gtcgtgaagg aagcagttcc tctggaagct tcttgaagac aaacaacgtc   3240

tgtagcgacc ctttgcaggc agcggaaccc cccacctggc gacaggtgcc tctgcggcca   3300

aaagccacgt gtataagata cacctgcaaa ggcggcacaa ccccagtgcc acgttgtgag   3360

ttggatagtt gtggaaagag tcaaatggct ctcctcaagc gtattcaaca aggggctgaa   3420

ggatgcccag aaggtacccc attgtatggg atctgatctg gggcctcggt acacatgctt   3480

tacatgtgtt tagtcgaggt taaaaaaacg tctaggcccc ccgaaccacg gggacgtggt   3540

tttcctttga aaaacacgat gataatatgg ccacaaccat gtaccgcatg caactcctgt   3600

cttgcattgc actaagtctt gcacttgtca caaacagtcc acagaagagc tgcagcaagg   3660

tgaccgatag ctgccggcac gtgtgccagt gccggccacc accaccactg ccaccaccac   3720

caccaccacc accaccacca cggctgctga gcgccccagc cccaaacagc accagctgcc   3780

caaccgagga gagctggtgg agcggatgat gaaagcttgc ggccgcttcg agcagacatg   3840

ataagataca ttgatgagtt tggacaaacc acaactagaa tgcagtgaaa aaaatgcttt   3900

atttgtgaaa tttgtgatgc tattgcttta tttgtaacca ttataagctg caataaacaa   3960

gttaacaaca acaattgcat tcattttatg tttcaggttc agggggagat gtgggaggtt   4020

ttttaaagca agtaaaacct ctacaaatgt ggtaaaatcg ataaggatct tcctagagca   4080

tggctacgta gataagtagc atggcgggtt aatcattaac tacaaggaac ccctagtgat   4140

ggagttggcc actccctctc tgcgcgctcg ctcgctcact gaggccgggc gaccaaaggt   4200

cgcccgacgc ccgggctttg cccgggcggc ctcagtgagc gagcgagcgc gcag         4254
```

<210> SEQ ID NO 39
<211> LENGTH: 7134
<212> TYPE: DNA
<213> ORGANISM: Artificial Sequence
<220> FEATURE:
<223> OTHER INFORMATION: hBChE plasmid
<220> FEATURE:
<221> NAME/KEY: misc_feature
<222> LOCATION: (87)..(828)
<223> OTHER INFORMATION: human CMV IE enhancer/promoter
<220> FEATURE:
<221> NAME/KEY: TATA_signal
<222> LOCATION: (793)..(797)
<220> FEATURE:
<221> NAME/KEY: Intron
<222> LOCATION: (943)..(1075)
<223> OTHER INFORMATION: Promega chimeric intron
<220> FEATURE:
<221> NAME/KEY: misc_feature
<222> LOCATION: (1144)..(1189)
<223> OTHER INFORMATION: c-myc mini-IRES
<220> FEATURE:
<221> NAME/KEY: misc_feature
<222> LOCATION: (1190)..(2991)
<223> OTHER INFORMATION: hBChE C117H E197Q with human IL2 leader sequence
<220> FEATURE:
<221> NAME/KEY: misc_feature
<222> LOCATION: (2992)..(3581)
<223> OTHER INFORMATION: IRES
<220> FEATURE:
<221> NAME/KEY: polyA_signal
<222> LOCATION: (3829)..(4060)
<223> OTHER INFORMATION: SV40 late polyA
<220> FEATURE:
<221> NAME/KEY: misc_feature
<222> LOCATION: (4125)..(4254)
<223> OTHER INFORMATION: ITR

<400> SEQUENCE: 39
ggccaactcc atcactaggg gttccttgta gttaatgatt aacccgccat gctacttatc 60
tacgtagcca tgctctagga agatcttcaa tattggccat tagccatatt attcattggt 120
tatatagcat aaatcaatat tggctattgg ccattgcata cgttgtatct atatcataat 180
atgtacattt atattggctc atgtccaata tgaccgccat gttggcattg attattgact 240
agttattaat agtaatcaat tacggggtca ttagttcata gcccatatat ggagttccgc 300
gttacataac ttacggtaaa tggcccgcct ggctgaccgc ccaacgaccc ccgcccattg 360
acgtcaataa tgacgtatgt tcccatagta acgccaatag ggactttcca ttgacgtcaa 420
tgggtggagt atttacggta aactgcccac ttggcagtac atcaagtgta tcatatgcca 480
agtccgcccc ctattgacgt caatgacggt aaatggcccg cctggcatta tgcccagtac 540
atgaccttac gggactttcc tacttggcag tacatctacg tattagtcat cgctattacc 600
atggtgatgc ggttttggca gtacaccaat gggcgtggat agcggtttga ctcacgggga 660
tttccaagtc tccaccccat tgacgtcaat gggagtttgt tttggcacca aaatcaacgg 720
gactttccaa aatgtcgtaa taaccccgcc ccgttgacgc aaatgggcgg taggcgtgta 780
cggtgggagg tctatataag cagagctcgt ttagtgaacc gtcagatcac tagaagcttt 840
attgcggtag tttatcacag ttaaattgct aacgcagtca gtgcttctga cacaacagtc 900
tcgaacttaa gctgcagaag ttggtcgtga ggcactgggc aggtaagtat caaggttaca 960
agacaggttt aaggagacca atagaaactg ggcttgtcga gacagagaag actcttgcgt 1020
ttctgatagg cacctattgg tcttactgac atccactttg cctttctctc cacaggtgtc 1080
cactcccagt tcaattacag ctcttaaggc tagagtactt aatacgactc actataggct 1140
agcggggact ttgcactgga acttacaaca cccgagcaag gacgcgactc tagacccacc 1200
atgcggatgc agctgctgct gctgatcgcc ctgagcctgg ccctggtgac caacagcgag 1260
gatgatatca tcatcgccac caagaacgga aaggtgcggg gaatgaacct gaccgtgttc 1320
ggaggaaccg tgaccgcctt cctgggaatc ccatacgccc agccaccact gggacggctg 1380
cggttcaaga agccacagag cctgaccaag tggagcgata tctggaacgc caccaagtac 1440
gccaacagct gctgccagaa catcgatcag agcttcccag gattccacgg aagcgagatg 1500
tggaacccaa acaccgatct gagcgaggat tgcctgtacc tgaacgtgtg gatcccagcc 1560
ccaaagccaa agaacgccac cgtgctgatc tggatctacg gaggacactt ccagaccgga 1620
accagcagcc tgcacgtgta cgatggaaag ttcctggccc gggtggagcg ggtgatcgtg 1680
gtgagcatga actaccgggt gggagccctg ggattcctgg ccctgccagg aaacccagag 1740
gccccaggaa acatgggact gttcgatcag cagctggccc tgcagtgggt gcagaagaac 1800
atcgccgcct tcggaggaaa cccaaagagc gtgaccctgt tcggacagag cgccggagcc 1860
gccagcgtga gcctgcacct gctgagccca ggaagccaca gcctgttcac ccgggccatc 1920
ctgcagagcg gaagcttcaa cgccccatgg gccgtgacca gcctgtacga ggcccggaac 1980

```
cggaccctga acctggccaa gctgaccgga tgcagccggg agaacgagac cgagatcatc   2040
aagtgcctgc ggaacaagga tccacaggag atcctgctga acgaggcctt cgtggtgcca   2100
tacggaaccc cactgagcgt gaacttcgga ccaaccgtgg atggagattt cctgaccgat   2160
atgccagata tcctgctgga gctgggacag ttcaagaaga cccagatcct ggtgggagtg   2220
aacaaggatg agggaaccgc cttcctggtg tacggagccc caggattcag caaggataac   2280
aacagcatca tcacccggaa ggagttccag gagggactga agatcttctt cccaggagtg   2340
agcgagttcg gaaaggagag catcctgttc cactacaccg attgggtgga tgatcagcgg   2400
ccagagaact accgggaggc cctgggagat gtggtgggag attacaactt catctgccca   2460
gccctggagt tcaccaagaa gttcagcgag tggggaaaca acgccttctt ctactacttc   2520
gagcaccgga gcagcaagct gccatggcca gagtggatgg gagtgatgca cggatacgag   2580
atcgagttcg tgttcggact gccactggag cggcgggata actacaccaa ggccgaggag   2640
atcctgagcc ggagcatcgt gaagcggtgg gccaacttcg ccaagtacgg aaacccaaac   2700
gagacccaga acaacagcac cagctggcca gtgttcaaga gcaccgagca gaagtacctg   2760
ctgcgcgctc gctcgctcac tgaggccgcc cgggcaaagc ccgggcgtcg ggcgaccttt   2820
ggtcgcccgg cctcagtgag cgagcgagcg cgcagagagg gagtaccctg aacaccgaga   2880
ggccaactcc atcactaggg gttccttgta gttaatgatt aacccgccat gctacttatc   2940
tacgtagcca tgctctagga agatcttcaa tattggccat tagccatatt attcattggt   3000
tatatagcat aaatcaatat tggctattgg ccattgcata cgttgtatct atatcataat   3060
atgtacattt atattggctc atgtccaata tgaccgccat gttggcattg attattgact   3120
agttattaat agtaatcaat tacggggtca ttagttcata gcccatatat ggagttccgc   3180
gttacataac ttacggtaaa tggcccgcct ggctgaccgc ccaacgaccc ccgcccattg   3240
acgtcaataa tgacgtatgt tcccatagta acgccaatag ggactttcca ttgacgtcaa   3300
tgggtggagt atttacggta aactgcccac ttggcagtac atcaagtgta tcatatgcca   3360
agtccgcccc ctattgacgt caatgacggt aaatggcccg cctggcatta tgcccagtac   3420
atgaccttac gggactttcc tacttggcag tacatctacg tattagtcat cgctattacc   3480
atggtgatgc ggttttggca gtacaccaat gggcgtggat agcggtttga ctcacgggga   3540
tttccaagtc tccaccccat tgacgtcaat gggagtttgt tttggcacca aaatcaacgg   3600
gactttccaa aatgtcgtaa taaccccgcc ccgttgacgc aaatgggcgg taggcgtgta   3660
cggtgggagg tctatataag cagagctcgt ttagtgaacc gtcagatcac tagaagcttt   3720
attgcggtag tttatcacag ttaaattgct aacgcagtca gtgcttctga cacaacagtc   3780
tcgaacttaa gctgcagaag ttggtcgtga ggcactgggc aggtaagtat caaggttaca   3840
agacaggttt aaggagacca atagaaactg ggcttgtcga gacagagaag actcttgcgt   3900
ttctgatagg cacctattgg tcttactgac atccactttg cctttctctc cacaggtgtc   3960
cactcccagt tcaattacag ctcttaaggc tagagtactt aatacgactc actataggct   4020
agcggggact ttgcactgga acttacaaca cccgagcaag gacgcgactc tagacccacc   4080
atgcggatgc agctgctgct gctgatcgcc ctgagcctgg ccctggtgac caacagcgag   4140
gatgatatca tcatcgccac caagaacgga aaggtgcggg gaatgaacct gaccgtgttc   4200
ggaggaaccg tgaccgcctt cctgggaatc ccatacgccc agccaccact gggacggctg   4260
cggttcaaga agccacagag cctgaccaag tggagcgata tctggaacgc caccaagtac   4320
gccaacagct gctgccagaa catcgatcag agcttcccag gattccacgg aagcgagatg   4380
```

```
tggaacccaa acaccgatct gagcgaggat tgcctgtacc tgaacgtgtg gatcccagcc   4440
ccaaagccaa agaacgccac cgtgctgatc tggatctacg gaggacactt ccagaccgga   4500
accagcagcc tgcacgtgta cgatggaaag ttcctggccc gggtggagcg ggtgatcgtg   4560
gtgagcatga actaccgggt gggagccctg ggattcctgg ccctgccagg aaacccagag   4620
gccccaggaa acatgggact gttcgatcag cagctggccc tgcagtgggt gcagaagaac   4680
atcgccgcct tcggaggaaa cccaaagagc gtgaccctgt tcggacagag cgccggagcc   4740
gccagcgtga gcctgcacct gctgagccca ggaagccaca gcctgttcac ccgggccatc   4800
ctgcagagcg gaagcttcaa cgccccatgg gccgtgacca gcctgtacga ggcccggaac   4860
cggaccctga acctggccaa gctgaccgga tgcagccggg agaacgagac cgagatcatc   4920
aagtgcctgc ggaacaagga tccacaggag atcctgctga acgaggcctt cgtggtgcca   4980
tacggaaccc cactgagcgt gaacttcgga ccaaccgtgg atggagattt cctgaccgat   5040
atgccagata tcctgctgga gctgggacag ttcaagaaga cccagatcct ggtgggagtg   5100
aacaaggatg agggaaccgc cttcctggtg tacggagccc caggattcag caaggataac   5160
aacagcatca tcacccggaa ggagttccag gagggactga agatcttctt cccaggagtg   5220
agcgagttcg gaaaggagag catcctgttc cactacaccg attgggtgga tgatcagcgg   5280
ccagagaact accgggaggc cctgggagat gtggtgggag attacaactt catctgccca   5340
gccctggagt tcaccaagaa gttcagcgag tggggaaaca acgccttctt ctactacttc   5400
gagcaccgga gcagcaagct gccatggcca gagtggatgg gagtgatgca cggatacgag   5460
atcgagttcg tgttcggact gccactggag cggcgggata actacaccaa ggccgaggag   5520
atcctgagcc ggagcatcgt gaagcggtgg gccaacttcg ccaagtacgg aaacccaaac   5580
gagacccaga acaacagcac cagctggcca gtgttcaaga gcaccgagca gaagtacctg   5640
accctgaaca ccgagagcac ccggatcatg accaagctgc gggcccagca gtgccggttc   5700
tggaccagct tcttcccaaa ggtgctggag atgaccggaa acatcgatga ggccgagtgg   5760
gagtggaagg ccggattcca ccggtggaac aactacatga tggattggaa gaaccagttc   5820
aacgattaca ccagcaagaa ggagagctgc gtgggactgt gataaggccg gcccctctcc   5880
ctcccccccc cctaacgtta ctggccgaag ccgcttggaa taaggccggt gtgcgtttgt   5940
ctatatgtta ttttccacca tattgccgtc ttttggcaat gtgagggccc ggaaacctgg   6000
ccctgtcttc ttgacgagca ttcctagggg tctttcccct ctcgccaaag gaatgcaagg   6060
tctgttgaat gtcgtgaagg aagcagttcc tctggaagct tcttgaagac aaacaacgtc   6120
tgtagcgacc ctttgcaggc agcggaaccc cccacctggc gacaggtgcc tctgcggcca   6180
aaagccacgt gtataagata cacctgcaaa ggcggcacaa ccccagtgcc acgttgtgag   6240
ttggatagtt gtggaaagag tcaaatggct ctcctcaagc gtattcaaca aggggctgaa   6300
ggatgcccag aaggtacccc attgtatggg atctgatctg gggcctcggt acacatgctt   6360
tacatgtgtt tagtcgaggt taaaaaaacg tctaggcccc ccgaaccacg gggacgtggt   6420
tttcctttga aaaacacgat gataatatgg ccacaaccat gtaccgcatg caactcctgt   6480
cttgcattgc actaagtctt gcacttgtca caaacagtcc acagaagagc tgcagcaagg   6540
tgaccgatag ctgccggcac gtgtgccagt gccggccacc accaccactg ccaccaccac   6600
caccaccacc accaccacca cggctgctga gcgccccagc cccaaacagc accagctgcc   6660
caaccgagga gagctggtgg agcggatgat gaaagcttgc ggccgcttcg agcagacatg   6720
```

ataagataca ttgatgagtt tggacaaacc acaactagaa tgcagtgaaa aaaatgcttt 6780
atttgtgaaa tttgtgatgc tattgcttta tttgtaacca ttataagctg caataaacaa 6840
gttaacaaca acaattgcat tcattttatg tttcaggttc agggggagat gtgggaggtt 6900
ttttaaagca agtaaaacct ctacaaatgt ggtaaaatcg ataaggatct tcctagagca 6960
tggctacgta gataagtagc atggcgggtt aatcattaac tacaaggaac ccctagtgat 7020
ggagttggcc actccctctc tgcgcgctcg ctcgctcact gaggccgggc gaccaaaggt 7080
cgcccgacgc ccgggctttg cccgggcggc ctcagtgagc gagcgagcgc gcag 7134

<210> SEQ ID NO 40
<211> LENGTH: 4358
<212> TYPE: DNA
<213> ORGANISM: Artificial Sequence
<220> FEATURE:
<223> OTHER INFORMATION: CMV.hBChE C2.IRES.PRIMA1
<220> FEATURE:
<221> NAME/KEY: misc_feature
<222> LOCATION: (1)..(130)
<223> OTHER INFORMATION: 5'ITR
<220> FEATURE:
<221> NAME/KEY: misc_feature
<222> LOCATION: (191)..(932)
<223> OTHER INFORMATION: human CMV IE enhancer/promoer
<220> FEATURE:
<221> NAME/KEY: TATA_signal
<222> LOCATION: (897)..(901)
<220> FEATURE:
<221> NAME/KEY: Intron
<222> LOCATION: (1047)..(1179)
<223> OTHER INFORMATION: Promega chimeric intron (PI)
<220> FEATURE:
<221> NAME/KEY: misc_feature
<222> LOCATION: (1293)..(3097)
<223> OTHER INFORMATION: BuChE C2
<220> FEATURE:
<221> NAME/KEY: misc_feature
<222> LOCATION: (3095)..(3685)
<223> OTHER INFORMATION: IRES
<220> FEATURE:
<221> NAME/KEY: misc_feature
<222> LOCATION: (3690)..(3930)
<223> OTHER INFORMATION: PRIMA1 PRP
<220> FEATURE:
<221> NAME/KEY: polyA_signal
<222> LOCATION: (3933)..(4164)
<223> OTHER INFORMATION: SV40 polyA
<220> FEATURE:
<221> NAME/KEY: misc_feature
<222> LOCATION: (4229)..(4358)
<223> OTHER INFORMATION: 3'ITR

<400> SEQUENCE: 40
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatct tcaatattgg ccattagcca tattattcat tggttatata gcataaatca 240
atattggcta ttggccattg catacgttgt atctatatca taatatgtac atttatattg 300
gctcatgtcc aatatgaccg ccatgttggc attgattatt gactagttat taatagtaat 360
caattacggg gtcattagtt catagcccat atatggagtt ccgcgttaca taacttacgg 420
taaatggccc gcctggctga ccgcccaacg acccccgccc attgacgtca ataatgacgt 480
atgttcccat agtaacgcca atagggactt tccattgacg tcaatgggtg gagtatttac 540
ggtaaactgc ccacttggca gtacatcaag tgtatcatat gccaagtccg ccccctattg 600

-continued

```
acgtcaatga cggtaaatgg cccgcctggc attatgccca gtacatgacc ttacgggact    660
ttcctacttg gcagtacatc tacgtattag tcatcgctat taccatggtg atgcggtttt    720
ggcagtacac caatgggcgt ggatagcggt ttgactcacg gggatttcca agtctccacc    780
ccattgacgt caatgggagt ttgttttggc accaaaatca acgggacttt ccaaaatgtc    840
gtaataaccc cgccccgttg acgcaaatgg gcggtaggcg tgtacggtgg gaggtctata    900
taagcagagc tcgtttagtg aaccgtcaga tcactagaag ctttattgcg gtagtttatc    960
acagttaaat tgctaacgca gtcagtgctt ctgacacaac agtctcgaac ttaagctgca   1020
gaagttggtc gtgaggcact gggcaggtaa gtatcaaggt tacaagacag gtttaaggag   1080
accaatagaa actgggcttg tcgagacaga gaagactctt gcgtttctga taggcaccta   1140
ttggtcttac tgacatccac tttgcctttc tctccacagg tgtccactcc cagttcaatt   1200
acagctctta aggctagagt acttaatacg actcactata ggctagcggg gactttgcac   1260
tggaacttac aacacccgag caaggacgcg actctagacc caccatgaga atgcaattgt   1320
tgttgttgat tgcattgtca ttggcattgg tgacaaattc agaagatgat attattattg   1380
caacaaaaaa tggtaaagtg agaggtatga atttgacagt gtttggtggt acagtgacag   1440
catttttggg tattccatat gcacaaccac cattgggtag attgagattt aaaaaaccac   1500
aatcattgac aaaatggtca gatatttgga atgcaacaaa atatgcaaat tcatgttgtc   1560
aaaatattga tcaatcattt ccaggttttc atggttcaga aatgtggaat ccaaatacag   1620
atttgtcaga agattgtttg tatttgaatg tgtggattcc agcaccaaaa ccaaaaaatg   1680
caacagtgtt gatttggatt tatggtggtg gttttcaaac aggtacatca tcattgcatg   1740
tgtatgatgg taaatttttg gcaagagtgg aaagagtgat tgtggtgtca atgaattata   1800
gagtgggtgc attgggtttt ttggcattgc caggtaatcc agaagcacca ggtaatatgg   1860
gtttgtttga tcaacaattg gcattgcaat gggtgcaaaa aaatattgca gcatttggtg   1920
gtaatccaaa atcagtgaca ttgtttggtg aatcagcagg tgcagcatca gtgtcattgc   1980
atttgttgtc accaggttca cattcattgt ttacaagagc aattttgcaa tcaggttcat   2040
ttaatgcacc atgggcagtg acatcattgt atgaagcaag aaatagaaca ttgaatttgg   2100
caaaattgac aggttgttca agagaaaatg aaacagaaat tattaaatgt ttgagaaata   2160
aagatccaca agaaattttg ttgaatgaag catttgtggt gccatatggt acaccattgt   2220
cagtgaattt tggtccaaca gtggatggtg attttttgac agatatgcca gatattttgt   2280
tggaattggg tcaatttaaa aaaacacaaa ttttggtggg tgtgaataaa gatgaaggta   2340
cagcattttt ggtgtatggt gcaccaggtt tttcaaaaga taataattca attattacaa   2400
gaaaagaatt tcaagaaggt ttgaaaattt tttttccagg tgtgtcagaa tttggtaaag   2460
aatcaatttt gtttcattat acagattggg tggatgatca aagaccagaa aattatagag   2520
aagcattggg tgatgtggtg ggtgattata attttatttg tccagcattg gaatttacaa   2580
aaaaattttc agaatggggt aataatgcat ttttttatta ttttgaacat agatcatcaa   2640
aattgccatg gccagaatgg atgggtgtga tgcatggtta tgaaattgaa tttgtgtttg   2700
gtttgccatt ggaaagaaga gataattata caaaagcaga agaaattttg tcaagatcaa   2760
ttgtgaaaag atgggcaaat tttgcaaaat atggtaatcc aaatgaaaca caaaataatt   2820
caacatcatg gccagtgttt aaatcaacag aacaaaaata tttgacattg aatacagaat   2880
caacaagaat tatgacaaaa ttgagagcac aacaatgtag attttggaca tcattttttc   2940
caaaagtgtt ggaaatgaca ggtaatattg atgaagcaga atgggaatgg aaagcaggtt   3000
```

ttcatagatg gaataattat atgatggatt ggaaaaatca atttaatgat tatacatcaa 3060
aaaaagaatc atgtgtgggt ttgtgataag gccggcccct ctccctcccc ccccccctaac 3120 gttactggcc gaagccgctt ggaataaggc cggtgtgcgt ttgtctatat gttattttcc 3180
accatattgc cgtcttttgg caatgtgagg gcccggaaac ctggccctgt cttcttgacg 3240
agcattccta ggggtctttc ccctctcgcc aaaggaatgc aaggtctgtt gaatgtcgtg 3300
aaggaagcag ttcctctgga agcttcttga agacaaacaa cgtctgtagc gaccctttgc 3360
aggcagcgga acccccccacc tggcgacagg tgcctctgcg gccaaaagcc acgtgtataa 3420
gatacacctg caaaggcggc acaaccccag tgccacgttg tgagttggat agttgtggaa 3480
agagtcaaat ggctctcctc aagcgtattc aacaaggggc tgaaggatgc ccagaaggta 3540
ccccattgta tgggatctga tctggggcct cggtacacat gctttacatg tgtttagtcg 3600
aggttaaaaa aacgtctagg ccccccgaac cacggggacg tggttttcct ttgaaaaaca 3660
cgatgataat atggccacaa ccatgtaccg catgcaactc ctgtcttgca ttgcactaag 3720
tcttgcactt gtcacaaaca gtccacagaa gagctgcagc aaggtgaccg atagctgccg 3780
gcacgtgtgc cagtgccggc caccaccacc actgccacca ccaccaccac caccaccacc 3840
accacggctg ctgagcgccc cagccccaaa cagcaccagc tgcccaaccg aggagagctg 3900
gtggagcgga tgatgaaagc ttgcggccgc ttcgagcaga catgataaga tacattgatg 3960
agtttggaca aaccacaact agaatgcagt gaaaaaaatg ctttatttgt gaaatttgtg 4020
atgctattgc tttatttgta accattataa gctgcaataa acaagttaac aacaacaatt 4080
gcattcattt tatgtttcag gttcaggggg agatgtggga ggtttttttaa agcaagtaaa 4140 acctctacaa atgtggtaaa atcgataagg atcttcctag agcatggcta cgtagataag 4200
tagcatggcg ggttaatcat taactacaag gaacccctag tgatggagtt ggccactccc 4260
tctctgcgcg ctcgctcgct cactgaggcc gggcgaccaa aggtcgcccg acgcccgggc 4320
tttgcccggg cggcctcagt gagcgagcga gcgcgcag 4358

<210> SEQ ID NO 41
<211> LENGTH: 27
<212> TYPE: PRT
<213> ORGANISM: Artificial Sequence
<220> FEATURE:
<223> OTHER INFORMATION: Proline-rich peptide domain

<400> SEQUENCE: 41

Pro Ser Pro Pro Leu Pro Pro Pro Pro Pro Pro Pro Pro Pro Pro Pro
1 5 10 15

Pro Pro Pro Pro Pro Pro Pro Pro Pro Leu Pro
20 25

<210> SEQ ID NO 42
<211> LENGTH: 153
<212> TYPE: PRT
<213> ORGANISM: Homo sapiens

<400> SEQUENCE: 42

Met Val Asp Leu Thr Gln Val Met Asp Asp Glu Val Phe Met Ala Phe
1 5 10 15

Ala Ser Tyr Ala Thr Ile Ile Leu Ser Lys Met Met Leu Met Ser Thr
20 25 30

Ala Thr Ala Phe Tyr Arg Leu Thr Arg Lys Val Phe Ala Asn Pro Glu
35 40 45

```
Asp Cys Val Phe Gly Lys Gly Glu Asn Ala Lys Lys Tyr Leu Arg Thr
    50                  55                  60

Asp Asp Arg Val Glu Arg Val Arg Arg Ala His Leu Asn Asp Leu Glu
65                  70                  75                  80

Asn Ile Ile Pro Phe Leu Gly Ile Gly Leu Leu Tyr Ser Leu Ser Gly
                85                  90                  95

Pro Asp Pro Ser Thr Ala Ile Leu His Phe Arg Leu Phe Val Gly Ala
            100                 105                 110

Arg Ile Tyr His Thr Ile Ala Tyr Leu Thr Pro Leu Pro Gln Pro Asn
        115                 120                 125

Arg Ala Leu Ser Phe Phe Val Gly Tyr Gly Val Thr Ser Met Ala Tyr
    130                 135                 140

Arg Leu Leu Lys Ser Lys Leu Tyr Leu
145                 150
```

<210> SEQ ID NO 43
<211> LENGTH: 222
<212> TYPE: PRT
<213> ORGANISM: Homo sapiens

<400> SEQUENCE: 43

```
Met Ala Glu Lys Pro Lys Leu His Tyr Phe Asn Ala Arg Gly Arg Met
1               5                   10                  15

Glu Ser Thr Arg Trp Leu Leu Ala Ala Ala Gly Val Glu Phe Glu Glu
            20                  25                  30

Lys Phe Ile Lys Ser Ala Glu Asp Leu Asp Lys Leu Arg Asn Asp Gly
        35                  40                  45

Tyr Leu Met Phe Gln Gln Val Pro Met Val Glu Ile Asp Gly Met Lys
    50                  55                  60

Leu Val Gln Thr Arg Ala Ile Leu Asn Tyr Ile Ala Ser Lys Tyr Asn
65                  70                  75                  80

Leu Tyr Gly Lys Asp Ile Lys Glu Arg Ala Leu Ile Asp Met Tyr Ile
                85                  90                  95

Glu Gly Ile Ala Asp Leu Gly Glu Met Ile Leu Leu Leu Pro Val Cys
            100                 105                 110

Pro Pro Glu Glu Lys Asp Ala Lys Leu Ala Leu Ile Lys Glu Lys Ile
        115                 120                 125

Lys Asn Arg Tyr Phe Pro Ala Phe Glu Lys Val Leu Lys Ser His Gly
    130                 135                 140

Gln Asp Tyr Leu Val Gly Asn Lys Leu Ser Arg Ala Asp Ile His Leu
145                 150                 155                 160

Val Glu Leu Leu Tyr Tyr Val Glu Glu Leu Asp Ser Ser Leu Ile Ser
                165                 170                 175

Ser Phe Pro Leu Leu Lys Ala Leu Lys Thr Arg Ile Ser Asn Leu Pro
            180                 185                 190

Thr Val Lys Lys Phe Leu Gln Pro Gly Ser Pro Arg Lys Pro Pro Met
        195                 200                 205

Asp Glu Lys Ser Leu Glu Glu Ala Arg Lys Ile Phe Arg Phe
    210                 215                 220
```

<210> SEQ ID NO 44
<211> LENGTH: 297
<212> TYPE: PRT
<213> ORGANISM: Homo sapiens

<400> SEQUENCE: 44

```
Met Val His Gln Val Leu Tyr Arg Ala Leu Val Ser Thr Lys Trp Leu
1               5                   10                  15

Ala Glu Ser Ile Arg Thr Gly Lys Leu Gly Pro Gly Leu Arg Val Leu
            20                  25                  30

Asp Ala Ser Trp Tyr Ser Pro Gly Thr Arg Glu Ala Arg Lys Glu Tyr
        35                  40                  45

Leu Glu Arg His Val Pro Gly Ala Ser Phe Phe Asp Ile Glu Glu Cys
    50                  55                  60

Arg Asp Thr Ala Ser Pro Tyr Glu Met Met Leu Pro Ser Glu Ala Gly
65                  70                  75                  80

Phe Ala Glu Tyr Val Gly Arg Leu Gly Ile Ser Asn His Thr His Val
                85                  90                  95

Val Val Tyr Asp Gly Glu His Leu Gly Ser Phe Tyr Ala Pro Arg Val
            100                 105                 110

Trp Trp Met Phe Arg Val Phe Gly His Arg Thr Val Ser Val Leu Asn
        115                 120                 125

Gly Gly Phe Arg Asn Trp Leu Lys Glu Gly His Pro Val Thr Ser Glu
    130                 135                 140

Pro Ser Arg Pro Glu Pro Ala Val Phe Lys Ala Thr Leu Asp Arg Ser
145                 150                 155                 160

Leu Leu Lys Thr Tyr Glu Gln Val Leu Glu Asn Leu Glu Ser Lys Arg
                165                 170                 175

Phe Gln Leu Val Asp Ser Arg Ser Gln Gly Arg Phe Leu Gly Thr Glu
            180                 185                 190

Pro Glu Pro Asp Ala Val Gly Leu Asp Ser Gly His Ile Arg Gly Ala
        195                 200                 205

Val Asn Met Pro Phe Met Asp Phe Leu Thr Glu Asp Gly Phe Glu Lys
    210                 215                 220

Gly Pro Glu Glu Leu Arg Ala Leu Phe Gln Thr Lys Lys Val Asp Leu
225                 230                 235                 240

Ser Gln Pro Leu Ile Ala Thr Cys Arg Lys Gly Val Thr Ala Cys His
                245                 250                 255

Val Ala Leu Ala Ala Tyr Leu Cys Gly Lys Pro Asp Val Ala Val Tyr
            260                 265                 270

Asp Gly Ser Trp Ser Glu Trp Phe Arg Arg Ala Pro Pro Glu Ser Arg
        275                 280                 285

Val Ser Gln Gly Lys Ser Glu Lys Ala
    290                 295
```

<210> SEQ ID NO 45
<211> LENGTH: 297
<212> TYPE: PRT
<213> ORGANISM: Homo sapiens

<400> SEQUENCE: 45

```
Met Ala Ser Pro Gln Leu Cys Arg Ala Leu Val Ser Ala Gln Trp Val
1               5                   10                  15

Ala Glu Ala Leu Arg Ala Pro Arg Ala Gly Gln Pro Leu Gln Leu Leu
            20                  25                  30

Asp Ala Ser Trp Tyr Leu Pro Lys Leu Gly Arg Asp Ala Arg Arg Glu
        35                  40                  45

Phe Glu Glu Arg His Ile Pro Gly Ala Ala Phe Phe Asp Ile Asp Gln
    50                  55                  60

Cys Ser Asp Arg Thr Ser Pro Tyr Asp His Met Leu Pro Gly Ala Glu
```

65 70 75 80

His Phe Ala Glu Tyr Ala Gly Arg Leu Gly Val Gly Ala Ala Thr His
85 90 95

Val Val Ile Tyr Asp Ala Ser Asp Gln Gly Leu Tyr Ser Ala Pro Arg
100 105 110

Val Trp Trp Met Phe Arg Ala Phe Gly His His Ala Val Ser Leu Leu
115 120 125

Asp Gly Gly Leu Arg His Trp Leu Arg Gln Asn Leu Pro Leu Ser Ser
130 135 140

Gly Lys Ser Gln Pro Ala Pro Ala Glu Phe Arg Ala Gln Leu Asp Pro
145 150 155 160

Ala Phe Ile Lys Thr Tyr Glu Asp Ile Lys Glu Asn Leu Glu Ser Arg
165 170 175

Arg Phe Gln Val Val Asp Ser Arg Ala Thr Gly Arg Phe Arg Gly Thr
180 185 190

Glu Pro Glu Pro Arg Asp Gly Ile Glu Pro Gly His Ile Pro Gly Thr
195 200 205

Val Asn Ile Pro Phe Thr Asp Phe Leu Ser Gln Glu Gly Leu Glu Lys
210 215 220

Ser Pro Glu Glu Ile Arg His Leu Phe Gln Glu Lys Lys Val Asp Leu
225 230 235 240

Ser Lys Pro Leu Val Ala Thr Cys Gly Ser Gly Val Thr Ala Cys His
245 250 255

Val Ala Leu Gly Ala Tyr Leu Cys Gly Lys Pro Asp Val Pro Ile Tyr
260 265 270

Asp Gly Ser Trp Val Glu Trp Tyr Met Arg Ala Arg Pro Glu Asp Val
275 280 285

Ile Ser Glu Gly Arg Gly Lys Thr His
290 295

<210> SEQ ID NO 46
<211> LENGTH: 296
<212> TYPE: PRT
<213> ORGANISM: Homo sapiens

<400> SEQUENCE: 46

Met Ala Ser Pro Gln Leu Cys Arg Ala Leu Val Ser Ala Gln Trp Val
1 5 10 15

Ala Glu Ala Leu Arg Ala Pro Arg Ala Gly Gln Pro Leu Gln Leu Leu
20 25 30

Asp Ala Ser Trp Tyr Leu Pro Lys Leu Gly Arg Asp Ala Thr Gln Phe
35 40 45

Glu Glu Arg His Ile Pro Gly Ala Ala Phe Phe Asp Ile Asp Gln Cys
50 55 60

Ser Asp Arg Thr Ser Pro Tyr Asp His Met Leu Pro Gly Ala Glu His
65 70 75 80

Phe Ala Glu Tyr Ala Gly Arg Leu Gly Val Gly Ala Ala Thr His Val
85 90 95

Val Ile Tyr Asp Ala Ser Asp Gln Gly Leu Tyr Ser Ala Pro Arg Val
100 105 110

Trp Trp Met Phe Arg Ala Phe Gly His His Ala Val Ser Leu Leu Asp
115 120 125

Gly Gly Leu Arg His Trp Leu Arg Gln Asn Leu Pro Leu Ser Ser Gly
130 135 140

```
Lys Ser Gln Pro Ala Pro Ala Glu Phe Arg Ala Gln Leu Asp Pro Ala
145                 150                 155                 160

Phe Ile Lys Thr Tyr Glu Asp Ile Lys Glu Asn Leu Glu Ser Arg Arg
                165                 170                 175

Phe Gln Val Val Asp Ser Arg Ala Thr Gly Arg Phe Arg Gly Thr Glu
            180                 185                 190

Pro Glu Pro Arg Asp Gly Ile Glu Pro Gly His Ile Pro Gly Thr Val
        195                 200                 205

Asn Ile Pro Phe Thr Asp Phe Leu Ser Gln Glu Gly Leu Glu Lys Ser
    210                 215                 220

Pro Glu Glu Ile Arg His Leu Phe Gln Glu Lys Lys Val Asp Leu Ser
225                 230                 235                 240

Lys Pro Leu Val Ala Thr Cys Gly Ser Gly Val Thr Ala Cys His Val
                245                 250                 255

Ala Leu Gly Ala Tyr Leu Cys Gly Lys Pro Asp Val Pro Ile Tyr Asp
            260                 265                 270

Gly Ser Trp Val Glu Trp Tyr Met Arg Ala Arg Pro Glu Asp Val Ile
        275                 280                 285

Ser Glu Gly Arg Gly Lys Thr His
    290                 295


<210> SEQ ID NO 47
<211> LENGTH: 738
<212> TYPE: PRT
<213> ORGANISM: Unknown
<220> FEATURE:
<223> OTHER INFORMATION: AAV8 capsid

<400> SEQUENCE: 47

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205
```

```
Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
```

```
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu


<210> SEQ ID NO 48
<211> LENGTH: 51
<212> TYPE: PRT
<213> ORGANISM: Homo sapiens

<400> SEQUENCE: 48

Pro Gln Lys Ser Cys Ser Lys Val Thr Asp Ser Cys Arg His Val Cys
1               5                   10                  15

Gln Cys Arg Pro Pro Pro Pro Leu Pro Pro Pro Pro Pro Arg Leu Leu
            20                  25                  30

Ser Ala Pro Ala Pro Asn Ser Thr Ser Cys Pro Thr Glu Glu Ser Trp
        35                  40                  45

Trp Ser Gly
    50


<210> SEQ ID NO 49
<211> LENGTH: 72
<212> TYPE: PRT
<213> ORGANISM: Homo sapiens

<400> SEQUENCE: 49

Ser Pro Gln Pro Lys Ile Val Thr Pro Tyr Thr Ala Ser Gln Pro Ser
1               5                   10                  15

Pro Pro Leu Pro Pro Pro Pro Pro Pro Pro Pro Pro Pro Pro Pro Pro
            20                  25                  30

Pro Pro Pro Pro Pro Pro Pro Leu Pro Ser Gln Ser Ala Pro Ser Ala
        35                  40                  45

Gly Ser Ala Ala Pro Met Phe Val Lys Tyr Ser Thr Ile Thr Arg Leu
    50                  55                  60

Gln Asn Ala Ser Gln His Ser Gly
65                  70


<210> SEQ ID NO 50
<211> LENGTH: 1731
<212> TYPE: DNA
<213> ORGANISM: Artificial Sequence
<220> FEATURE:
<223> OTHER INFORMATION: CB7 promoter

<400> SEQUENCE: 50

ctagtcgaca ttgattattg actagttatt aatagtaatc aattacgggg tcattagttc      60

atagcccata tatggagttc cgcgttacat aacttacggt aaatggcccg cctggctgac     120
```

```
cgcccaacga cccccgccca ttgacgtcaa taatgacgta tgttcccata gtaacgccaa    180

tagggacttt ccattgacgt caatgggtgg agtatttacg gtaaactgcc cacttggcag    240

tacatcaagt gtatcatatg ccaagtacgc cccctattga cgtcaatgac ggtaaatggc    300

ccgcctggca ttatgcccag tacatgacct tatgggactt tcctacttgg cagtacatct    360

acgtattagt catcgctatt accatggtcg aggtgagccc cacgttctgc ttcactctcc    420

ccatctcccc cccctcccca cccccaattt tgtatttatt tattttttaa ttattttgtg    480

cagcgatggg ggcggggggg gggggggggc gcgcgccagg cggggcgggg cggggcgagg    540

ggcggggcgg ggcgaggcgg agaggtgcgg cggcagccaa tcagagcggc gcgctccgaa    600

agtttccttt tatggcgagg cggcggcggc ggcggcccta taaaaagcga agcgcgcggc    660

gggcgggagt cgctgcgcgc tgccttcgcc ccgtgccccg ctccgccgcc gcctcgcgcc    720

gcccgccccg gctctgactg accgcgttac tcccacaggt gagcgggcgg gacggccctt    780

ctcctccggg ctgtaattag cgcttggttt aatgacggct tgtttctttt ctgtggctgc    840

gtgaaagcct tgaggggctc cgggagggcc ctttgtgcgg ggggagcggc tcggggggtg    900

cgtgcgtgtg tgtgtgcgtg gggagcgccg cgtgcggctc cgcgctgccc ggcggctgtg    960

agcgctgcgg gcgcggcgcg gggctttgtg cgctccgcag tgtgcgcgag gggagcgcgg   1020

ccgggggcgg tgccccgcgg tgcggggggg gctgcgaggg gaacaaaggc tgcgtgcggg   1080

gtgtgtgcgt gggggggtga gcagggggtg tgggcgcgtc ggtcgggctg caaccccccc   1140

tgcacccccc tccccgagtt gctgagcacg gcccggcttc gggtgcgggg ctccgtacgg   1200

ggcgtggcgc ggggctcgcc gtgccgggcg gggggtggcg gcaggtgggg gtgccgggcg   1260

gggcggggcc gcctcgggcc ggggagggct cgggggaggg gcgcggcggc ccccggagcg   1320

ccggcggctg tcgaggcgcg gcgagccgca gccattgcct tttatggtaa tcgtgcgaga   1380

gggcgcaggg acttcctttg tcccaaatct gtgcggagcc gaaatctggg aggcgccgcc   1440

gcaccccctc tagcgggcgc ggggcgaagc ggtgcggcgc cggcaggaag gaaatgggcg   1500

gggagggcct tcgtgcgtcg ccgcgccgcc gtccccttct ccctctccag cctcggggct   1560

gtccgcgggg ggacggctgc cttcgggggg gacggggcag ggcggggttc ggcttctggc   1620

gtgtgaccgg cggctctaga gcctctgcta accatgttca tgccttcttc tttttcctac   1680

agctcctggg caacgtgctg gttattgtgc tgtctcatca ttttggcaaa g             1731
```

```
<210> SEQ ID NO 51
<211> LENGTH: 4852
<212> TYPE: DNA
<213> ORGANISM: Artificial Sequence
<220> FEATURE:
<223> OTHER INFORMATION: C4/UbC.hIL2.BChE C1.IRES.PRIMA.RBG
<220> FEATURE:
<221> NAME/KEY: repeat_region
<222> LOCATION: (1)..(130)
<223> OTHER INFORMATION: 5'ITR
<220> FEATURE:
<221> NAME/KEY: enhancer
<222> LOCATION: (279)..(538)
<223> OTHER INFORMATION: C4 enhancer with 2 mismatches
<220> FEATURE:
<221> NAME/KEY: promoter
<222> LOCATION: (565)..(1793)
<223> OTHER INFORMATION: UbC promoter
<220> FEATURE:
<221> NAME/KEY: misc_feature
<222> LOCATION: (1828)..(3626)
<223> OTHER INFORMATION: BChE C1 with human IL2 leader
<220> FEATURE:
<221> NAME/KEY: misc_feature
```

```
<222> LOCATION: (1837)..(1893)
<223> OTHER INFORMATION: human IL2 leader
<220> FEATURE:
<221> NAME/KEY: misc_feature
<222> LOCATION: (3627)..(4217)
<223> OTHER INFORMATION: IRES
<220> FEATURE:
<221> NAME/KEY: misc_feature
<222> LOCATION: (4222)..(4447)
<223> OTHER INFORMATION: PRIMA1
<220> FEATURE:
<221> NAME/KEY: polyA_signal
<222> LOCATION: (4508)..(4634)
<223> OTHER INFORMATION: Rabbit beta globin polyA
<220> FEATURE:
<221> NAME/KEY: repeat_region
<222> LOCATION: (4723)..(4852)

<400> SEQUENCE: 51

ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct tgtagttaat gattaacccg ccatgctact tatctaccag ggtaatgggg    180

atcctctaga actatagcta gtcgacattg attattgact agttattaat agtaatcaat    240

tacggggtca ttagttcata gcccatatat ggagttccgc gttacataac ttacggtaaa    300

tggcccgcct ggctgaccgc ccaacgaccc ccgcccattg acgtcaataa tgacgtatgt    360

tcccatagta acgccaatag ggactttcca ttgacgtcaa tgggtggagt atttacggta    420

aactgcccac ttggcagtac atcaagtgta tcatatgcca agtacgcccc ctattgacgt    480

caatgacggt aaatggcccg cctggcatta tgcccagtac atgaccttat gggactttcc    540

tacttggcag tacatctacg atctggcctc cgcgccgggt tttggcgcct cccgcgggcg    600

ccccccctcct cacggcgagc gctgccacgt cagacgaagg gcgcagcgag cgtcctgatc    660

cttccgcccg gacgctcagg acagcggccc gctgctcata agactcggcc ttagaacccc    720

agtatcagca gaaggacatt ttaggacggg acttgggtga ctctagggca ctggttttct    780

ttccagagag cggaacaggc gaggaaaagt agtcccttct cggcgattct gcggagggat    840

ctccgtgggg cggtgaacgc cgatgattat ataaggacgc gccgggtgtg gcacagctag    900

ttccgtcgca gccgggattt gggtcgcggt tcttgtttgt ggatcgctgt gatcgtcact    960

tggtgagtag cgggctgctg ggctggccgg ggctttcgtg gccgccgggc cgctcggtgg   1020

gacggaagcg tgtggagaga ccgccaaggg ctgtagtctg ggtccgcgag caaggttgcc   1080

ctgaactggg ggttgggggg agcgcagcaa aatggcggct gttcccgagt cttgaatgga   1140

agacgcttgt gaggcgggct gtgaggtcgt tgaaacaagg tgggggggcat ggtgggcggc   1200

aagaacccaa ggtcttgagg ccttcgctaa tgcgggaaag ctcttattcg ggtgagatgg   1260

gctggggcac catctgggga ccctgacgtg aagtttgtca ctgactggag aactcggttt   1320

gtcgtctgtt gcgggggcgg cagttatggc ggtgccgttg ggcagtgcac ccgtaccttt   1380

gggagcgcgc gccctcgtcg tgtcgtgacg tcacccgttc tgttggctta taatgcaggg   1440

tggggccacc tgccggtagg tgtgcggtag gcttttctcc gtcgcaggac gcagggttcg   1500

ggcctagggt aggctctcct gaatcgacag gcgccggacc tctggtgagg ggagggataa   1560

gtgaggcgtc agtttctttg gtcggtttta tgtacctatc ttcttaagta gctgaagctc   1620

cggttttgaa ctatgcgctc ggggttggcg agtgtgtttt gtgaagtttt ttaggcacct   1680

tttgaaatgt aatcatttgg gtcaatatgt aattttcagt gttagactag taaattgtcc   1740

gctaaattct ggccgttttt ggcttttttg ttagacgaag cttggtaccg agctcggatc   1800
```

```
cactagtcca gtgtggtgga attcgctaga cccaccatgc ggatgcagct gctgctgctg   1860
attgctctga gcctggctct ggtgaccaac agcgaagacg acattattat tgctaccaag   1920
aacggcaagg tgcggggcat gaacctgacc gtgtttggcg gcaccgtgac cgcttttctg   1980
ggcattccct atgctcagcc ccccctgggc cggctgcggt ttaagaagcc ccagagcctg   2040
accaagtgga gcgacatttg gaacgctacc aagtatgcta acagctgttg tcagaacatt   2100
gaccagagct ttcccggctt tcatggcagc gaaatgtgga accccaacac cgacctgagc   2160
gaagactgtc tgtatctgaa cgtgtggatt cccgctccca agcccaagaa cgctaccgtg   2220
ctgatttgga tttatggcgg cggctttcag accggcacca gcagcctgca tgtgtatgac   2280
ggcaagtttc tggctcgggt ggaacgggtg attgtggtga gcatgaacta tcgggtgggc   2340
gctctgggct ttctggctct gcccggcaac cccgaagctc ccggcaacat gggcctgttt   2400
gaccagcagc tggctctgca gtgggtgcag aagaacattg ctgcttttgg cggcaacccc   2460
aagagcgtga ccctgtttgg cgaaagcgct ggcgctgcta gcgtgagcct gcatctgctg   2520
agccccggca gccatagcct gtttacccgg gctattctgc agagcggcag ctttaacgct   2580
ccctgggctg tgaccagcct gtatgaagct cggaaccgga ccctgaacct ggctaagctg   2640
accggctgta gccgggaaaa cgaaaccgaa attattaagt gtctgcggaa caaggacccc   2700
caggaaattc tgctgaacga agcttttgtg gtgccctatg gcacccccct gagcgtgaac   2760
tttggcccca ccgtggacgg cgactttctg accgacatgc ccgacattct gctggaactg   2820
ggccagttta agaagaccca gattctggtg ggcgtgaaca aggacgaagg caccgctttt   2880
ctggtgtatg gcgctcccgg ctttagcaag gacaacaaca gcattattac ccggaaggaa   2940
tttcaggaag gcctgaagat ttttttcccc ggcgtgagcg aatttggcaa ggaaagcatt   3000
ctgtttcatt ataccgactg ggtggacgac cagcggcccg aaaactatcg ggaagctctg   3060
ggcgacgtgg tgggcgacta taactttatt tgtcccgctc tggaatttac caagaagttt   3120
agcgaatggg gcaacaacgc tttttttat tattttgaac atcggagcag caagctgccc   3180
tggcccgaat ggatgggcgt gatgcatggc tatgaaattg aatttgtgtt tggcctgccc   3240
ctggaacggc gggacaacta taccaaggct gaagaaattc tgagccggag cattgtgaag   3300
cggtgggcta actttgctaa gtatggcaac cccaacgaaa cccagaacaa cagcaccagc   3360
tggcccgtgt ttaagagcac cgaacagaag tatctgaccc tgaacaccga aagcacccgg   3420
attatgacca agctgcgggc tcagcagtgt cggttttgga ccagcttttt tcccaaggtg   3480
ctggaaatga ccggcaacat tgacgaagct gaatgggaat ggaaggctgg ctttcatcgg   3540
tggaacaact atatgatgga ctggaagaac cagtttaacg actataccag caagaaggaa   3600
agctgtgtgg gcctgtgata aggccggccc ctctccctcc cccccccta acgttactgg   3660
ccgaagccgc ttggaataag gccggtgtgc gtttgtctat atgttatttt ccaccatatt   3720
gccgtctttt ggcaatgtga gggcccggaa acctggccct gtcttcttga cgagcattcc   3780
taggggtctt tcccctctcg ccaaaggaat gcaaggtctg ttgaatgtcg tgaaggaagc   3840
agttcctctg gaagcttctt gaagacaaac aacgtctgta gcgacccttt gcaggcagcg   3900
gaacccccca cctggcgaca ggtgcctctg cggccaaaag ccacgtgtat aagatacacc   3960
tgcaaaggcg gcacaacccc agtgccacgt tgtgagttgg atagttgtgg aaagagtcaa   4020
atggctctcc tcaagcgtat tcaacaaggg gctgaaggat gcccagaagg taccccattg   4080
tatgggatct gatctggggc ctcggtacac atgctttaca tgtgtttagt cgaggttaaa   4140
```

-continued

```
aaaacgtcta ggccccccga accacgggga cgtggttttc ctttgaaaaa cacgatgata   4200
atatggccac aaccatgtac cgcatgcaac tcctgtcttg cattgcacta agtcttgcac   4260
ttgtcacaaa cagtccacag aagagctgca gcaaggtgac cgatagctgc cggcacgtgt   4320
gccagtgccg gccaccacca ccactgccac caccaccacc acggctgctg agcgccccag   4380
ccccaaacag caccagctgc ccaaccgagg agagctggtg gagcggatga tgaaagcttg   4440
cggccgcggt acctctagag tcgacccggg cggcctcgag gacggggtga actacgcctg   4500
aggatccgat ctttttccct ctgccaaaaa ttatggggac atcatgaagc cccttgagca   4560
tctgacttct ggctaataaa ggaaatttat tttcattgca atagtgtgtt ggaatttttt   4620
gtgtctctca ctcggaagca attcgttgat ctgaatttcg accacccata atacccatta   4680
ccctggtaga taagtagcat ggcgggttaa tcattaacta caaggaaccc ctagtgatgg   4740
agttggccac tccctctctg cgcgctcgct cgctcactga ggccgggcga ccaaaggtcg   4800
cccgacgccc gggctttgcc cgggcggcct cagtgagcga gcgagcgcgc ag           4852
```